United States Patent
Sobrino-Serrano et al.

(10) Patent No.: US 8,673,020 B2
(45) Date of Patent: Mar. 18, 2014

(54) ESOPHAGEAL VALVE DEVICE FOR PLACING IN THE CARDIA

(75) Inventors: Gabriel Sobrino-Serrano, Kinvara (IE); Niall Behan, Kilcolgan (IE); Anthony O'Halloran, Turloughmore (IE)

(73) Assignee: Vysera Biomedical Limited, Galway (IE)

( * ) Notice: Subject to any disclaimer, the term of this patent is extended or adjusted under 35 U.S.C. 154(b) by 0 days.

(21) Appl. No.: 13/554,666

(22) Filed: Jul. 20, 2012

(65) Prior Publication Data

US 2012/0283842 A1    Nov. 8, 2012

Related U.S. Application Data

(63) Continuation of application No. 12/488,037, filed on Jun. 19, 2009, now Pat. No. 8,500,821.

(60) Provisional application No. 61/074,393, filed on Jun. 20, 2008, provisional application No. 61/074,400, filed on Jun. 20, 2008, provisional application No. 61/145,337, filed on Jan. 16, 2009, provisional application No. 61/145,332, filed on Jan. 16, 2009, provisional application No. 61/151,968, filed on Feb. 12, 2009, provisional application No. 61/151,973, filed on Feb. 12, 2009, provisional application No. 61/174,536, filed on May 1, 2009, provisional application No. 61/181,043, filed on May 26, 2009.

(51) Int. Cl.

| A61F 2/04 | (2013.01) |
|---|---|
| A61M 5/00 | (2006.01) |
| A61F 2/06 | (2013.01) |
| A61F 2/20 | (2006.01) |

(52) U.S. Cl.
USPC ............... 623/23.68; 604/9; 623/1.24; 623/9

(58) Field of Classification Search
USPC ................. 600/29–31; 604/8–9; 623/1.24, 9, 623/23.64–23.7
See application file for complete search history.

(56) References Cited

U.S. PATENT DOCUMENTS

| 4,265,694 A * | 5/1981 | Boretos et al. ................. 156/242 |
| 4,271,827 A | 6/1981 | Angelchik |
| 4,603,152 A | 7/1986 | Laurin et al. |
| 4,675,361 A * | 6/1987 | Ward, Jr. ..................... 525/92 A |
| 4,747,849 A | 5/1988 | Galtier |

(Continued)

FOREIGN PATENT DOCUMENTS

| GB | 1354691 A | 5/1974 |
| WO | WO-91/01117 A1 | 2/1991 |

(Continued)

OTHER PUBLICATIONS

International Search Report for PCT/IE2009/000037 (Sep. 3, 2009).

(Continued)

*Primary Examiner* — Andrew Iwamaye
(74) *Attorney, Agent, or Firm* — Studebaker & Brackett PC

(57) ABSTRACT

A luminal valve for placing in a body lumen comprises at least four valve leaflets. The valve has a normally closed configuration in which the leaflets are engaged and an open configuration in which the leaflets are open. The valve may be mounted to an esophageal support.

14 Claims, 33 Drawing Sheets

(56) References Cited

U.S. PATENT DOCUMENTS

| | | | |
|---|---|---|---|
| 4,846,836 A | 7/1989 | Reich | |
| 4,932,938 A | 6/1990 | Goldberg et al. | |
| 4,932,948 A | 6/1990 | Kernes et al. | |
| 5,131,906 A | 7/1992 | Ghen | |
| 5,140,999 A | 8/1992 | Ardito | |
| 5,314,473 A | 5/1994 | Godin | |
| 5,484,418 A | 1/1996 | Quiachon et al. | |
| 5,549,657 A | 8/1996 | Stern et al. | |
| 5,653,747 A | 8/1997 | Dereume | |
| 5,782,808 A | 7/1998 | Folden | |
| 5,800,339 A | 9/1998 | Salama | |
| 5,887,594 A | 3/1999 | LoCicero, III | |
| 6,027,442 A | 2/2000 | Von Iderstein | |
| 6,050,934 A | 4/2000 | Mikhail et al. | |
| 6,066,088 A | 5/2000 | Davis | |
| 6,096,070 A | 8/2000 | Ragheb et al. | |
| 6,234,956 B1 | 5/2001 | He et al. | |
| 6,254,642 B1 | 7/2001 | Taylor | |
| 6,264,700 B1 | 7/2001 | Kilcoyne et al. | |
| 6,302,917 B1 | 10/2001 | Dua et al. | |
| 6,432,040 B1 | 8/2002 | Meah | |
| 6,544,291 B2 | 4/2003 | Taylor | |
| 6,558,429 B2 | 5/2003 | Taylor | |
| 6,669,713 B2 | 12/2003 | Adams | |
| 6,726,696 B1 | 4/2004 | Houser et al. | |
| 6,746,489 B2 | 6/2004 | Dua et al. | |
| 6,790,237 B2 | 9/2004 | Stinson | |
| 6,908,447 B2 | 6/2005 | McWeeney et al. | |
| 6,921,361 B2 | 7/2005 | Suzuki et al. | |
| 6,921,378 B2 | 7/2005 | O'Keefe et al. | |
| 6,958,079 B2 | 10/2005 | Taylor et al. | |
| 6,960,233 B1 | 11/2005 | Berg et al. | |
| 6,976,950 B2 | 12/2005 | Connors et al. | |
| 7,087,088 B2 | 8/2006 | Berg et al. | |
| 7,182,788 B2 | 2/2007 | Jung et al. | |
| 7,470,247 B2 | 12/2008 | Aliski et al. | |
| 7,524,331 B2 | 4/2009 | Birdsall | |
| 7,601,361 B2 | 10/2009 | Lu et al. | |
| 7,678,144 B2 | 3/2010 | Bailey et al. | |
| 7,717,952 B2* | 5/2010 | Case et al. | 623/1.24 |
| 7,806,921 B2 | 10/2010 | Hoffman | |
| 7,819,836 B2 | 10/2010 | Levine et al. | |
| 8,029,557 B2 | 10/2011 | Sobrino-Serrano et al. | |
| 2001/0020189 A1 | 9/2001 | Taylor | |
| 2001/0020190 A1 | 9/2001 | Taylor | |
| 2002/0065552 A1* | 5/2002 | Jayaraman et al. | 623/1.46 |
| 2003/0018309 A1 | 1/2003 | Breznock | |
| 2003/0060894 A1 | 3/2003 | Dua et al. | |
| 2003/0069635 A1 | 4/2003 | Cartledge et al. | |
| 2003/0188755 A1 | 10/2003 | Milbocker | |
| 2003/0199730 A1 | 10/2003 | Silverman et al. | |
| 2003/0199986 A1 | 10/2003 | McWeeney et al. | |
| 2003/0220621 A1 | 11/2003 | Arkinstall | |
| 2004/0044357 A1 | 3/2004 | Gannoe et al. | |
| 2004/0060563 A1 | 4/2004 | Rapacki et al. | |
| 2004/0087905 A1 | 5/2004 | Breznock et al. | |
| 2004/0199262 A1 | 10/2004 | Dua et al. | |
| 2004/0225247 A1 | 11/2004 | Pugsley et al. | |
| 2004/0225373 A1 | 11/2004 | Pugsley et al. | |
| 2005/0065614 A1* | 3/2005 | Stinson | 623/23.68 |
| 2005/0125075 A1 | 6/2005 | Meade et al. | |
| 2005/0149201 A1 | 7/2005 | McWeeney et al. | |
| 2005/0228505 A1 | 10/2005 | Cornet et al. | |
| 2005/0267499 A1 | 12/2005 | Stack et al. | |
| 2006/0041189 A1 | 2/2006 | Vancaillie | |
| 2006/0041319 A1 | 2/2006 | Taylor et al. | |
| 2006/0106205 A1 | 5/2006 | Gehant | |
| 2006/0135971 A1 | 6/2006 | Swanstrom et al. | |
| 2006/0142789 A1 | 6/2006 | Lehman et al. | |
| 2006/0206097 A1 | 9/2006 | Breznock et al. | |
| 2006/0212052 A1 | 9/2006 | Shin et al. | |
| 2006/0264983 A1 | 11/2006 | Holsten et al. | |
| 2006/0265056 A1 | 11/2006 | Nguyen et al. | |
| 2007/0027528 A1* | 2/2007 | Agnew | 623/1.24 |
| 2007/0198048 A1 | 8/2007 | Behan et al. | |
| 2008/0009781 A1 | 1/2008 | Anwar | |
| 2008/0036113 A1 | 2/2008 | Chun et al. | |
| 2008/0051879 A1 | 2/2008 | Case et al. | |
| 2008/0091261 A1 | 4/2008 | Long et al. | |
| 2008/0109070 A1* | 5/2008 | Wagner et al. | 623/1.41 |
| 2008/0109087 A1 | 5/2008 | Durgin | |
| 2008/0269879 A1* | 10/2008 | Sathe et al. | 623/2.12 |
| 2009/0125104 A1 | 5/2009 | Hoffman | |
| 2009/0177270 A1 | 7/2009 | Agnew et al. | |
| 2009/0209982 A1* | 8/2009 | Hoerstrup et al. | 606/151 |
| 2010/0023114 A1 | 1/2010 | Chambers et al. | |
| 2010/0036504 A1 | 2/2010 | Sobrino-Serrano et al. | |
| 2010/0049306 A1 | 2/2010 | House et al. | |
| 2010/0094209 A1 | 4/2010 | Drasler et al. | |
| 2010/0114327 A1 | 5/2010 | Sobrino-Serrano | |
| 2010/0121461 A1 | 5/2010 | Sobrino-Serrano | |
| 2010/0121462 A1* | 5/2010 | Sobrino-Serrano et al. | 623/23.68 |
| 2010/0130949 A1 | 5/2010 | Garcia | |
| 2010/0131049 A1 | 5/2010 | Perkins et al. | |
| 2010/0137998 A1 | 6/2010 | Sobrino-Serrano | |
| 2010/0312225 A1 | 12/2010 | Armistead | |
| 2011/0015758 A1 | 1/2011 | Lennox et al. | |
| 2011/0106060 A1 | 5/2011 | Atkinson et al. | |
| 2011/0160836 A1 | 6/2011 | Behan | |
| 2011/0190905 A1 | 8/2011 | Behan | |

FOREIGN PATENT DOCUMENTS

| | | |
|---|---|---|
| WO | WO-91/18557 A1 | 12/1991 |
| WO | WO-97/06758 A1 | 2/1997 |
| WO | WO-00/12027 A1 | 3/2000 |
| WO | WO-02/094132 A2 | 11/2002 |
| WO | WO-03003949 A2 | 1/2003 |
| WO | WO-03/011179 A2 | 2/2003 |
| WO | WO-03/017882 A2 | 3/2003 |
| WO | WO-03/030782 A1 | 4/2003 |
| WO | WO-2004/043296 A1 | 5/2004 |
| WO | WO-2005/032422 A1 | 4/2005 |
| WO | WO-2005/058210 A1 | 6/2005 |
| WO | WO-2005/060869 A1 | 7/2005 |
| WO | WO-2006106205 A2 | 10/2006 |
| WO | WO-2007/107990 A2 | 9/2007 |
| WO | WO-2007/136468 A2 | 11/2007 |
| WO | WO2008121409 | 10/2008 |
| WO | WO-2009/126268 A1 | 10/2009 |
| WO | WO-2009/126331 A1 | 10/2009 |
| WO | WO-2009/139878 A1 | 11/2009 |
| WO | WO-2010/115011 A1 | 10/2010 |
| WO | WO-2011/006098 A2 | 3/2011 |

OTHER PUBLICATIONS

International Search Report for PCT/IE2009/000039 (Sep. 3, 2009).
International Search Report for PCT/IE2009/000040 (Sep. 3, 2009).
International Search Report for PCT/IE2006/000145 (Jun. 19, 2007).
International Search Report for PCT/IE2010/000075 (Apr. 26, 2011).
International Search Report for PCT/IE2010/000076 (May 31, 2011).

* cited by examiner

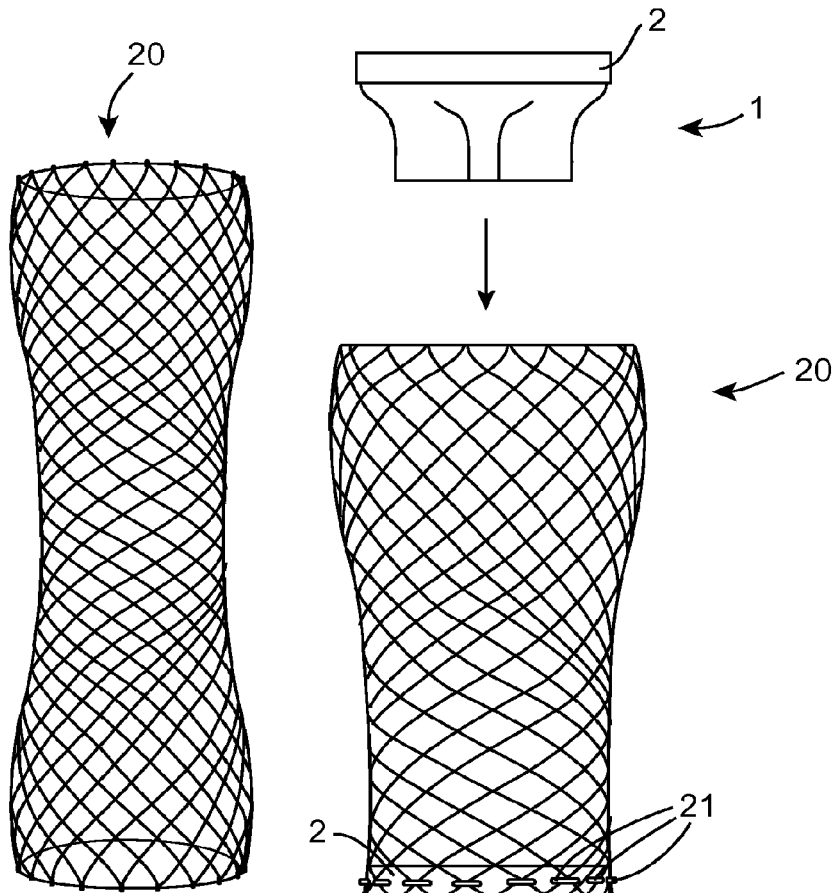
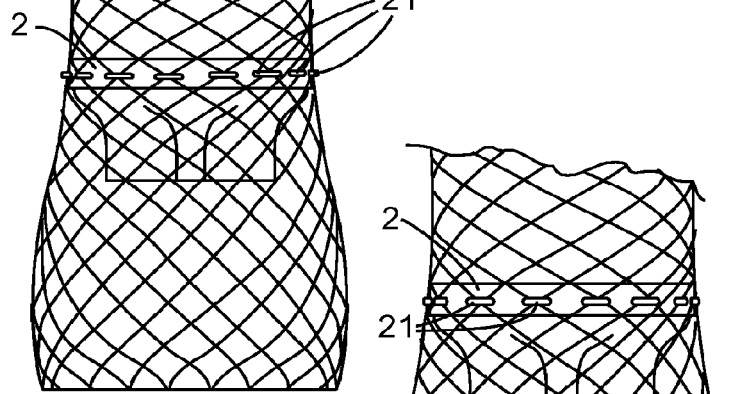
Fig. 23
Fig. 24
Fig. 25

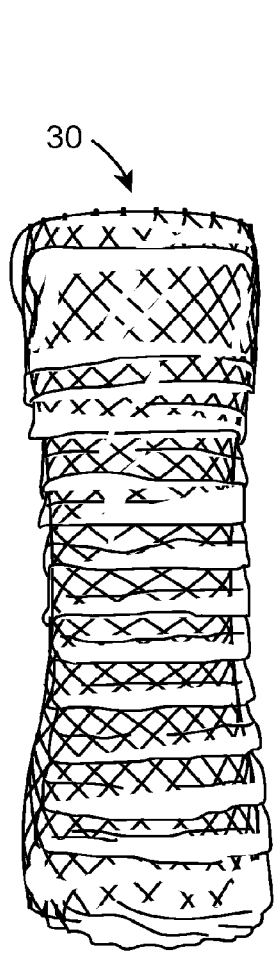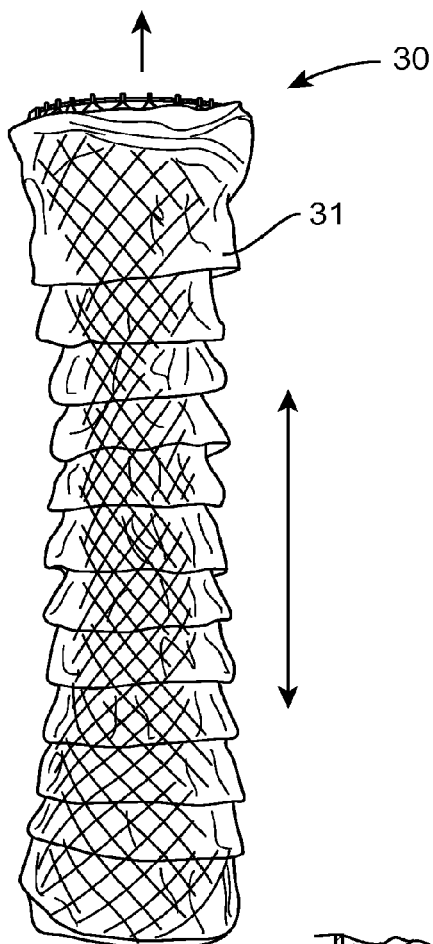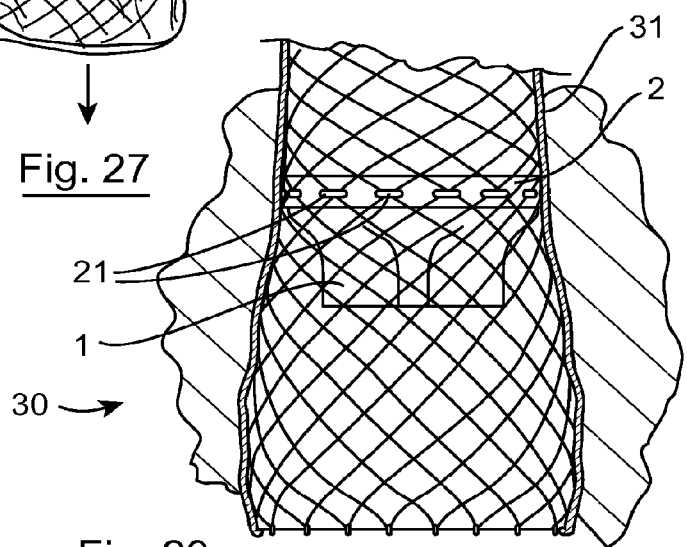
Fig. 26   Fig. 27
Fig. 29

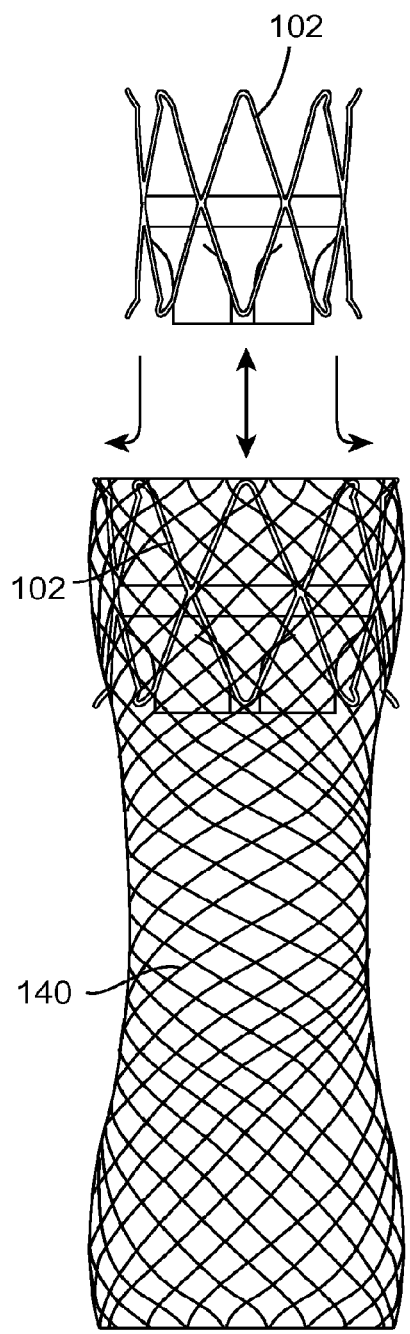
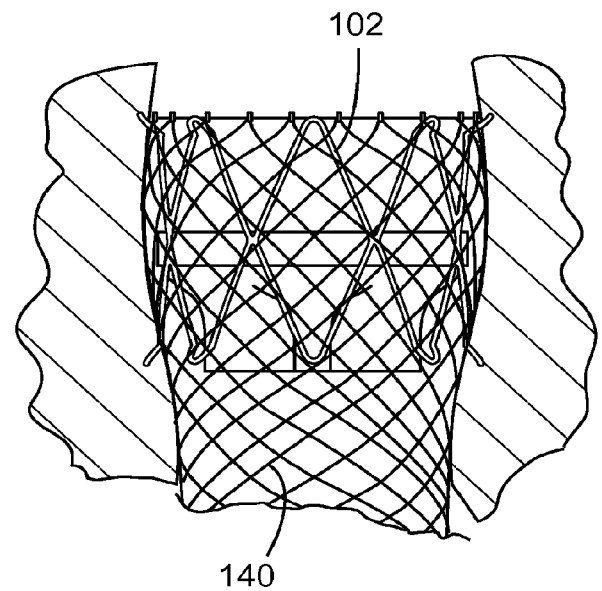
Fig. 36
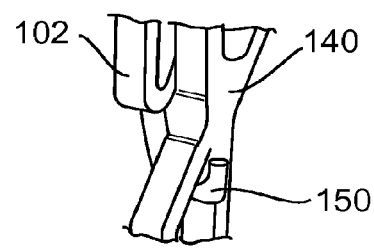
Fig. 37
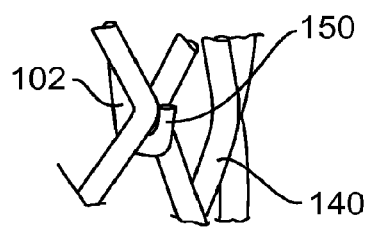
Fig. 35
Fig. 38

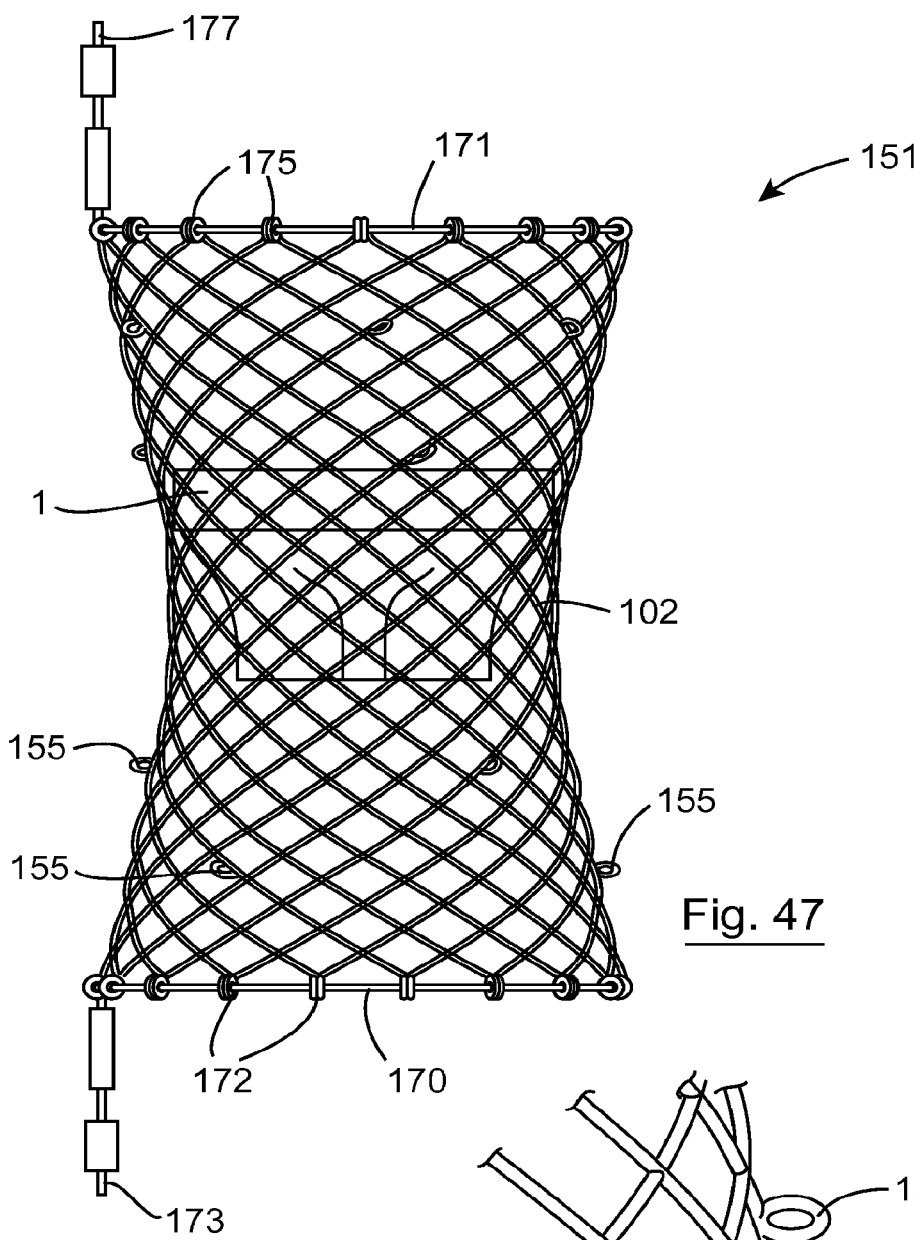
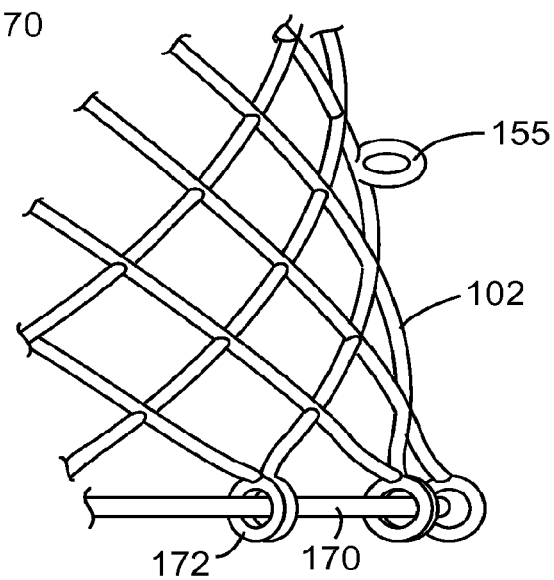
Fig. 47
Fig. 48

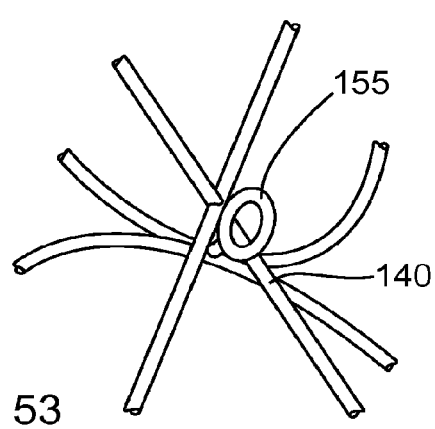
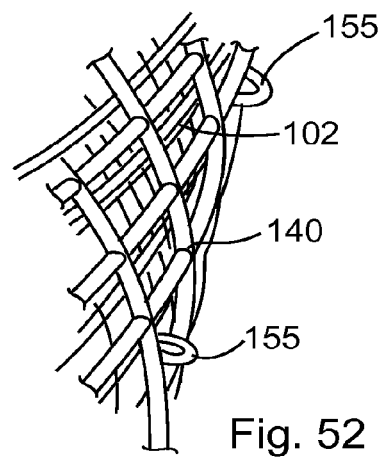
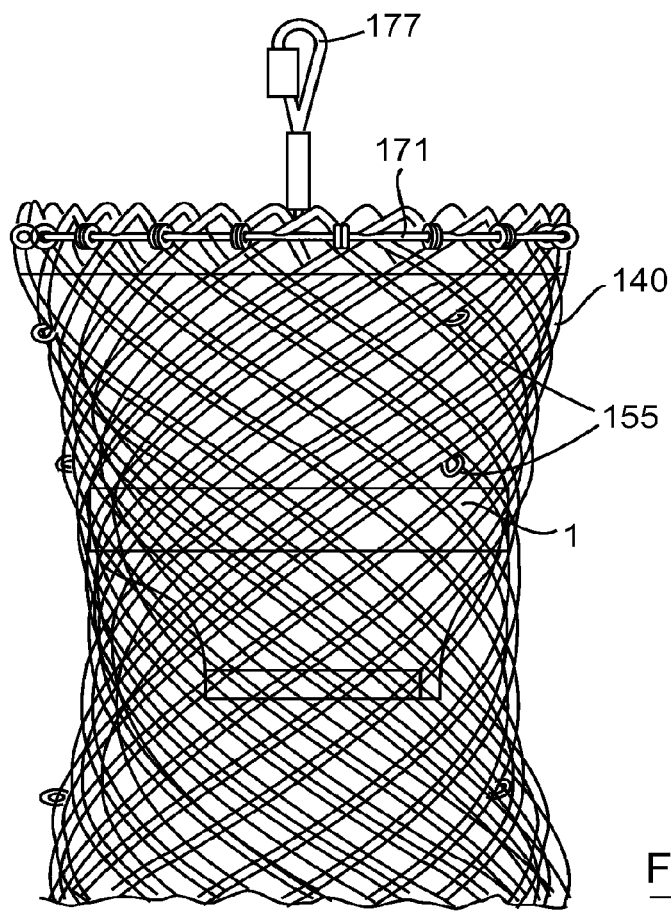
Fig. 53
Fig. 52
Fig. 51

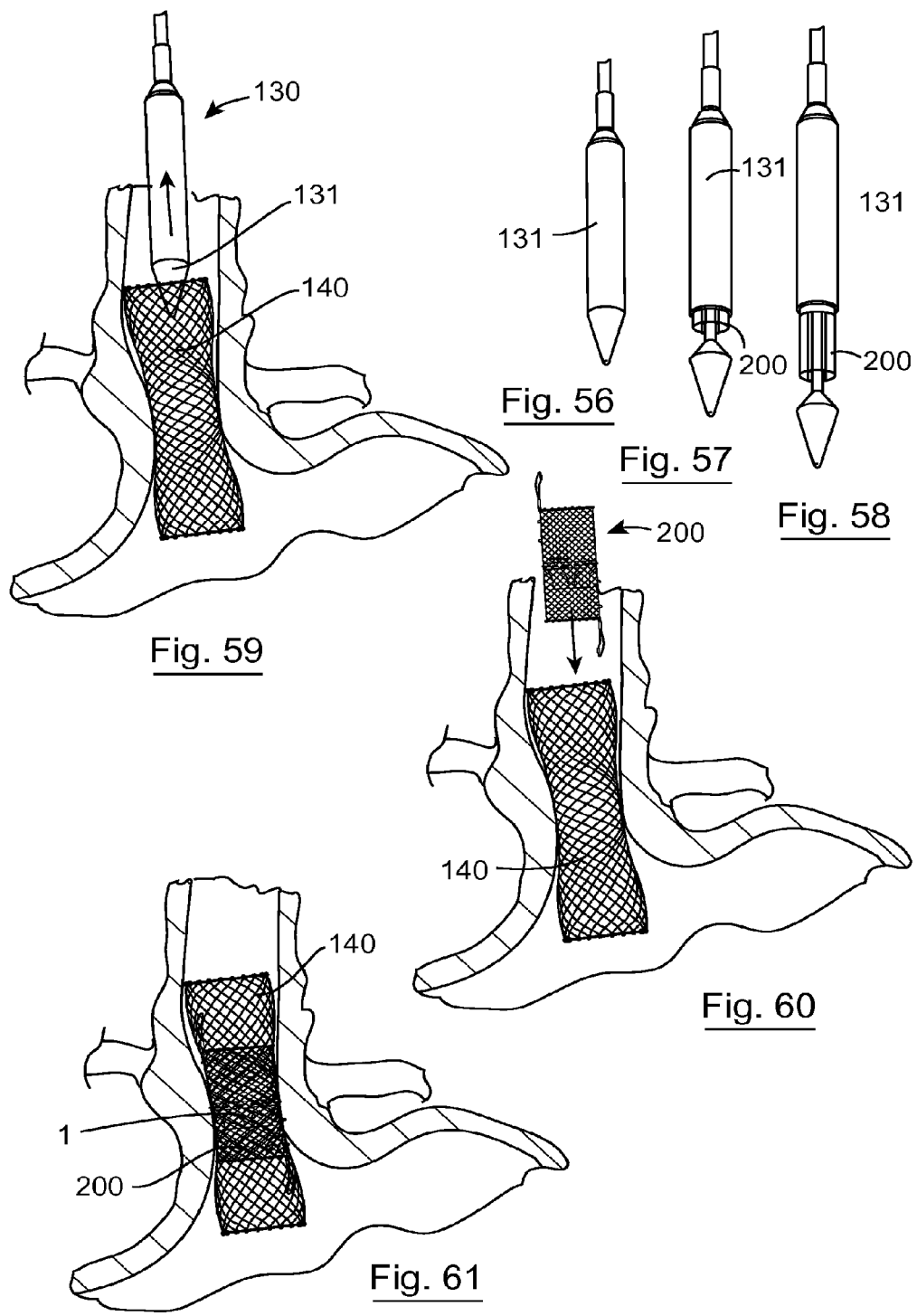

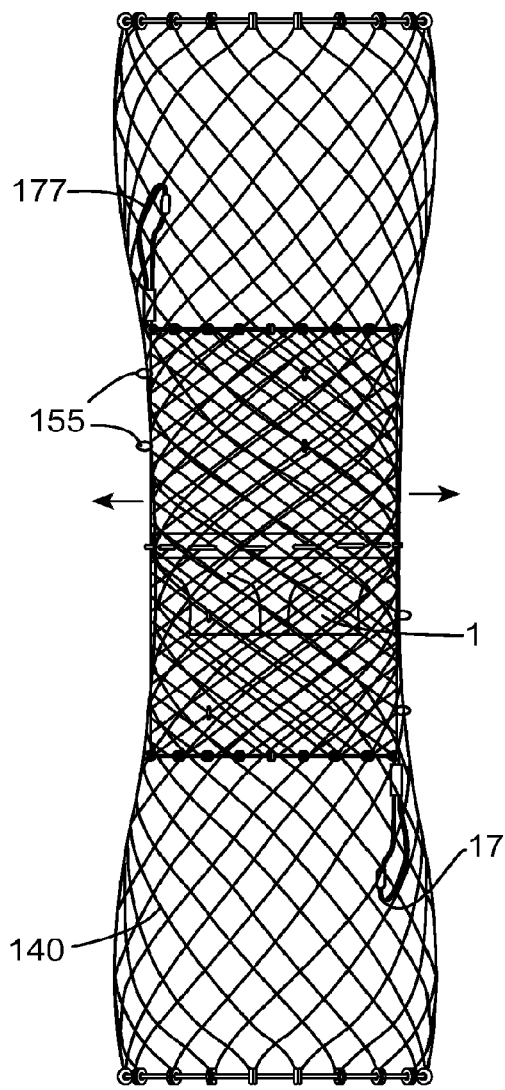
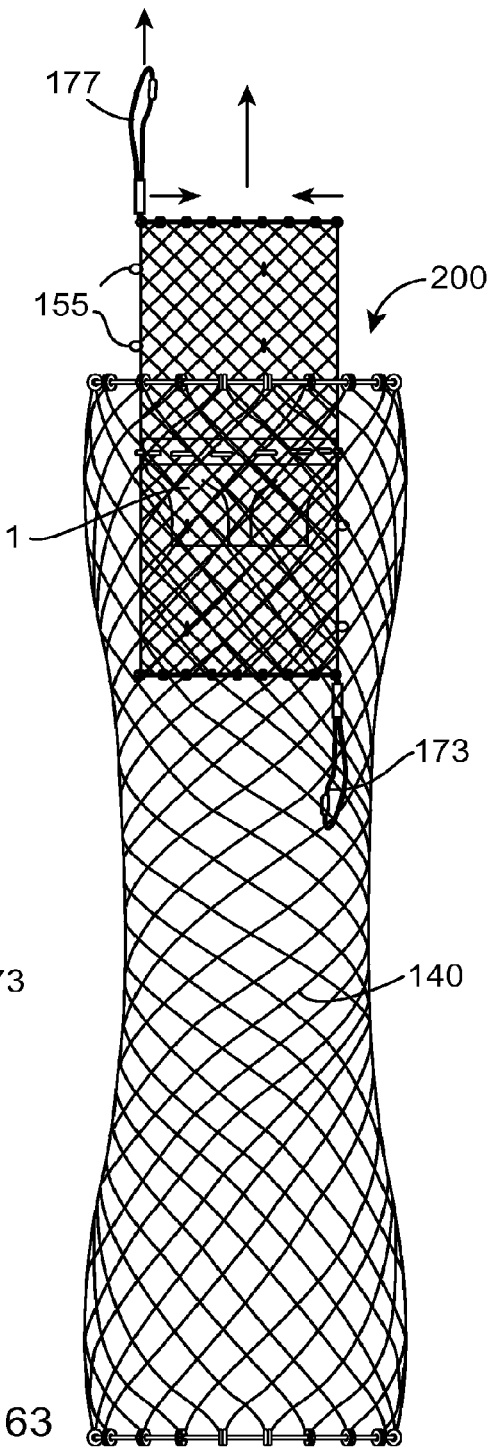
Fig. 62
Fig. 63

ESOPHAGEAL VALVE DEVICE FOR PLACING IN THE CARDIA

CROSS-REFERENCE TO RELATED APPLICATIONS

The present application is a continuation of U.S. patent application Ser. No. 12/488,037 now U.S. Pat. No. 8,500,821 which was filed on Jun. 19, 2009 and which claims the benefit of U.S. Provisional Patent Application No.: 61/074,393 filed Jun. 20, 2008; 61/074,400 filed Jun. 20, 2008; 61/145,337 filed Jan. 16, 2009; 61/145,332 filed Jan. 16, 2009; 61/151,968 filed Feb. 12, 2009; 61/151,973 filed Feb. 12, 2009; 61/174,536 filed May 1, 2009; and 61/181,043 filed May 26, 2009. The entire contents of all of the applications identified in this paragraph are incorporated herein by reference.

INTRODUCTION

An esophageal stent is often placed across the lower esophageal sphincter (LES) to treat benign strictures or malignant obstructions. However, the consequent loss of a reflux barrier often results in significant amounts of acid reflux, which can reduce the quality of life of an already sick patient.

Such esophageal stents that are placed across the gastric cardia are sometimes equipped with a flexible sleeve that hangs below the stent into the stomach. These so called 'windsock' devices rely on the slightly increased pressure of the stomach to flatten and close the sleeve.

However, there are a number of problems with existing in-stent reflux technology. When a patient wishes to belch or vomit many of these devices will seal completely preventing retrograde flow and causing the patient significant discomfort. In some cases the sleeves can invert to allow retrograde flow but may then remain inverted and may cause blockage of the esophagus. In addition, because such sleeves are generally at the distal end of the stent where peristalsis is not effective, there is a risk of food becoming stuck in this portion of the device. Another problem is that the materials that these valves are made from often degrade in the gastric environment thus reducing the efficacy of the devices over time.

STATEMENTS OF INVENTION

According to the invention there is provided an esophageal valve having:
 a normally closed configuration in which the valve is closed;
 an antegrade open configuration in which the valve leaflets are opened in response to an antegrade force to allow flow through the valve; and
 a retrograde open configuration in response to an retrograde force which is substantially larger than the antegrade force.

In one embodiment the valve comprises a polymeric valve body having an outer support rim, at least three valve leaflets, and a main body region extending between the support rim and the valve leaflets.

The invention also provided a luminal valve for placing in a body lumen comprising at least four valve leaflets, the valve having a normally closed configuration in which the leaflets are engaged and an open configuration in which the leaflets are open. There may be at least five valve leaflets. There may be six valve leaflets.

In one case the valve is an esophageal valve. In one case the valve has an antegrade open configuration in which the valve leaflets are opened in response to an antegrade force to allow flow through the valve and a retrograde open configuration in response to a retrograde force which is substantially larger than the antegrade force.

The valve may comprise a valve body of polymeric material. The valve may comprise an outer support region. The valve may also have a main body region extending between the support region and the valve leaflets.

In one case the main body region is generally concave between the outer support rim and a region of co-aption of the valve leaflets.

In one embodiment the valve leaflets and at least portion of the main body region inverts to allow flow in the retrograde direction. Preferably, on reduction in retrograde forces the main valve region and the valve leaflets evert to the normally closed configuration.

In one case the valve leaflets have a region of co-aption and the valve body is reinforced at the region of co-aption. The valve body may be thickened at the region of co-aption.

The region of co-aption may extend for an axial length of at least 1 mm. The region of co-aption may extend for a depth of from 1 mm to 5 mm.

In one embodiment the support rim of the valve body is reinforced. The support rim of the valve may be thickened.

In one embodiment the valve comprises three valve leaflets.

In another embodiment the valve comprises six valve leaflets.

The invention also provides an esophageal valve comprising a support structure for the valve.

The valve may be mounted to the support structure.

In one case the valve rim is sutured to the support structure. Alternatively or additionally the valve rim is bonded to the support structure.

In one embodiment the support structure comprises a luminal prosthesis.

In one case the luminal prosthesis extends proximally of the valve.

In another case the luminal prosthesis extends distally of the valve.

In one embodiment the luminal prosthesis extends proximally and distally of the valve.

The luminal prosthesis may have a coating and/or a sleeve thereon. The coating or sleeve may be on the outside of the luminal prosthesis. Alternatively the coating or sleeve is on the inside of the luminal prosthesis.

In one embodiment a pressure of 0.7 mm Hg in the antegrade direction is sufficient to allow a flowrate of 140 ml/min.

In one embodiment the retrograde force required to open the valve is a pressure of greater than 15 mm Hg and less than 40 mm Hg.

In one embodiment the polymeric material is stable to gastric fluid for at least 3 months, for at least 4 months, for at least 5 months, for at least 6 months, for at least 7 months, for at least 8 months, for at least 9 months, for at least 10 months, for at least 11 months, or for at least one year.

In one case the polymeric material takes up less than about 5%, less than about 10%, less than about 15%, less than about 20%, less than about 25%, or less than about 30% by weight of water at equilibrium.

In one case the polymeric material of the valve body has a % elongation of from 50% to 3000% or 200% to 1200%.

In one case the polymeric material of the valve body has a tensile strength of from 0.01 to 5 MPa or about 0.1 to 1.0 MPa, or about 0.25 to 0.5 MPa.

In one embodiment the polymeric material has a Young's Modulus of about 0.01 to 0.6 MPa, or about 0.1 to about 0.5 MPa.

In one embodiment the polymeric material of the valve body has a density of from $0.1 \text{ g/cm}^3$ to $1.5 \text{ g/cm}^3$, or 0.3 to 1.2 $\text{g/cm}^3$, or 0.8 to 0.9 $\text{g/cm}^3$, or 0.5 to 0.6 $\text{g/cm}^3$.

In one embodiment the distance between the proximal end of the support region of the valve body and the distal end of the valve leaflets is less than 50 mm, or less than 40 mm, or less than 30 mm, or less than 25 mm, or less than 20 mm, or less than 15 mm.

In one case the polymeric material of the valve body is of an elastic material.

In another case the polymeric material of the valve body is of a viscoelastic material.

In one embodiment the polymeric material of the valve body comprises a foam. The polymeric material of the valve body may comprise an open cell foam.

In one embodiment the polymeric material of the valve body comprises a polyurethane foam.

In one embodiment the esophageal valve is adapted to be mounted to a pre-deployed support structure, for example an esophageal luminal prosthesis such as a stent.

The invention also provides a valve having:
  a normally closed configuration in which the valve is closed;
  an open configuration in which the valve is opened for flow through the valve; and
  a support for the valve, the support being adapted for mounting to a pre-deployed luminal prosthesis intermediate a proximal end and a distal end of the predeployed luminal prosthesis.

In one case the valve is an esophageal valve for mounting to an esophageal stent.

In one embodiment the valve support region is sutured to the support structure.

The valve support region may be bonded to the support structure.

The luminal prosthesis may extend proximally of the valve. The luminal prosthesis may extend distally of the valve. The luminal prosthesis may extend proximally and distally of the valve.

In one case the luminal prosthesis has a coating and/or sleeve thereon. The coating or sleeve may be on the outside of the luminal prosthesis. Alternatively or additionally the coating or sleeve is on the inside of the luminal prosthesis.

In one embodiment the valve is adapted to be mounted to a pre-deployed esophageal luminal prosthesis such as an esophageal stent.

There may be a mounting means for mounting the valve to a pre-deployed esophageal luminal prosthesis. The mounting means may be provided on the valve.

In one case the mounting means comprises engagement means for engagement with a pre-deployed stent.

The valve may comprise a support structure. The support structure may taper outwardly or inwardly.

In one case the support structure is of generally uniform diameter along the length hereof In one embodiment the support structure comprises a scaffold. The support structure may comprise a stent-like structure.

The mounting means may be provided by the support structure. In one case the mounting means comprises protrusions extending from the support structure. The protrusions may be adapted to engage with a pre-deployed host esophageal luminal prosthesis.

In one embodiment the protrusion comprises a loop.

In one case the apicial tip of the protrusion is rounded.

The protrusions may be releasably engagable with a pre-deployed host esophageal luminal prosthesis.

There may be release means for releasing the valve from engagement with a pre-deployed host esophageal luminal prosthesis. The release means may comprise means for reducing the diameter of at least portion of the valve support structure.

In one case the release means comprises a drawstring extending around the valve support structure. A first drawstring may extend around a proximal end of the support structure. A second drawstring may extend around a distal end of the support structure.

In one embodiment the valve is mounted to the support structure. The valve may be sutured to the support structure. The valve may be bonded to the support structure. The valve may be adhesively bonded to the support structure.

In another case the mounting means comprises a surgical adhesive.

The invention also provides a method for providing a valve in a body passageway comprising the steps of:
  providing a valve mounted to a support structure;
  delivering the valve mounted to the support structure to a pre-deployed luminal prosthesis in the body passageway; and
  deploying the valve so that the valve is mounted to the luminal prosthesis.

In one embodiment the step of deploying the valve comprises engaging the valve support with the pre-deployed luminal prosthesis.

The valve support may be mechanically engaged with the pre-deployed luminal prosthesis.

In one case the valve support comprises a protrusion and the method comprises aligning the protrusion with an aperture in the endoluminal prosthesis and engaging the protrusion in the aperture.

In one embodiment the valve support is an expandable support and the method comprises loading the support onto a delivery catheter in a retracted form and the valve support is extendable on deployment.

The support may be self expandable or the support is expanded by an expanding means such as a balloon.

In one embodiment the method comprises the step of releasing the valve support from engagement with the luminal prosthesis.

The method may involve repositioning the valve support within the prosthesis. The method may comprise removing the valve from the prosthesis.

In one embodiment the body passageway is the esophagus and the valve is an esophageal valve for mounting to a pre-deployed esophageal stent.

In one case there is a support structure for the valve. The valve may be mounted to the support structure. The valve support region may be sutured to the support structure. Alternatively or additionally the valve support region is bonded to the support structure. In one case the support structure is overmoulded to the valve support region.

The support structure may comprise a luminal prosthesis.

In one embodiment the luminal prosthesis extends proximally of the valve. The prosthesis may comprise a self expanding plastics mesh. The prosthesis may apply a radial force of less than 1.9 kPa.

In one embodiment there are anchors for mounting the prosthesis in situ. The anchors may be adapted to extend through the mesh of the prosthesis.

In one case the prosthesis is adapted to be anchored to the cardia.

In one embodiment the length of the valve from the proximal end of the support region to the distal end of the valve leaflets is less than 50 mm, less than 40 mm, less than 30 mm.

The length of the valve may be approximately the same as the outer diameter of the support region of the valve. The length of the valve may be approximately 23 mm.

In another aspect the invention comprises a method for treating gastroesophageal reflux disease comprising providing a valve of the invention and placing the valve at a desired location. The desired location may be across the lower esophageal sphincter. In one case the valve leaflets are located distal to the end of the esophagus. In one embodiment the valve is provided with a support structure and the method comprises mounting the support structure at the desired location. The method may comprise anchoring the support structure to the body wall at the desired location. In one case the method comprises anchoring the support structure to the cardia.

BRIEF DESCRIPTION OF THE DRAWINGS

The invention will be more clearly understood from the following description thereof given by way of example only, in which:

FIG. 23 is an isometric view of a esophageal prosthesis;

FIG. 24 is an elevational view of the valve of FIGS. 1 to 22 being mounted to and in position on the prosthesis of FIG. 23;

FIG. 25 is another view of the valve mounted in a prosthesis;

FIGS. 26 and 27 are isometric views of a sleeved or coated esophageal prosthesis;

FIG. 29 is an elevational view of part of the prosthesis of FIG. 28 in position in the esophagus;

FIG. 35 is an elevational view of a luminal prosthesis with a valve and associated support structure in place;

FIG. 36 is an enlarged view of the luminal prosthesis and valve support structure of FIG. 35;

FIGS. 37 and 38 are enlarged views of one mounting detail of a valve support structure to a luminal prosthesis;

FIG. 47 is an elevational view of a valve according to another embodiment of the invention;

FIG. 48 is an enlarged view of a detail of the support structure of the valve of FIG. 47;

FIG. 51 is an elevational view of a prosthesis with the valve of FIGS. 49 to 50 in situ;

FIG. 52 is an enlarged view of a detail of the engagement of the valve support structure of FIGS. 47 to 51 engaged in the mesh of the prosthesis;

FIG. 53 is an enlarged view of part of the luminal prosthesis and valve support structure of FIG. 52.

FIGS. 56 to 61 are elevational views of steps involved in deploying the valve of FIG. 55 into a pre-deployed esophageal luminal prosthesis of FIG. 54;

FIG. 62 is an elevational view of the valve of FIG. 55 deployed in the luminal prosthesis of FIG. 61;

FIG. 63 is an elevational view similar to FIG. 62 with the valve being removed from the deployed prosthesis;

DETAILED DESCRIPTION

Figure 2:
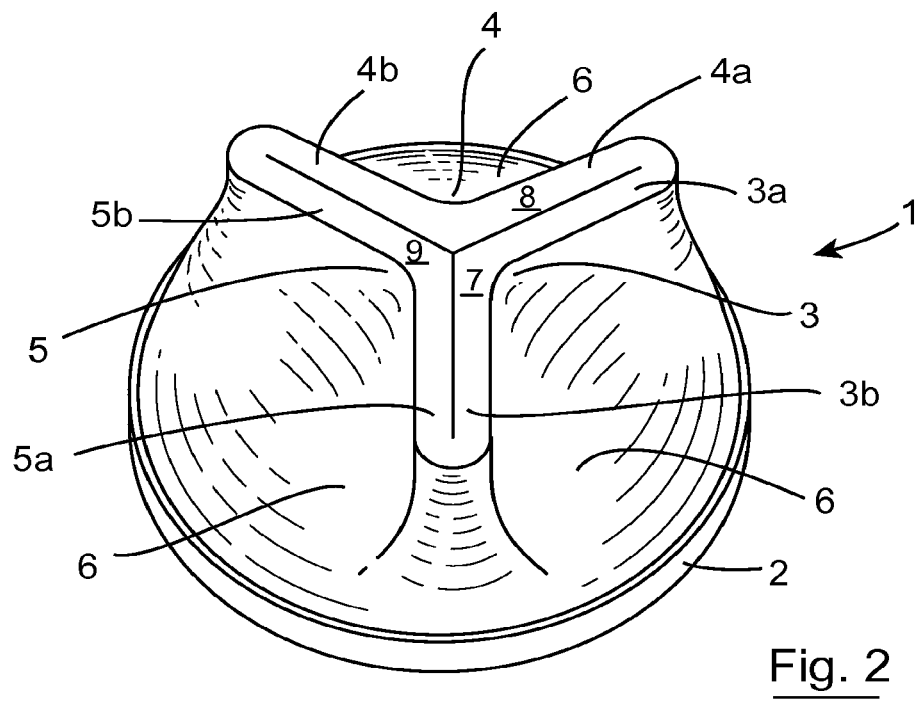
FIG. 2 is an isometric view (from below) of the esophageal valve.

Referring to the drawings and initially to FIGS. 1 to 22 thereof there is illustrated an esophageal valve 1 which can open automatically in the antegrade direction (food intake) and in the retrograde direction (from the stomach to the mouth).

The valve 1 comprises a polymeric valve body having a proximal outer support region with a rim 2, at least three valve leaflets 3, 4, 5, and a main body region 6 extending between the support rim 2 and the valve leaflets 3, 4, 5. The valve leaflets 3, 4, 5 extend inwardly and distally and terminate at distal end faces 7, 8, 9 respectively. The leaflets each 3, 4, 5 have legs a, b which extend at an included angle of 120° to each other. The adjacent pairs of legs 3a; 4a; 4b; 5b; 5a; 3b; co-apt to close the gap between the valve leaflets when the valve is in the normally closed configuration.

The valve 1 has three configurations. The first configuration is a normally closed configuration in which the valve leaflets 3, 4, 5 co-apt to close the valve. The second configuration is an antegrade open configuration in which the valve leaflets 3, 4, 5 are opened such that the leaflet leg pairs 3a; 4a; 4b; 5b; 5a; 3b are opened and spaced-apart in response to an antegrade force F1 to allow flow through the valve. The third configuration is a retrograde open configuration in response to a retrograde force which is substantially larger than the antegrade force F2.

Figure 12:
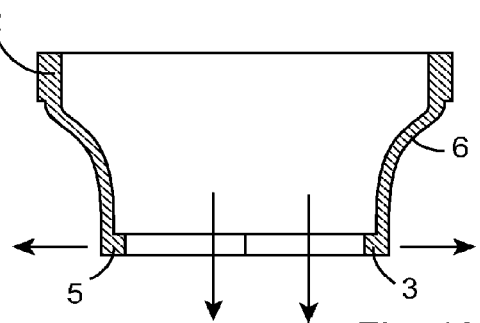
FIG. 12 is a cross sectional view of the valve in an open configuration in response to an antegrade force.
Figure 13:
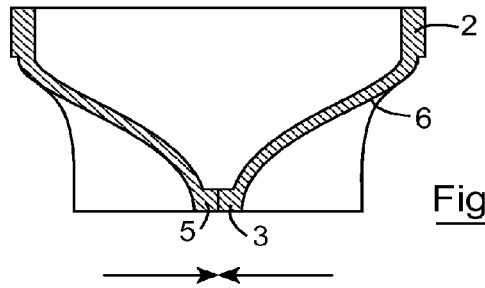
FIG. 13 is a cross sectional view of the valve returned to the closed configuration after opening to antegrade flow.
Figure 14:
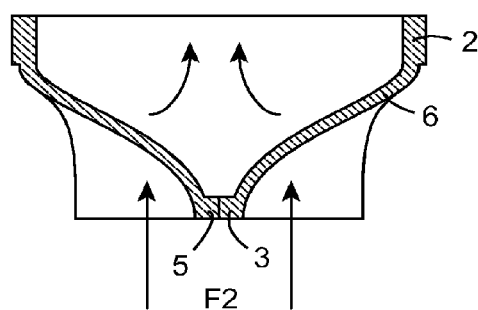
FIG. 14 is a cross sectional view of the valve in a normally closed configuration with a retrograde force applied.
Figure 18:
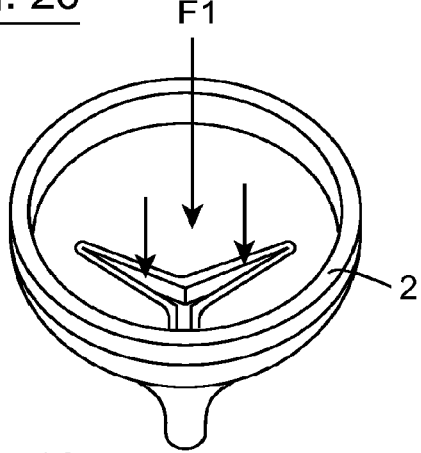
FIG. 18 is an isometric view of the valve in a partially open configuration in response to an antegrade force.
Figure 19:
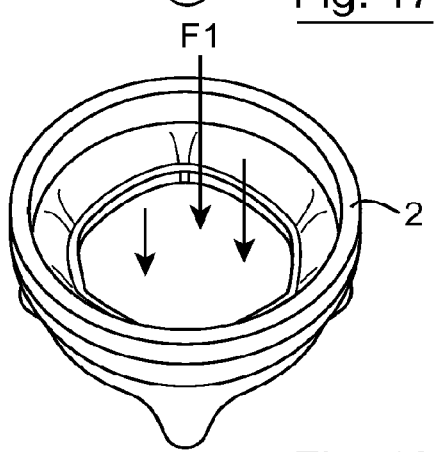
FIG. 19 is an isometric view of the valve in a fully open configuration in response to antegrade force.

The various configurations of the valve 1 are illustrated in FIGS. 11 to 22. In the first or normally closed configuration (FIGS. 11, 17) the valve leaflets 3, 4, 5 co-apt. When an antegrade force F1 is applied to the valve leaflets 3, 4, 5 the leaflet legs pairs 3a; 4a; 4b; 5b; and 5a; 3b open to allow antegrade flow to pass (FIGS. 12, 19). FIG. 18 illustrates a partially open configuration in response to antegrade flow. When the antegrade force F1 is removed the leaflets 3, 4, 5 return to the closed position under the inherent biasing of the polymeric material of the valve body (FIG. 13).

Figure 15:
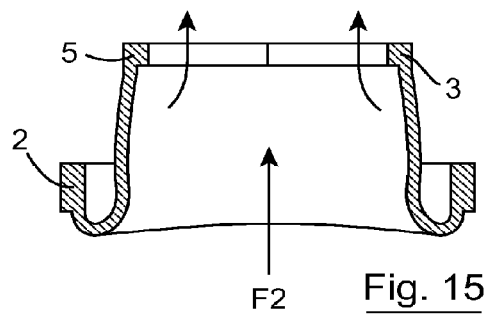
FIG. 15 is a cross sectional view of the valve in an open configuration in response to retrograde force.
Figure 16:
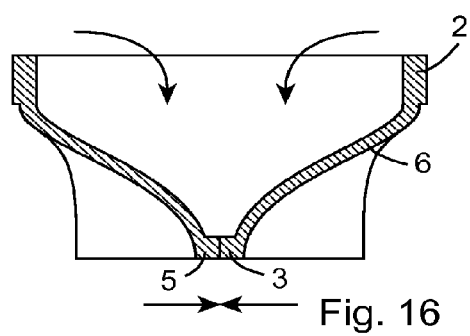
FIG. 16 is a cross sectional view of the valve returned to the closed configuration after opening to retrograde flow.
Figure 20:
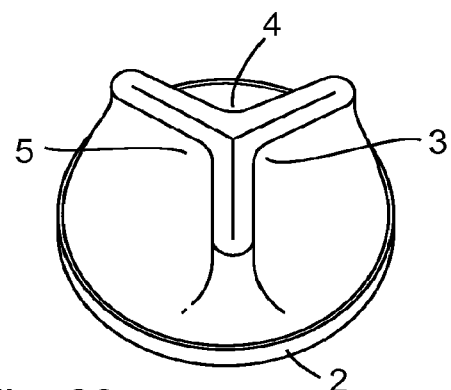
FIG. 20 is an isometric view (from below) of the valve in a normally closed configuration.
Figure 17:
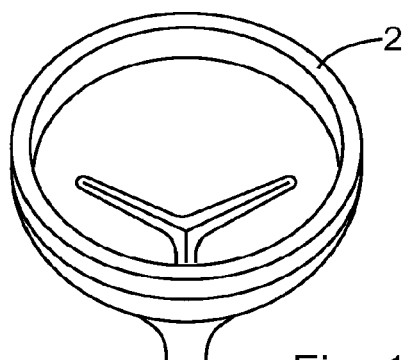
FIG. 17 is an isometric view (from above) of the valve in a normally closed configuration.
Figure 21:
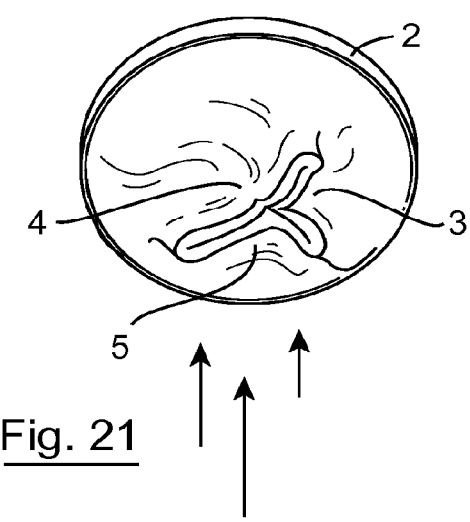
FIG. 21 is an isometric view of the valve moving towards an open configuration in response to a retrograde force.
Figure 22:
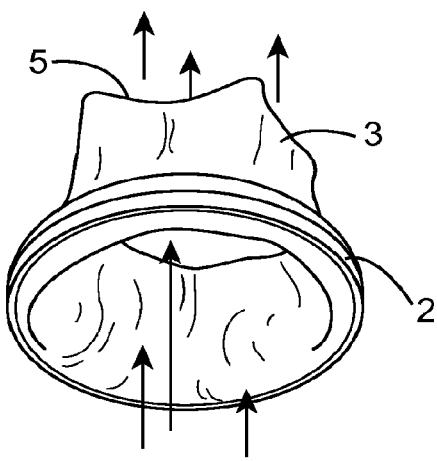
FIG. 22 is an isometric view of the valve in a fully open configuration permitting retrograde flow.
Figure 28:
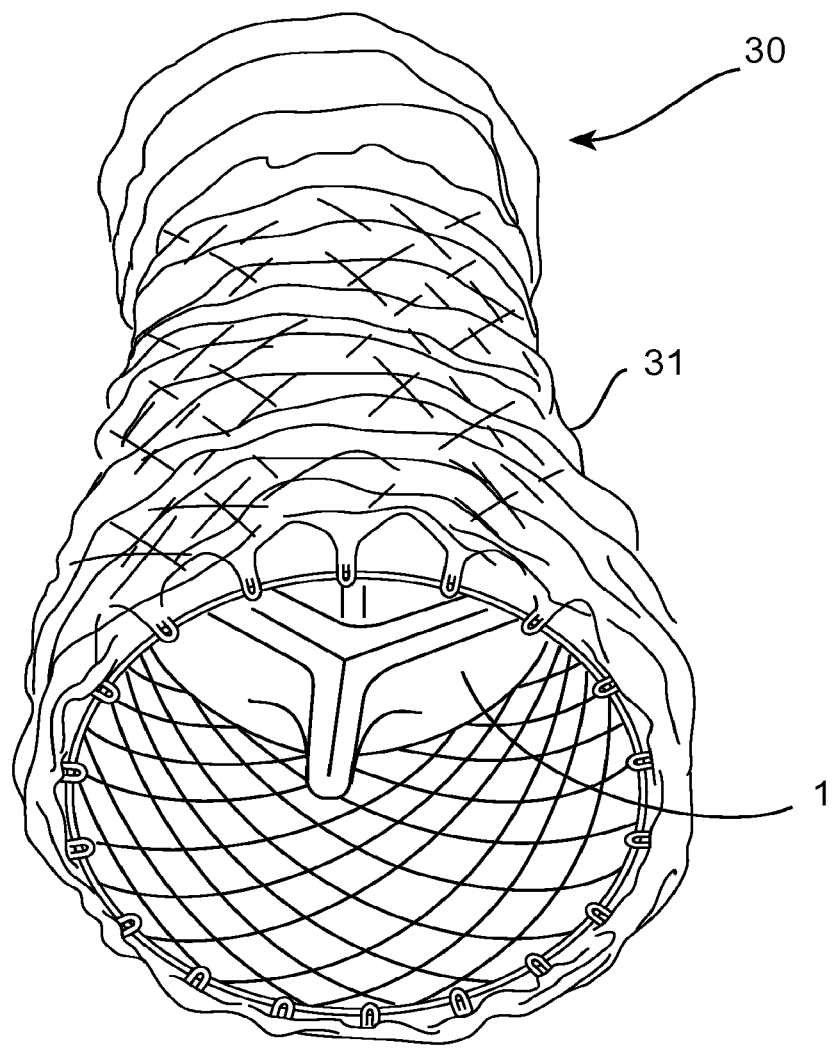
FIG. 28 is an isometric view of the prosthesis of FIGS. 26 and 27 with a valve of FIGS. 1 to 22 in position.

When a retrograde force F2 is applied to the valve body. This force initially pushes the valve leaflets 3, 4, 5 against one another and if the pressure is greater than a set value, the valve body will invert. The start of inversion is illustrated in FIG. 21. When the valve is fully opened in response to retrograde force the valve main body (and the leaflets 3, 4, 5) extend proximally (upwardly) as illustrated in FIGS. 15 and 22. This allows retrograde flow to pass through the valve. When the retrograde force F2 is removed the valve main body will return to the original configuration by everting in response to the biasing of the polymeric material to return to the normally closed configuration with the valve leaflets extending distally as illustrated in FIGS. 16 and 20.

The valve leaflets 3, 4, 5 are reinforced in the region of co-aption. In this case, this is achieved by a local thickening of the polymeric material in this region. Similarly the support rim 2 is reinforced by a local thickening of the polymeric material.

The region of co-aption of the valve leaflets 3, 4, 5 has an axial extent which is typically from 1 to 5 mm. This ensures positive co-aption of the leaflets across a significant interfacial area when the valve is in the normally closed configuration. The thickness of the leaflets at the region of co-aption is typically between 0.1 mm and 10 mm.

The valve body has a generally concave outer face and a generally convex inner face.

The valve 1 is a two-way valve. Different forces are required to open the valve from the proximal or distal directions. The valve 1 requires very little force to open in the antegrade direction, a pressure of 0.7 mm Hg in the antegrade direction is sufficient to allow a flowrate of 140 ml/min. In the retrograde direction the valve 1 can hold pressures of between 15 mm Hg and 40 mm Hg and higher. By varying the properties (such as density) of the material of the valve the valve can be tailored to accommodate varying yield pressures. The valve accomplishes this by controllably inverting when placed under pressure in the retrograde direction.

The valve 1 of the invention returns to its original working position after being fully opened in the retrograde direction. This is accomplished without damaging the working valve.

When the valve is opened by food passing in the antegrade direction the leaflets open. The outer face of the valve has a greater resistance to change in shape and thus the force required to open main body in the retrograde direction is higher.

The important characteristics influencing the functioning of the valve are the leaflet legs that impinge on one another. By varying the geometry and length of the leaflets 3, 4, 5 the valve 1 can be made to open in the retrograde direction at different pressures. Opening in the antegrade direction is somewhat less dependant on the geometry of the leaflets and more dependant on the elasticity and density of the material the device is made from. Additionally, the overall diameter and the diameter to which the leaflets open influence the opening force in both directions.

Because the stomach tends to have a slightly higher pressure than the oesophagus (the difference on average being approximately 12 mm Hg), a closed valve will experience this pressure at its distal surface. This distal pressure can ammeliorate the closing of a distally extending or tapering surface. However, previous examples of valves in the literature have relied on smooth surfaces to take advantage of this gastric pressure differential. Thus the only means of maximising the force generated by the gastric pressure was to increase the length of the distally extending or tapering surface. This in turn gave rise to problems associated will elongate structures becoming blocked with antegrade food flow and retrograde flow. The current invention teaches a method of retaining the short length of the valve structure and maximising the force generated by the gastric pressure through an increase in the surface area to length ratio.

This is achieved by increasing the surface area of the distal surface of the valve by introducing pleats or folds (leaflets).

The valve may be of any suitable biocompatible polymeric material. It may be of a biocompatible polymeric material having properties which allow the valve to function as described.

The materials used for the production of this valve have a % elongation between 50% and 3000%. The material also has a tensile strength of between 0.01 and 5 MPa. Additionally the material could have an antimicrobial action to prevent colonisation when in-vivo. Additionally the material can be elastic or viscoelastic and can optionally be an open cell foam. The density of the material should be between 0.1 g/cm3 to 1.5 g/cm3.

The valve of the invention may be mounted to any suitable luminal prosthesis, especially an esophageal prosthesis or stent. The rim 2 of the valve provides a mounting ring for mounting within the stent 20, for example, the valve 1 may be mounted to the stent by suturing the rim 2 to the stent mesh using sutures 21 as illustrated in FIGS. 24 and 25.

The stent may be of any suitable type. An uncoated or unsleeved stent 20 is illustrated in FIGS. 23 to 25. Alternatively, if it is desired to prevent tissue ingrowth a stent 30 having a sleeve 31 may be used (FIGS. 26 to 29). In this case the sleeve 31 is external of the stent. In other cases there may alternatively or additionally be an internal sleeve. Further, the stent may have a coating.

A valve such as described above may also be placed into a pre-deployed luminal prosthesis. For example, the valve may be an esophageal valve for placement into a pre-deployed stent in the esophagus.

Figure 31:
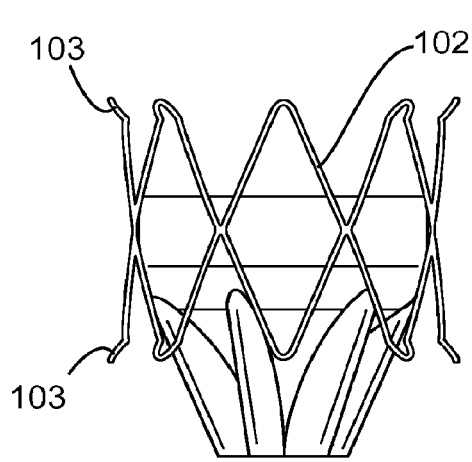
FIG. 31 is an elevational view of the valve of FIG. 30.
Figure 30:
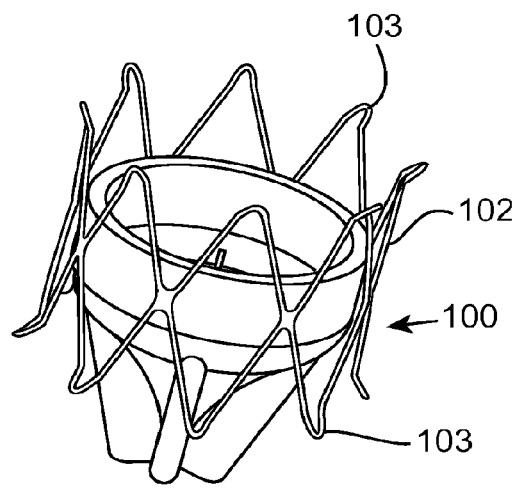
FIG. 30 is an isometric view of a valve according to another embodiment of the invention.

In one case a valve 100 may have a co-axial support structure or scaffold 102 is shown in FIGS. 30 and 31. The scaffold 102 is designed to engage with any suitable esophageal stent 140 as illustrated in FIG. 35. The mechanism of engagement can be by protrusions which may for example be proximal and/or distal apices 103 of the scaffold 102 which engage into the mesh of the existing pre-deployed stent 140. Alternatively or additionally, the scaffold 102 may have features 150 designed to hook onto the inside of the struts of an esophageal stent as illustrated in FIGS. 37 and 38.

Figure 33:
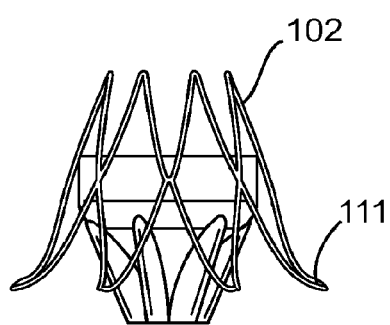
FIG. 33 is an elevational view of the valve of FIG. 32.
Figure 32:
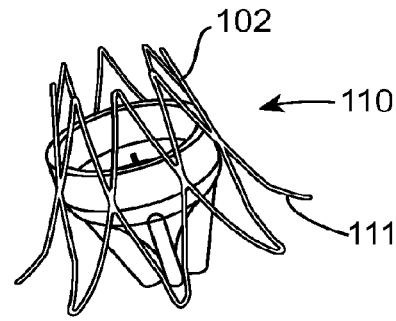
FIG. 32 is an isometric view of another valve according to the invention with a distally outward tapering support structure.

Referring to FIGS. 32 and 33 there is illustrated a valve 110 according to another embodiment of the invention in which the support structure or scaffold 102 tapers distally outwardly so that distal apices 111 of the scaffold engage with the mesh of the existing pre-deployed host stent 140.

Figure 34:
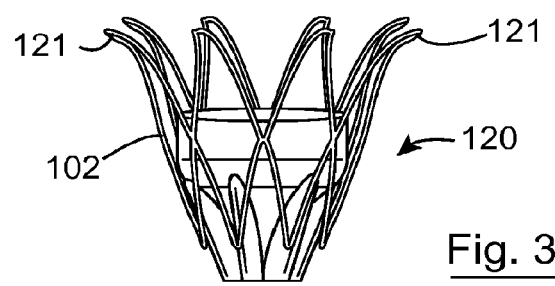
FIG. 34 is an isometric view of another valve according to the invention with a distally inward tapering support structure.
Figures 39, 40, 41:
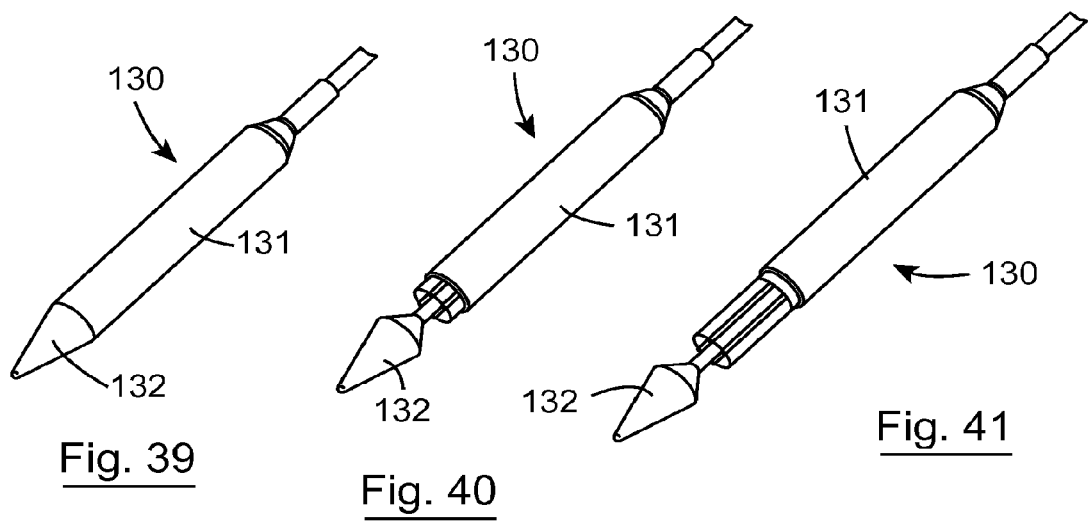
FIGS. 39 to 43 are views of a valve being deployed from a delivery catheter.
Figures 42, 43:
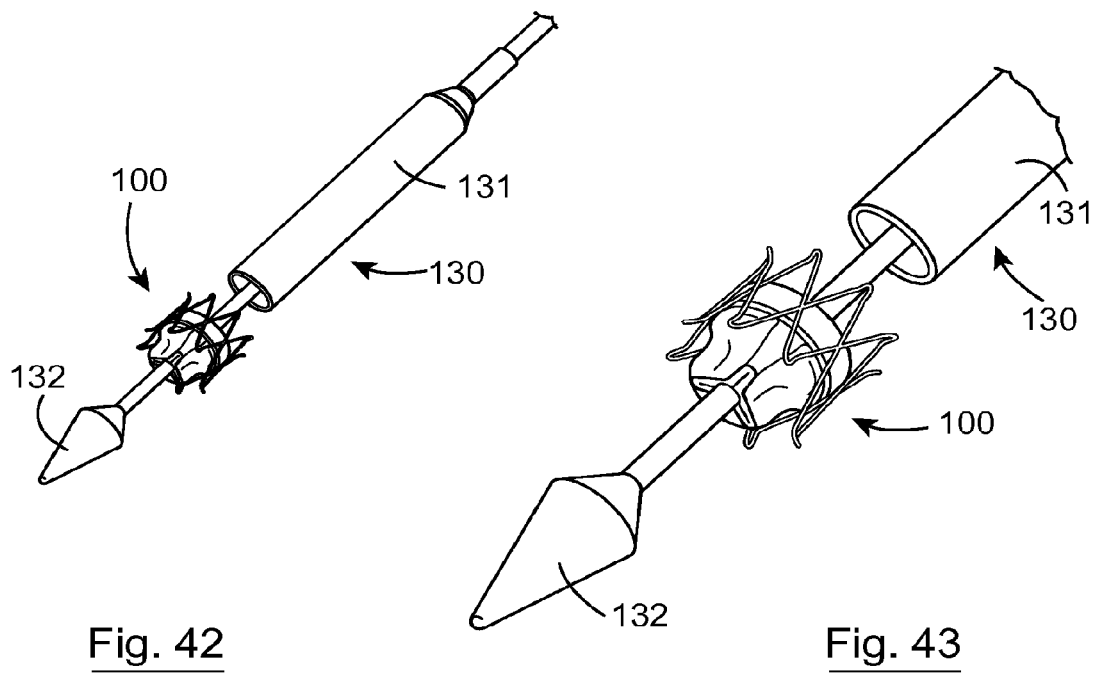

Referring to FIG. 34 there is illustrated another valve 120 according to the invention in which the support structure or scaffold 102 tapers distally inward so that proximal apices 121 of the scaffold 102 engage with the mesh of an existing pre-deployed stent 140.

The radial force of the scaffold 102 may exert enough friction to hold the valve in place without the necessity for protrusion. In another embodiment a surgical adhesive may be used to secure the retrofitted valve into place.

Referring to FIGS. 39 to 43 a valve 100 is loaded into a delivery system 130 for deployment. The outer diameter of the delivery system 130 is smaller than the inner diameter of a pre-deployed esophageal stent 140. The delivery system 130 in this case comprises a delivery catheter having a distal pod 131 in which a valve is housed in a contracted configuration. The catheter has a tapered distal tip 132 to avoid snagging on a pre-deployed stent 140. The pod 131 is axially movable relative to the tip 132 to release the valve from the pod 131.

Figure 44:
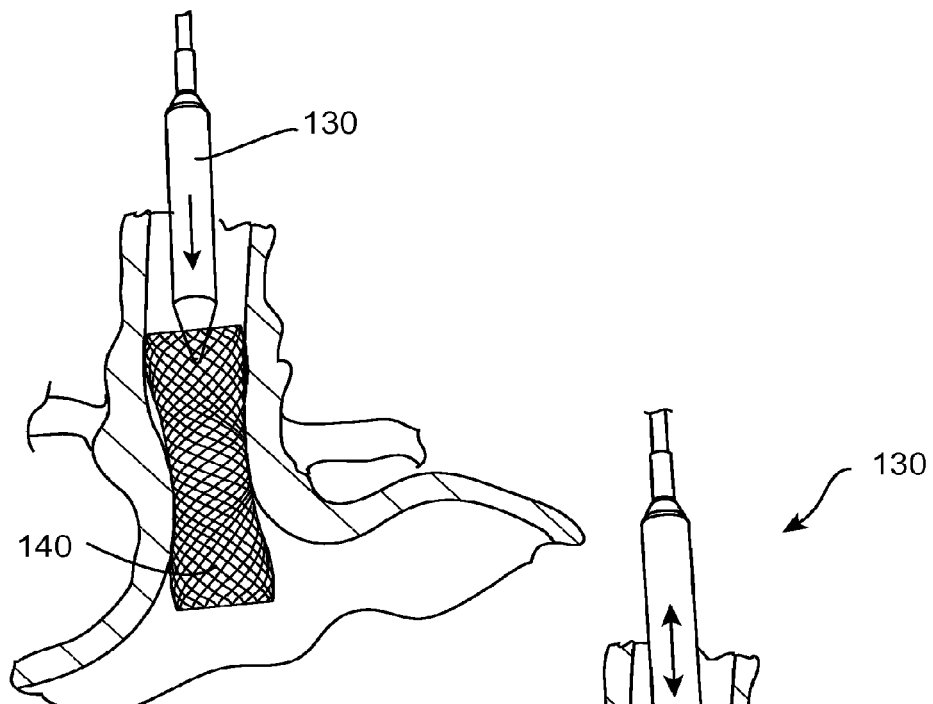
FIGS. 44 to 46 are views of a luminal prosthesis in place in the esophagus with a valve being deployed in the lumen of the luminal prosthesis.
Figure 45:
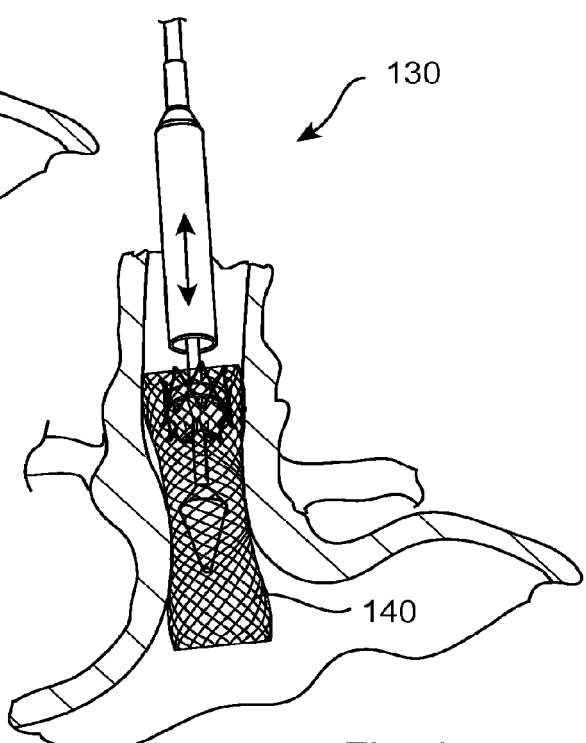
Figure 46:
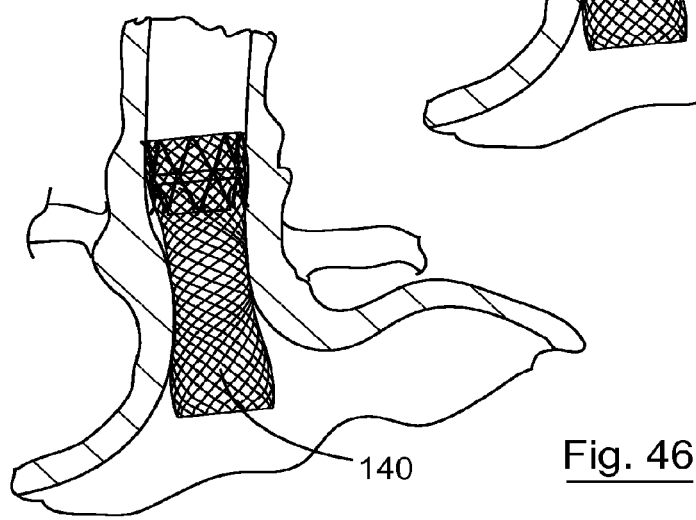

The delivery system 130 is used to deliver the valve to a pre-deployed stent 140 as illustrated in FIG. 44. The stent 140 has a mesh and the scaffold of the valve is adapted to engage with the mesh of the pre-deployed stent 140 on release of the valve from the delivery catheter as illustrated particularly in FIGS. 45 and 46.

Referring to FIGS. 35 to 38 there is illustrated an idealised stent 140 with a valve support scaffold 102 in situ. Details of a valve are omitted from these drawings for clarity. In this case the scaffold 102 is located at the upper proximal end of the stent. In this case the scaffold 102 has hook-like members 150 for engagement with the mesh of the stent 140 as illustrated in FIGS. 37 and 38. The interengagement between the stent 140 and the scaffold 102 ensures that the scaffold 102 and hence the valve which is fixed to it is retained in position and provides an anti-roximal migration mechanism.

In the cases illustrated the valve supporting scaffold 102 is of a self expanding material such as a shape memory material, for example Nitinol. The valve and scaffold are loaded into the delivery catheter pod 131 in a compressed/reduced diameter configuration. When the constraint of the pod 131 is removed at the deployment site, the scaffold and valve self expand to the normal configuration in which the scaffold is engaged with the pre-deployed host stent 140. In some arrangements the scaffold may be of an expensile material which is expanded by an expander such as a balloon or the like.

Figures 49, 50:
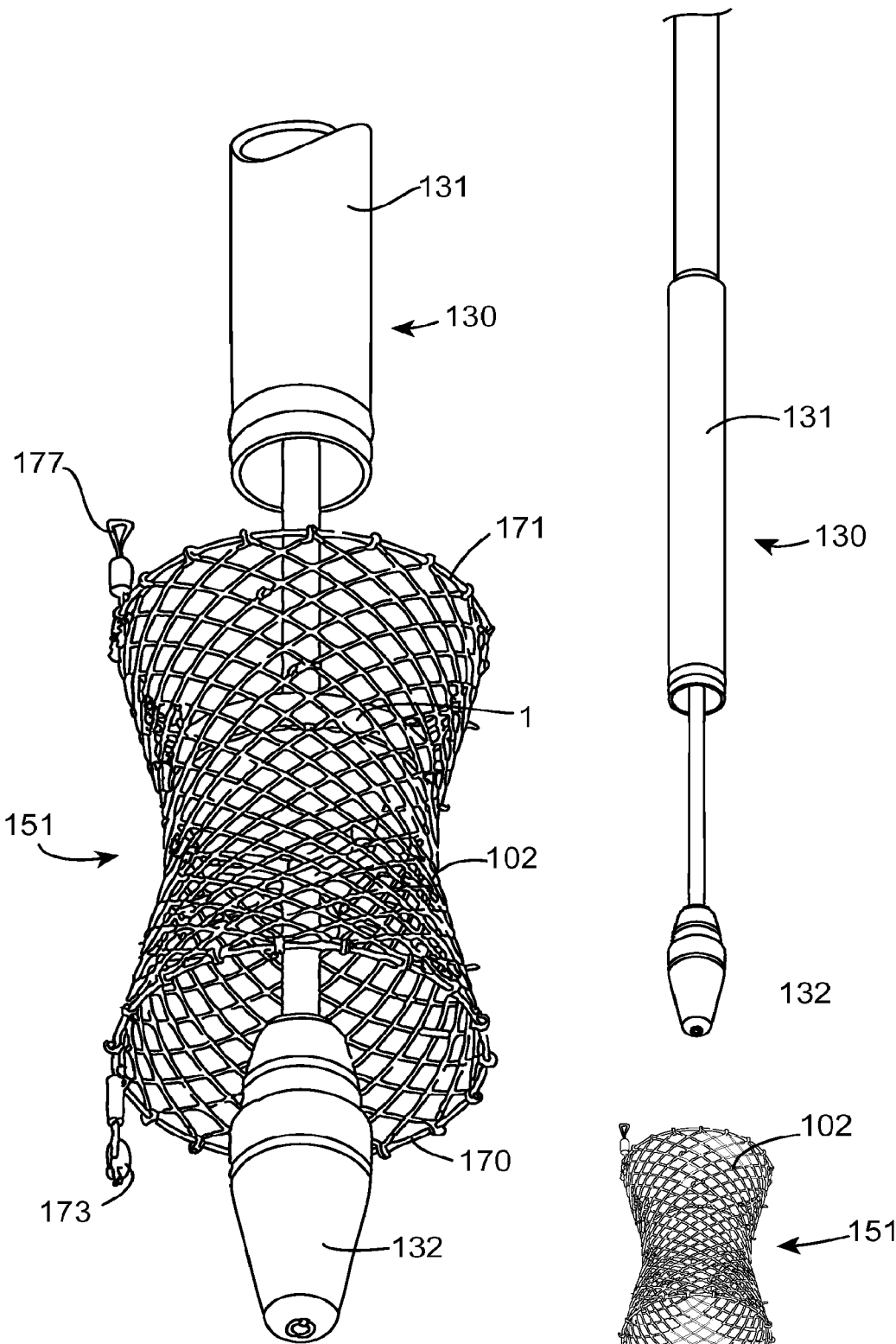
FIGS. 49 and 50 are isometric views of the valve of FIGS. 47 and 48 being deployed from a delivery catheter.
Figures 54, 55:
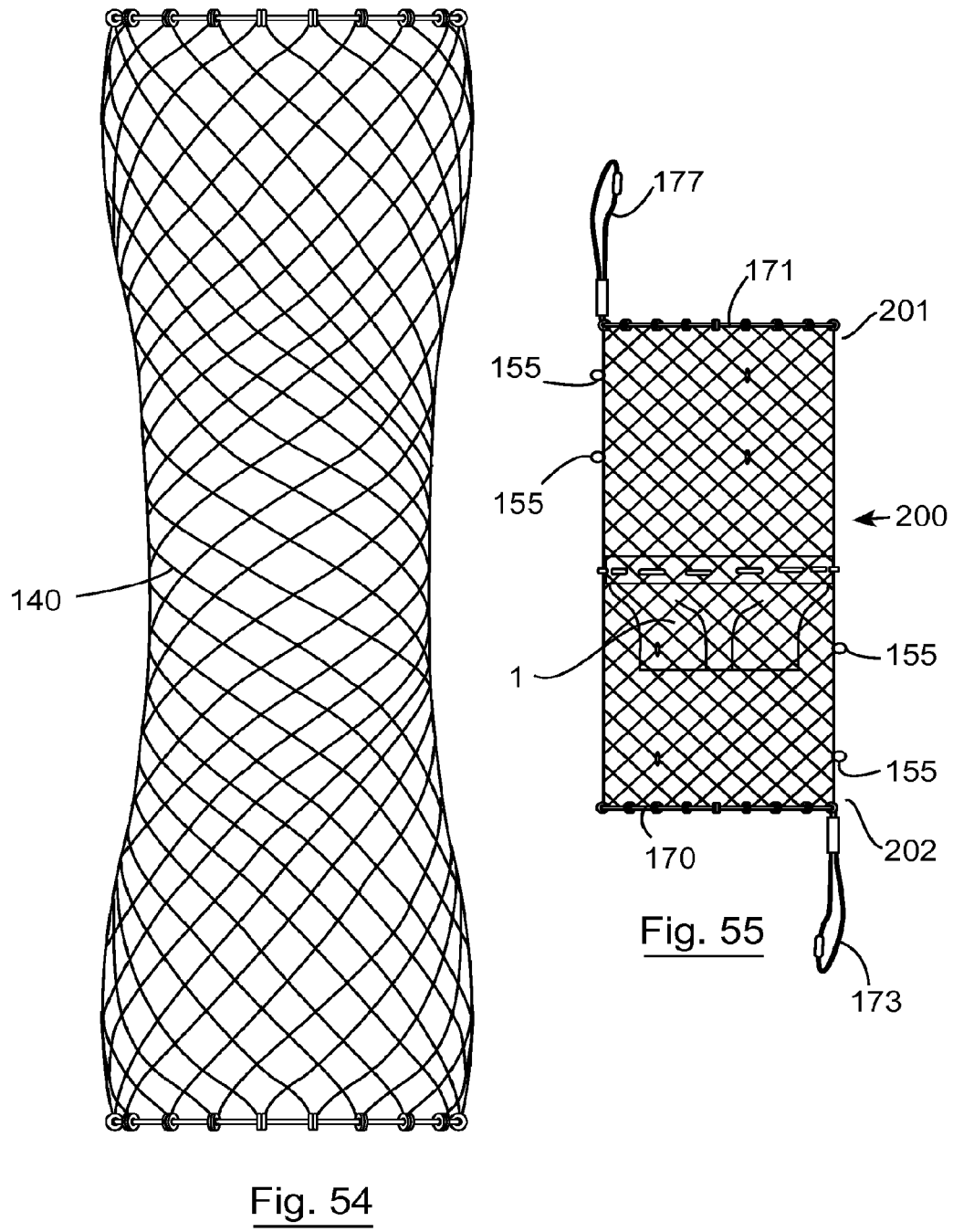
FIG. 54 is an elevational view of an esophageal luminal prosthesis.
FIG. 55 is an elevational of an esophageal valve of the invention.
Figure 64:
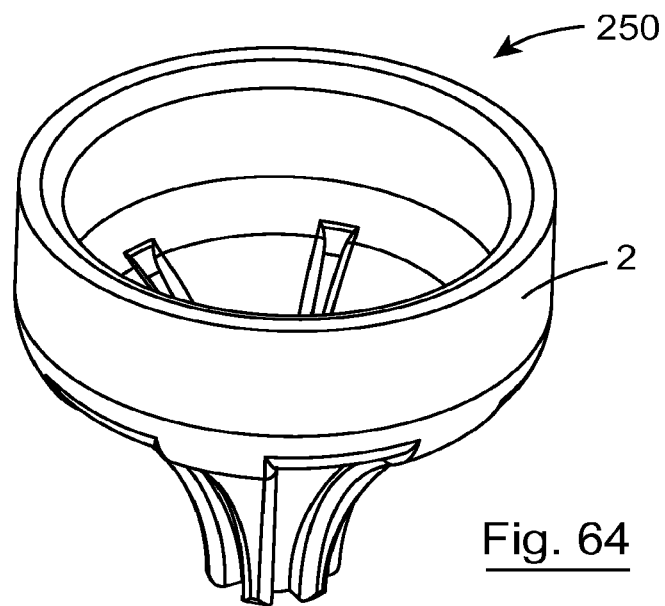
FIGS. 64 and 65 are isometric view of another valve according to the invention.
Figure 65:
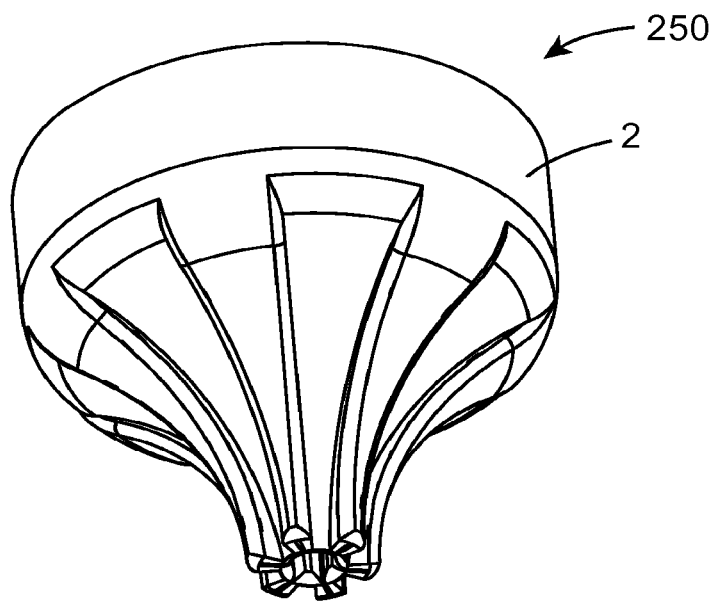
Figure 66:
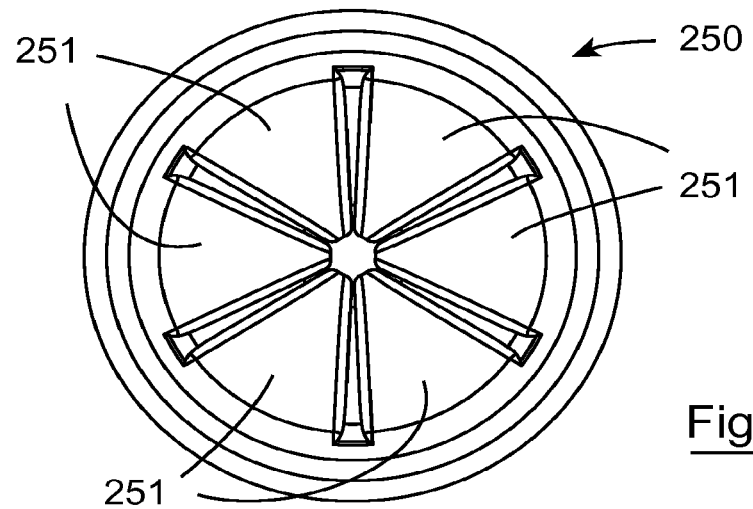
FIG. 66 is a top plan view of the valve of FIGS. 64 and 65.
Figure 67:
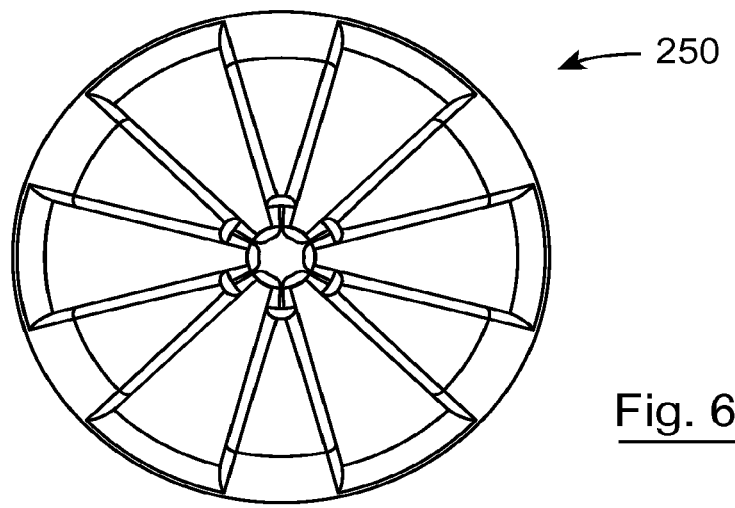
FIG. 67 is an underneath plan view of the valve of FIGS. 64 and 65.
Figure 68:
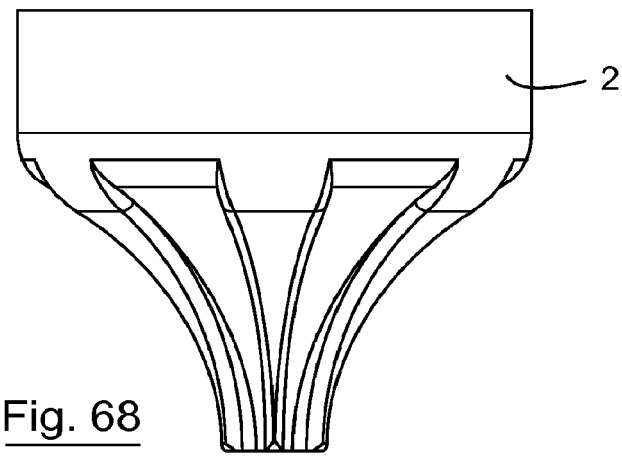
FIG. 68 is an elevational view of the valve of FIGS. 64 and 65.
Figure 69:
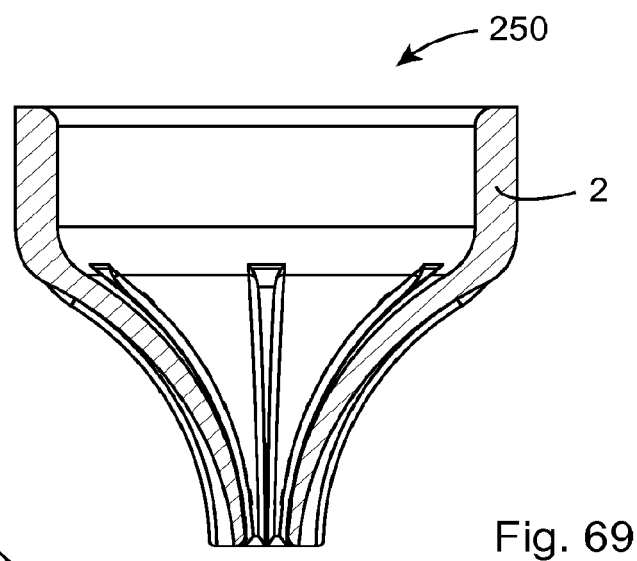
FIG. 69 is a cross sectional view of the valve of FIGS. 64 and 65.
Figure 70:
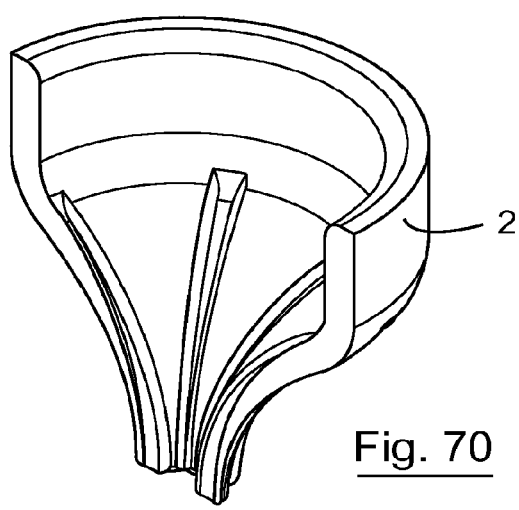
FIG. 70 is a cut-away isometric view of the valve of FIGS. 64 and 65.

Referring to FIGS. 47 to 50 there is illustrated another valve device 151 according to the invention which is similar to that described above and like parts are assigned the same reference numerals. In this case the valve 1 is housed within a support structure or scaffold 102 and is placed into the lumen of a stent 140 as illustrated in FIGS. 51 to 53. The support structure may comprise a relatively short length (typically 40 mm) of a mesh made from a shape memory material such as Nitinol. The mesh may be formed by laser cutting and/or may be of woven construction. Deployment into the lumen of the host stent 140 is via self expansion from a radially collapsed state within a delivery catheter 130 as shown in FIGS. 49 and 50. The device 151 is held in place within the stent 140 by means of specific interaction mechanisms that increase the axial friction of the support structure 102. FIGS. 51 to 53 illustrate the interaction with the host stent 140. In this embodiment the support structure 102 has a series of loops or protrusions 155 extending perpendicularly from its surface. These protrusions 155 engage with the structure of any host stent 140 by interlocking with the existing mesh as shown in FIGS. 52 and 53. The apical tip of each protrusion 155 is in this case rounded or designed so as to be non-traumatic to any tissue that may come into contact with the protrusion 155. The intrinsic radial force of the support structure 102 as well as the flexural strength of the protrusions 155 interact to effect the retention performance of the support structure 102. Thus the stiffness or flexural strength of the protrusion 155 and the radial force of the support structure 102 may be modified to change the interlocking capability and retention performance of the device.

The valve device 151 is also readily radially collapsible by distal and proximal drawstrings 170, 171. The distal drawstring 170 passes through eyelets 172 mounted to the support structure 102 at the distal end of the valve device 151. The distal drawstring 170 has an accessible pull string 173 which, on pulling, pulls the drawstring 171 inwardly and thus reduces the diameter of the distal end of the support structure 102. Similarly the proximal drawstring 171 passes through eyelets 175 mounted the support structure 102 at the proximal end of valve device 151. The proximal drawstring 171 has an accessible pull string 177 which, on pulling, pulls the drawstring 171 inwardly and thus reduces the diameter of the proximal end of the support structure 102. The pull strings 173, 177 can be readily gripped using a suitable instrument such as a grasper to draw the proximal and distal ends of the support structure 102 inwardly for ease of removal of the valve device 151.

Referring to FIGS. 54 to 63 there is illustrated another valve device 200 according to the invention which is similar to that described above and like parts are assigned the same reference numerals. In this case the valve 1 is housed within a support structure or scaffold 102 and is placed into the lumen of a stent 140 as illustrated in FIGS. 59 to 62. The support structure 102 may comprise a relatively short length (typically 40 mm) of a mesh made from a shape memory material such as Nitinol. The mesh may be formed by laser cutting and/or may be of woven construction. Deployment into the lumen of the host stent 140 is via self expansion from a radially collapsed state within a delivery catheter 130 as shown in FIGS. 56 to 61. The device 200 is held in place within the stent 140 by means of specific interaction mechanisms that increase the axial friction of the support structure 102. FIG. 62 illustrates the interaction with the host stent 140. In this embodiment the support structure 102 has a series of loops or protrusions 155 extending perpendicularly from its surface. These protrusions 155 engage with the structure of any host stent 140 by interlocking with the existing mesh as shown in FIG. 62. The apical tip of each protrusion 155 is in this case rounded or designed so as to be non-traumatic to any tissue that may come into contact with the protrusion 155. The intrinsic radial force of the support structure 102 as well as the flexural strength of the protrusions 155 interact to effect the retention performance of the support structure 102. Thus the stiffness or flexural strength of the protrusion 155 and the radial force of the support structure 102 may be modified to change the interlocking capability and retention performance of the device.

The valve device 200 is also readily radially collapsible by distal and proximal drawstrings 170, 171. The distal drawstring 170 passes through eyelets 172 mounted to the support structure 102 at the distal end of the valve device 200. The distal drawstring 170 has an accessible pull string 173 which, on pulling, pulls the drawstring 171 inwardly and thus reduces the diameter of the distal end of the support structure 102. Similarly the proximal drawstring 171 passes through eyelets 175 mounted the support structure 102 at the proximal end of valve device 200. The proximal drawstring 171 has an accessible pull string 177 which, on pulling, pulls the drawstring 171 inwardly and thus reduces the diameter of the proximal end of the support structure 102. The pull strings 173, 177 can be readily gripped using a suitable instrument such as a grasper to draw the proximal and distal ends of the support structure 102 inwardly for ease of removal of the valve device 200.

It will be noted that in the case of this device 200 the diameter of the support scaffold is relatively uniform and the proximal and distal ends 201, 202 of the device 200 are not tapered. We have found that the interengagement of the rounded protrusions 155 in interstices defined in the mesh structure of the stent 140 is sufficient to retain the device 200 in position in the stent 140. Typically, the diameter of the expanded support structure 102 will be slightly larger, for example 1 to 5% larger than that of the host stent 140 at the desired deployment location to assist in maintaining the scaffold 102 in situ.

In some cases, as illustrated in FIG. 63 the devices of the invention such as the device 200 may be a radially collapsed state if it is described to re-position the valve device 200 with the stent 140 or to withdraw the device 200, for example for replacement and/or for replacement of the host stent 140.

Thus, the collapsibility of the valves enables its optional removal by disengagement of the protrusions 155 from the host stent 140, thus eliminating any axial friction associated with the host stent 140.

Figure 1:
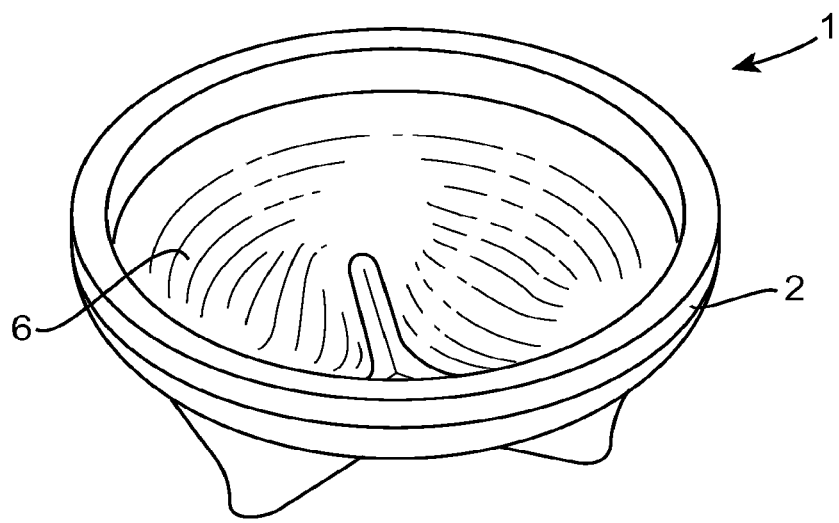
FIG. 1 is an isometric view (from above) of an esophageal valve according to the invention.
Figure 3:
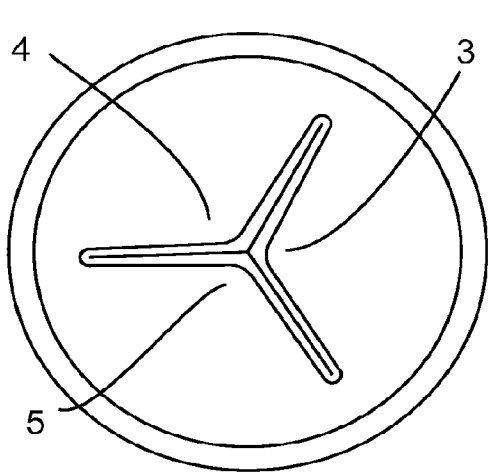
FIG. 3 is a top plan view of the valve.
Figure 4:
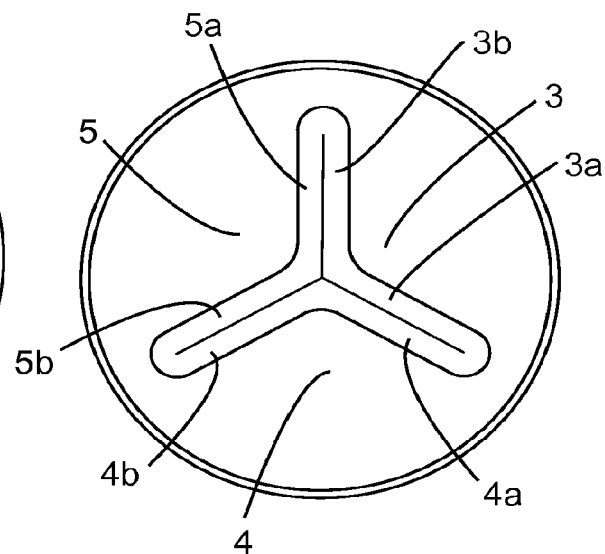
FIG. 4 is an underneath plan view of the valve.
Figure 5:
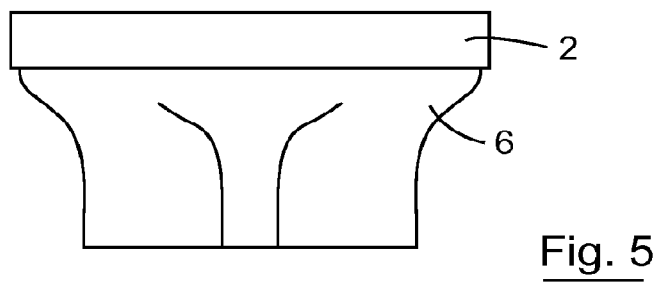
FIGS. 5 and 6 are elevational views of the valve.
Figure 6:
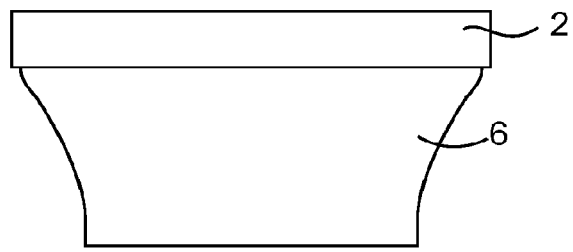
Figure 9:
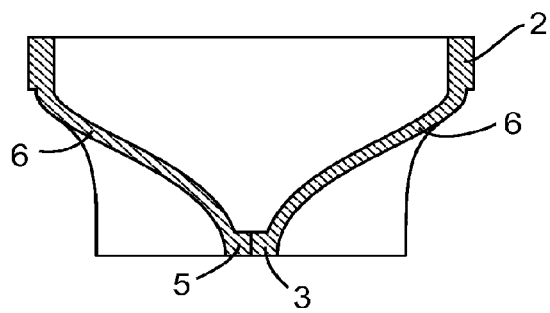
FIGS. 9 and 10 are cross sectional views of the valve.
Figure 10:
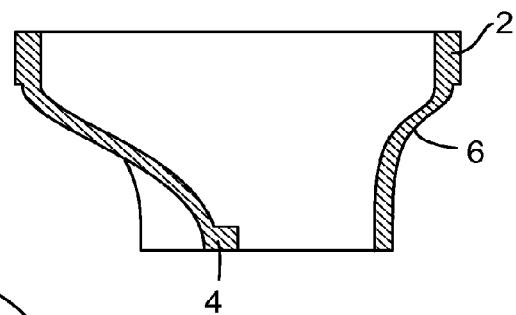
Figure 7:
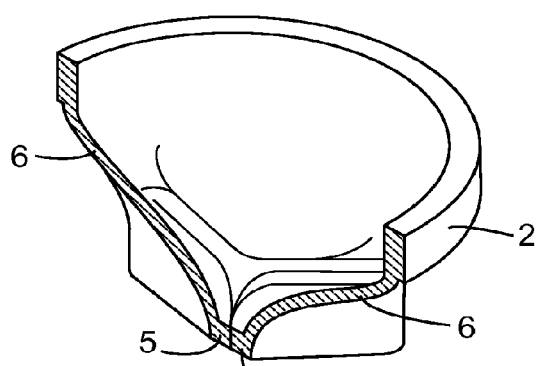
FIGS. 7 and 8 are isometric, partially cut-away sectional, views of the valve.
Figure 8:
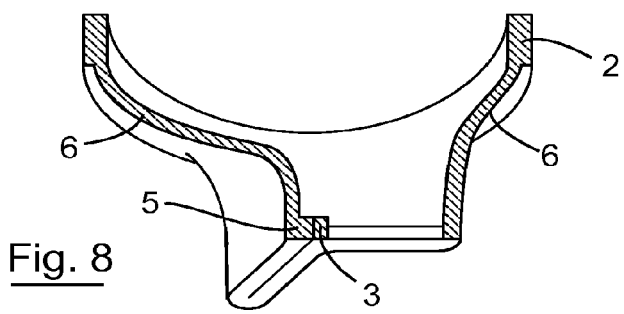
Figure 11:
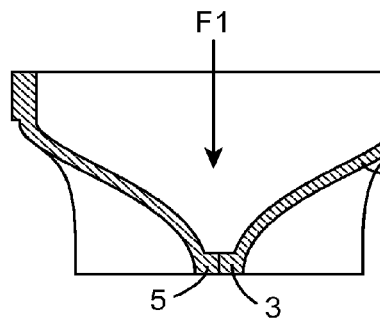
FIG. 11 is a cross sectional view of the valve in a normally closed configuration with an antegrade force applied.

The valve of FIGS. 1 to 63 is partially useful in patients with a constriction in their esophagus, for example as a result of esophageal cancer. The valve may be located proximal to the distal end of the esophagus and proximal of the distal end of the prosthesis in which it is mounted/deployed. The valve is relatively short and is typically less than 30 mm, less than 25 mm, less than 20 mm, less than 15 mm and is typically about 10.6 mm long with an outer rim diameter of 18 mm or about 11 mm long for an outer rim diameter of 20 mm.

The valve may have any desired number of leaflets, for example the valve 250 illustrated in FIGS. 64 to 70 has six valve leaflets 251. These leaflets 251 are oriented perpendicular to direction of food flow to additionally allow greater distensibility of the valve aperture.

Referring to FIGS. 71 to 83 there is illustrated another valve device according to the invention. The device 300 comprises an esophageal valve 301 which can open automatically in the antegrade direction (food intake) and in the retrograde direction (from the stomach to the mouth).

The valve 301 is similar to the valve of FIGS. 64 to 70 and comprises a polymeric valve body having a proximal outer support region with a rim 302, six valve leaflets 303, and a main body region 306 extending between the support rim 302 and the valve leaflets 303. The valve leaflets 303 extend inwardly and distally and terminate at distal end faces 303 respectively. The leaflets each 303 have legs which extend at an included angle of 60° to each other. The adjacent pairs of legs co-apt to close the gap between the valve leaflets 303 when the valve is in the normally closed configuration.

The valve 301 has three configurations. The first configuration is a normally closed configuration in which the valve leaflets 303 co-apt to close the valve. The second configuration is an antegrade open configuration in which the valve leaflets 303 are opened such that the leaflet leg pairs are opened and spaced-apart in response to an antegrade force F1 to allow flow through the valve 301. The third configuration is a retrograde open configuration in response to a retrograde force which is substantially larger than the antegrade force F2.

Figure 71:
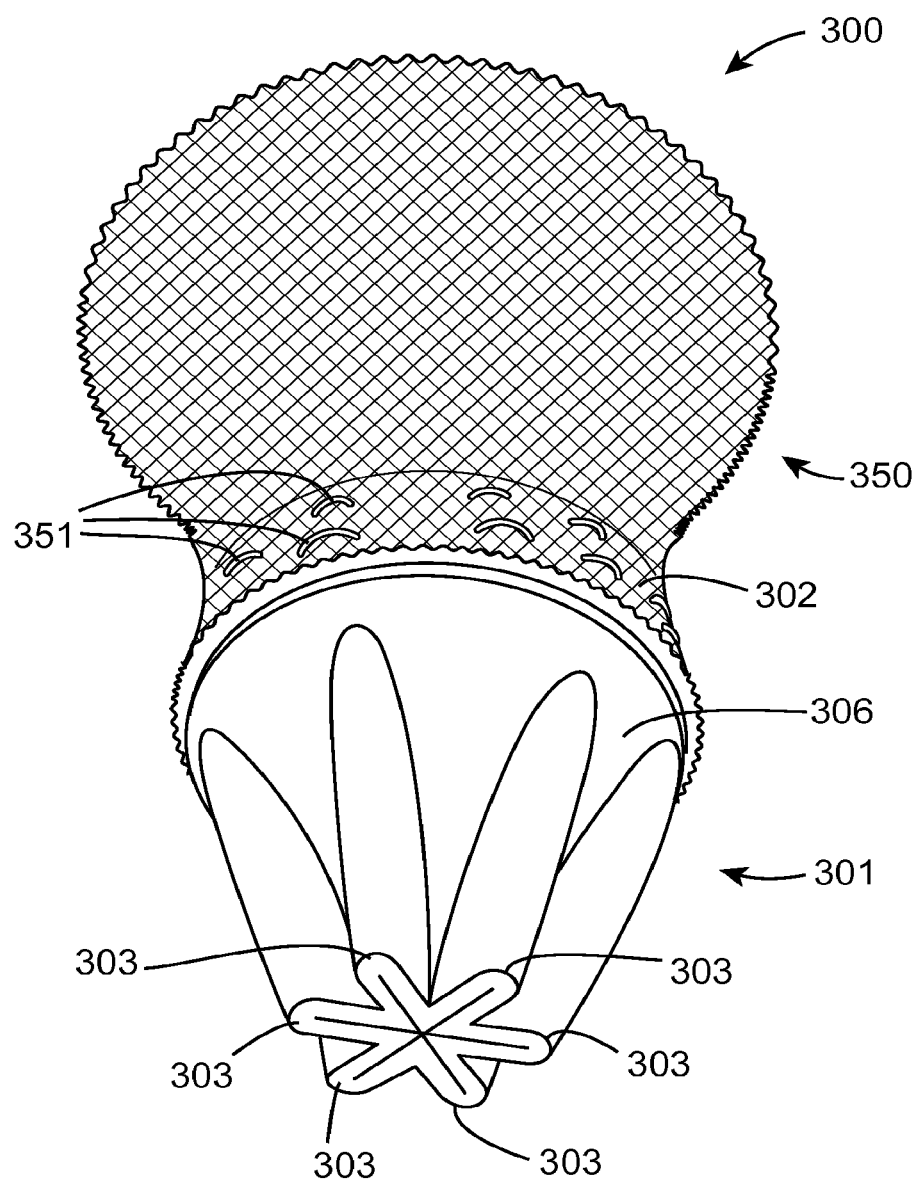
FIG. 71 is an isometric view of a valve and an associated support.
Figure 72:
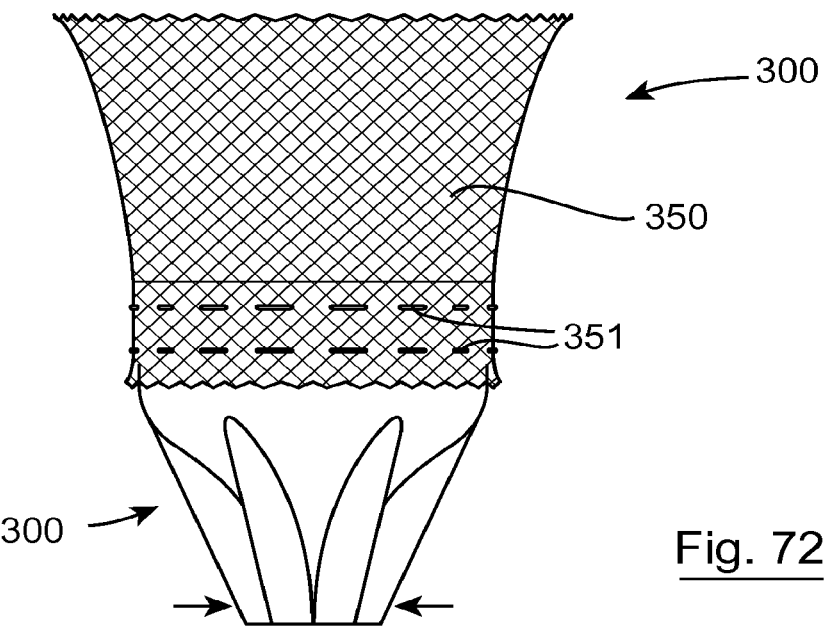
FIG. 72 is an elevational view of the valve and support of FIG. 71.
Figure 73:
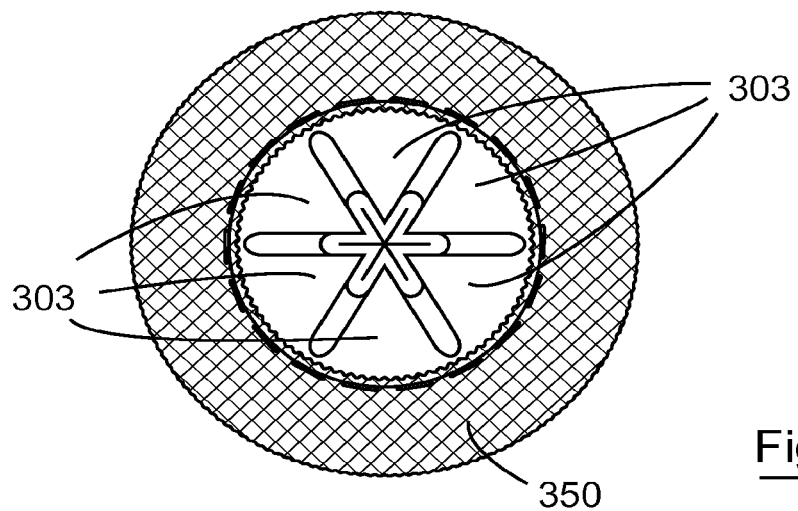
FIG. 73 is a plan view of the device of FIGS. 71 and 72 with the valve in a closed configuration.
Figure 74:
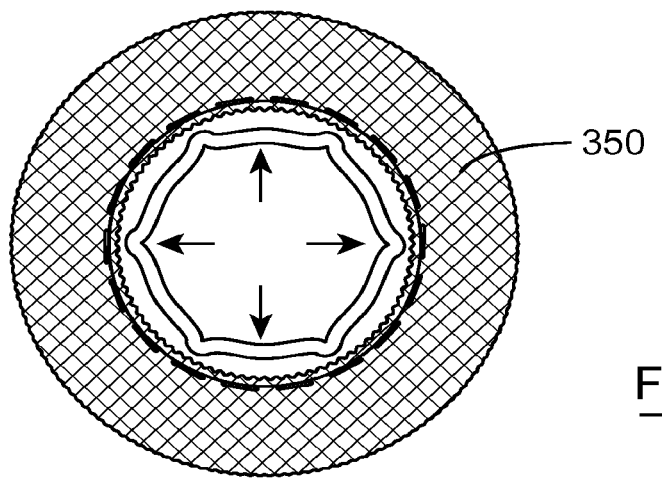
FIG. 74 is a plan view similar to FIG. 73 with the valve in an open configuration.
Figure 75:
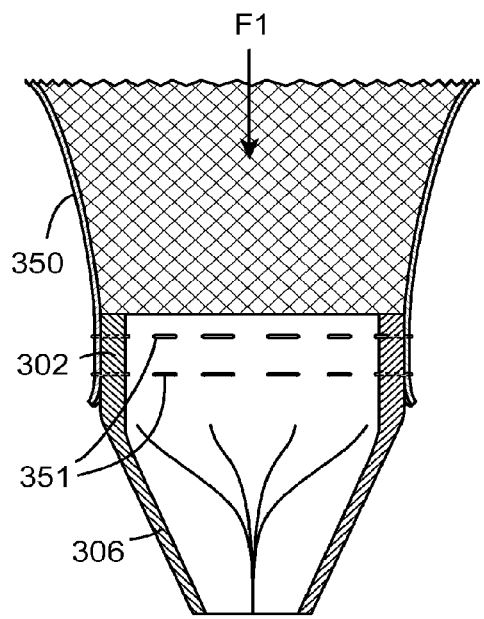
FIGS. 75 and 76 are side views of the device of FIG. 73 with the valve in a closed configuration.
Figure 77:
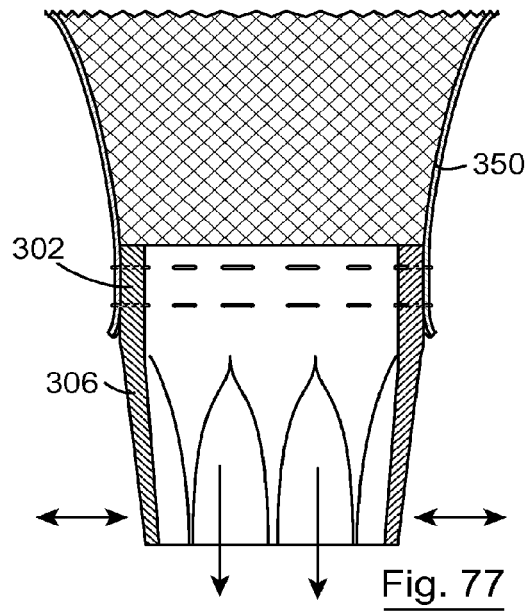
FIGS. 77 and 78 are side views of the device of FIG. 73 with the valve in the open configuration.
Figure 76:
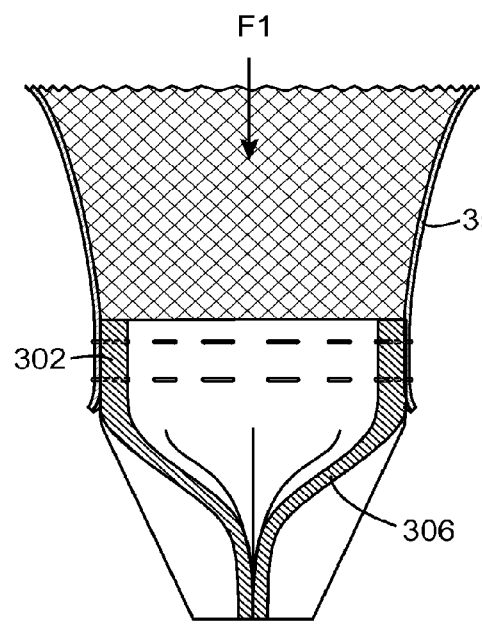
Figure 78:
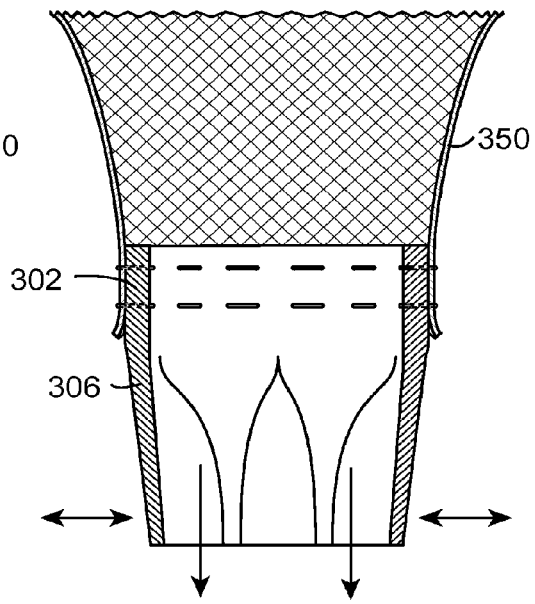
Figure 79:
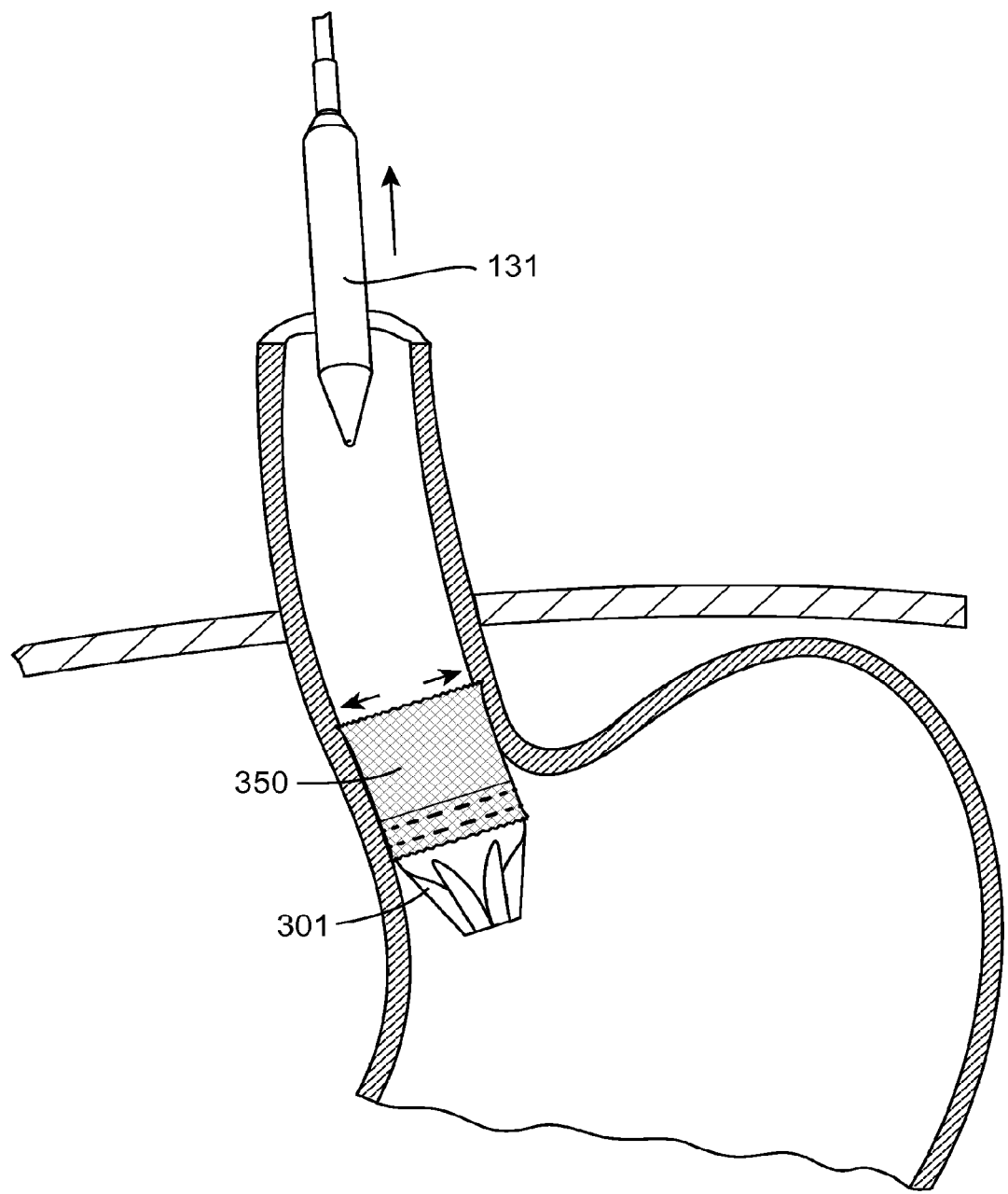
FIG. 79 is a cross sectional view of the device of FIG. 72 in use in a closed configuration.
Figure 80:
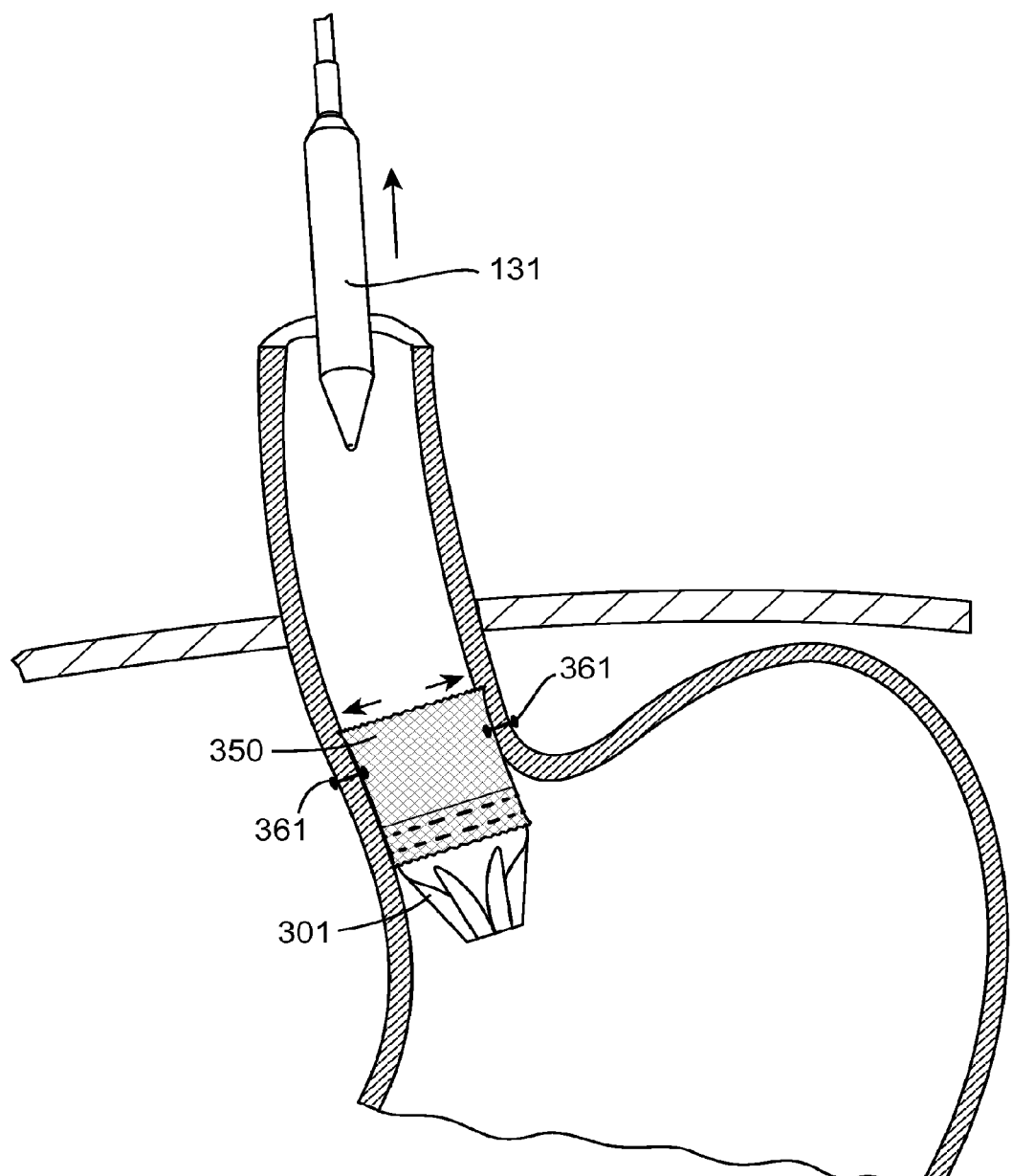
FIG. 80 is a view similar to FIG. 79 with the device anchored at the desired location.

The various configurations of the valve 1 are illustrated in FIGS. 71 to 82. In the first or normally closed configuration (FIGS. 71, 72) the valve leaflets 303 co-apt. When an antegrade force F1 is applied to the valve leaflets 303 the leaflet legs pairs open to allow antegrade flow to pass (FIGS. 74, 77, 78). When the antegrade force F1 is removed the leaflets 303 return to the closed position under the inherent biasing of the polymeric material of the valve body (FIG. 71).

Figure 81:
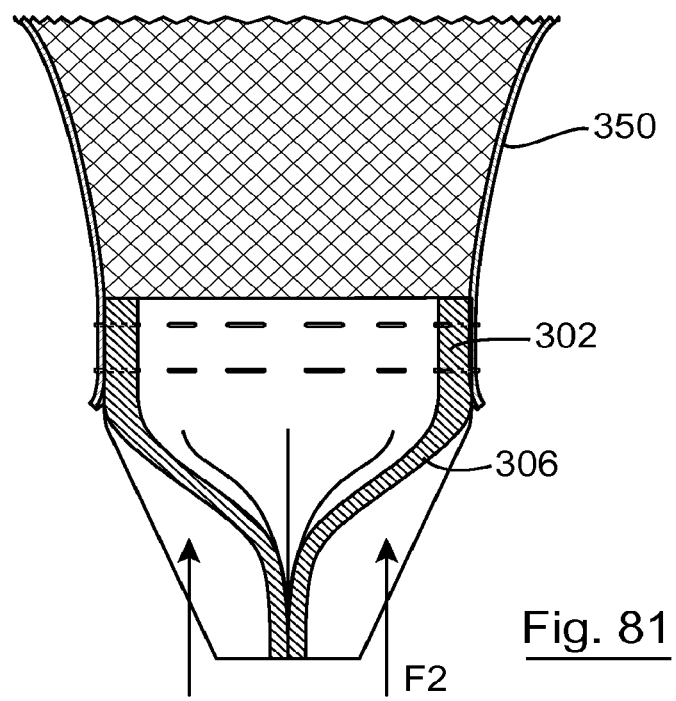
FIG. 81 is a cross sectional view of the device in a closed configuration.
Figure 82:
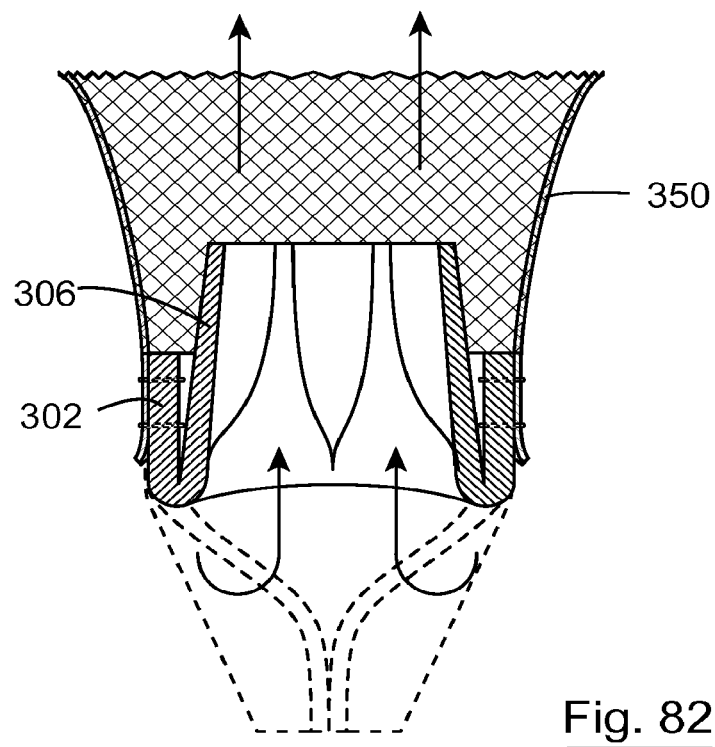
FIG. 82 is a cross sectional view of the device with the valve in the retrograde open configuration.

When a retrograde force F2 is applied to the valve body. This force initially pushes the valve leaflets 303 against one another (FIG. 80) and if the pressure is greater than a set value, the valve body will invert as illustrated in FIG. 81. When the valve is fully opened in response to retrograde force $F_2$ the valve main body (and the leaflets 303) extend proximally (upwardly) as illustrated in FIG. 81. This allows retrograde flow to pass through the valve. When the retrograde force F2 is removed the valve main body will return to the original configuration by everting in response to the biasing of the polymeric material to return to the normally closed configuration with the valve leaflets extending distally as illustrated in FIG. 71.

The valve leaflets 303 are reinforced in the region of co-aption. In this case, this is achieved by a local thickening of the polymeric material in this region. Similarly the support rim 302 is reinforced by a local thickening of the polymeric material.

The region of co-aption of the valve leaflets 303 has an axial extent which is typically from 1 to 5 mm. This ensures positive co-aption of the leaflets across a significant interfacial area when the valve is in the normally closed configuration. The thickness of the leaflets at the region of co-aption is typically between 0.1 mm and 10 mm.

The valve body 306 has a generally concave outer face and a generally convex inner face.

The valve 300 is a two-way valve. Different forces are required to open the valve from the proximal or distal directions. The valve 300 requires very little force to open in the antegrade direction, a pressure of 0.7 mm Hg in the antegrade direction is sufficient to allow a flowrate of 140 ml/min. In the retrograde direction the valve 1 can hold pressures of between 15 mm Hg and 40 mm Hg and higher. By varying the properties (such as density) of the material of the valve the valve can be tailored to accommodate varying yield pressures. The valve 300 accomplishes this by controllably inverting when placed under pressure in the retrograde direction.

The valve 300 of the invention returns to its original working position after being fully opened in the retrograde direction. This is accomplished without damaging the working valve.

When the valve 300 is opened by food passing in the antegrade direction the leaflets 303 open. The outer face of the valve has a greater resistance to change in shape and thus the force required to open main body in the retrograde direction is higher.

The important characteristics influencing the functioning of the valve 300 are the leaflet legs that impinge on one another. By varying the geometry and length of the leaflets 303 the valve 300 can be made to open in the retrograde direction at different pressures. Opening in the antegrade direction is somewhat less dependant on the geometry of the leaflets and more dependant on the elasticity and density of the material the device is made from. Additionally, the overall diameter and the diameter to which the leaflets open influence the opening force in both directions.

Because the stomach tends to have a slightly higher pressure than the oesophagus (on average. 12 mm Hg), a closed valve will experience this pressure at its distal surface. This distal pressure can ammeliorate the closing of a distally extending or tapering surface. However, previous examples of valves in the literature have relied on smooth surfaces to take advantage of this gastric pressure differential. Thus the only means of maximising the force generated by the gastric pressure was to increase the length of the distally extending or tapering surface. This in turn gave rise to problems associated will elongate structures becoming blocked with antegrade food flow and retrograde flow. The current invention teaches a method of retaining the short length of the valve structure and maximising the force generated by the gastric pressure through an increase in the surface area to length ratio. This is achieved by increasing the surface area of the distal surface of the valve by introducing pleats or folds (leaflets).

The valve may be of any suitable biocompatible polymeric material. It may be of a biocompatible polymeric material having properties which allow the valve to function as described.

The materials used for the production of this valve have a % elongation between 50% and 3000%. The material also has a tensile strength of between 0.01 and 5 MPa. Additionally the material could have an antimicrobial action to prevent colonisation when in-vivo. Additionally the material can be elastic or viscoelastic and can optionally be an open cell foam. The density of the material should be between 0.1 g/cm3 to 1.5 g/cm3.

The valve 300 of the invention may be mounted to any suitable luminal prosthesis, especially an esophageal prosthesis 350. The rim 302 of the valve provides a mounting ring for mounting within the prosthesis, for example, the valve 300 may be mounted to the stent by suturing the rim 2 to the stent mesh using sutures 351 as illustrated particularly in FIG. 71.

The prosthesis 350 may be of any suitable type. An uncoated and unsleeved stent 350 is illustrated in FIGS. 71 to 81.

In this case the valve 300 is mounted to a distal end of the prosthesis 350. The stomach produces a pressure of 7 mm Hg. The distal end of the valve is exposed to this pressure which compresses the material further to augment the closure force on the already closed valve. The prosthesis 350 is located so that it can be readily anchored in place for example, by tissue anchors 361 in the gastric cardia—in the region of tissue between the entrance to the stomach and lower esophageal sphincter. In general, the tissue wall is thickened in this region which facilitates anchoring of the prosthesis 350. The tissue anchors may be such as those used in the commerically available G-Cath system from USGI.

The prosthesis 350 is designed to be in situ for a long period of time. With a standard Nitinol metal stent a patient may be aware of its presence because of the radial force applied by the stent. The prosthesis 350 in contrast can be of a braided plastic mesh which is sufficiently self expanding that it remains in situ during fixing for example, using the tissue anchors 361. The mesh of the stent should be open enough to accept the tissue anchor without damaging the mesh but dense enough to prevent pull-through of the tissue anchor. The prosthesis typically has a radial force of less than 1.9 Kpa to retain it in situ without causing discomfort to the patient.

The valve device according to this embodiment is especially useful in the treatment of GERD, The valve is located distal to the distal end of the esophagus.

It will be noted that the valve is relatively short and does not extend significantly into the stomach. Prior art "windsock" type devices are long which can result in clogging by the contents of the stomach. Further material can rise up from the stomach by capillary action in such windsock devices. In contrast the GERD valve of the invention is typically less than 50 mm, less than 40 mm, less than 30 mm and is typically about 23 mm long for a diameter of 23 mm.

Figure 83:
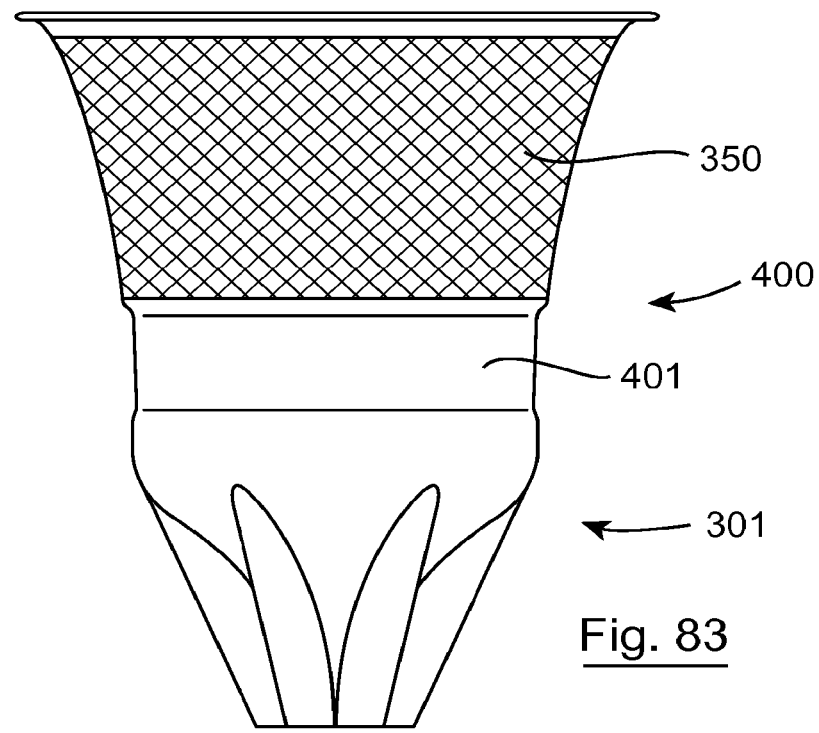
FIG. 83 is an elevational view of another device similar to FIG. 71.
Figure 84:
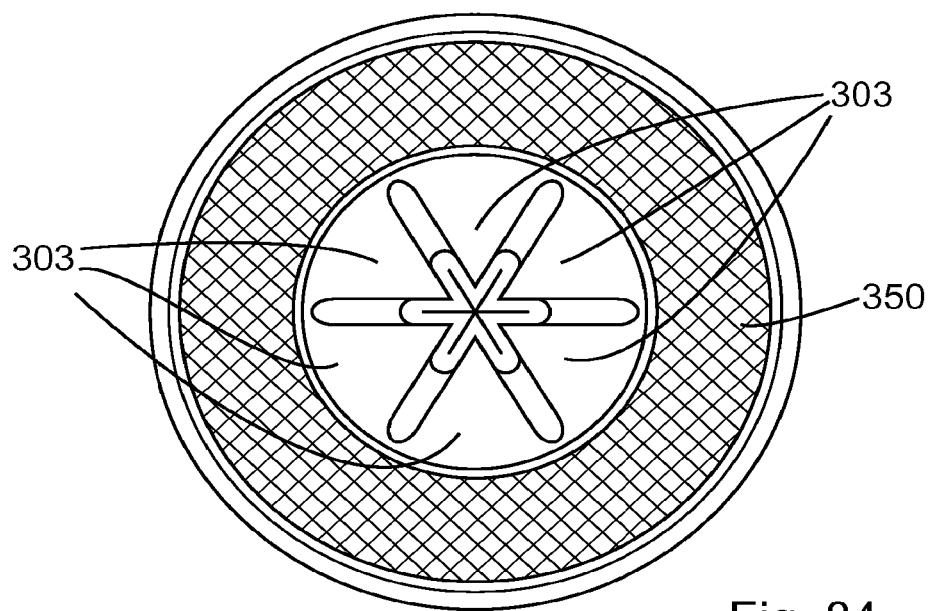
FIG. 84 is a plan view of the device of FIG. 83.

Referring to FIGS. 83 and 84 there is illustrated another device 400 according to the invention which is similar to the device of FIGS. 71 to 82 and like parts are assigned the same reference numerals. In this case the valve 301 is mounted to the prosthesis 350 by overmoulding 401 of the rim 302 of the valve to the distal end of the prosthesis 350. Overmoulding assists in spreading the axial load as there is a large area of content between the prosthesis 350 and the valve rim 302.

The esophageal valves of the invention can open automatically in the antegrade direction (food intake) and in the retrograde direction (from the stomach to the mouth).

The valves are two-way valves. Different forces are required to open in the valve from the proximal or distal directions. The valves require very little pressure to open in the antigrade direction, water at a pressure as low as 0.7 mm Hg will allow a flowrate of at least 140 ml/min. In the retrograde direction the valve can hold pressures of 30 mm Hg and higher. By varying the properties (such as density) of the material of the valve, the valve can be tailored to accommodate varying yield pressures. The valve accomplishes this by controllably inverting when placed under pressure in the retrograde direction.

The valves of the invention returns to its original working position after being fully opened in the retrograde direction. This is accomplished without damaging the working valve.

It will be appreciated that whilst the invention has been described with reference to an esophageal valve for mounting to a pre-deployed esophageal stent it may also be applied to mounting of valves in other body passageways including any artery or the urethra, or other locations in the gastrointestinal system such as a replacement for the ileocecal valve located between the small and the large intestine.

The following section describes one group of biomaterials that are suitable for manufacturing a valve of the invention.

Figure 85:
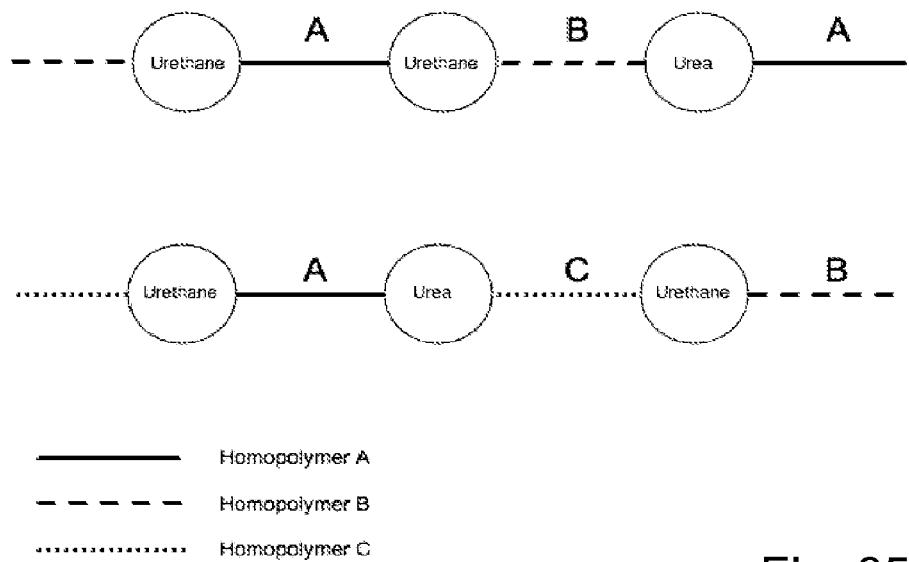
FIG. 85 is an illustration of prior art polymers with urea and urethane linkages interspersed between homopolymer soft segments.

Use of polyethers as soft segments in polyurethane foams is know to result in soft elastic and viscoelastic materials due to the dynamic reinforcing effect of hydrogen bonding. Conversely, use of non-hydrogen bonding hydrophobic soft segments results in harder, less elastic material. Blending of such hydrophobic and hydrophilic homopolymer soft segments as shown in FIG. 85 via urethane/urea linkages is known in the art to achieve mechanical properties appropriate to specific applications.

Acid catalysed hydrolytic degradation occurs at urethane linkages within polyurethane materials. These urethane/urea linkages are therefore the 'weak-links' of the polyurethane material. It follows that the intrinsic hydrophilicity of the polyurethane material will affect the rate of hydrolysis through modulation of water uptake. Thus, such materials are incompatible with use in a gastric environment (i.e., a highly acidic aqueous environment).

Thus, in some embodiments, the present invention provides a multiblock copolymer that is biomimetic and hydrolytically stable in a gastric environment. Such multiblock copolymers are of formula I:

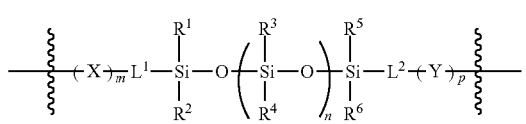

wherein:

each ⌇ represents a point of attachment to a urethane or urea linkage;

each of X and Y is independently a polymer or co-polymer chain formed from one or more of a polyether, a polyester, a polycarbonate, or a fluoropolymer;

each of $R^1$, $R^2$, $R^3$, $R^4$, $R^5$ and $R^6$ is independently selected from one or more of R, OR, —$CO_2$R, a fluorinated hydrocarbon, a polyether, a polyester or a fluoropolymer;

each R is independently hydrogen, an optionally substituted $C_{1-20}$ aliphatic group, or an optionally substituted group selected from phenyl, 8-10 membered bicyclic aryl, a 4-8 membered monocyclic saturated or partially unsaturated heterocyclic ring having 1-2 heteroatoms independently selected from nitrogen, oxygen, or sulphur, or 5-6 membered monocyclic or 8-10 membered bicyclic heteroaryl group having 1-4 heteroatoms independently selected from nitrogen, oxygen, or sulfur;

each of m n and p is independently 2 to 100; and each of $L^1$ and $L^2$ is independently a bivalent $C_{1-20}$ hydrocarbon chain wherein 1-4 methylene units of the hydrocarbon chain are optionally and independently replaced by —O—, —S—, —N(R)—, —C(O)—, —C(O)N(R)—, —N(R)C(O)—, —$SO_2$—, —$SO_2$N(R)—, —N(R)$SO_2$—, —OC(O)—, —C(O)O—, or a bivalent cycloalkylene, arylene, heterocyclene, or heteroarylene, provided that neither of $L^1$ nor $L^2$ comprises a urea or urethane moiety.

2. Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^1$ (as in N-substituted pyrrolidinyl)).

The term "unsaturated", as used herein, means that a moiety has one or more units of unsaturation.

As used herein, the term "bivalent $C_{1-8}$ [or $C_{1-6}$] saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^●$, -(halo$R^*$), —OH, —$OR^●$, —$O(haloR^●)$, —CN, —C(O)OH, —$C(O)OR^●$, —$NH_2$, —$NHR^●$, —$NR^●_2$, or —$NO_2$, wherein each $R^●$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

3. Description of Exemplary Embodiments:

A. Multiblock Copolymers

As described generally above, one embodiment of the present invention provides a triblock copolymer of formula I:

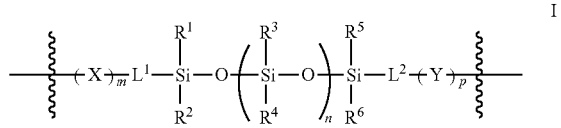

I wherein the copolymers are chemically interspersed (bound) between urethane and/or urea linkages (i.e., at the bond designated with ⌇) and wherein each of X, Y, m, n, p, $L^1$, $L^2$, $R^1$, $R^2$, $R^3$, $R^4$, $R^5$, and $R^6$ is as defined and described herein.

As defined generally above, the each of X and Y groups of formula I is independently a polymer or co-polymer chain formed from one or more of a polyether, a polyester, a polycarbonate, and a fluoropolymer.

Examples of polymer or co-polymer chains represented by X and/or Y include: poly(ethylene oxide), poly(difluoromethyl ethylene oxide), poly(trifluoromethyl ethylene oxide), poly(propylene oxide), poly(difluoromethyl propylene oxide), poly(propylene oxide), poly(trifluoromethyl propylene oxide), poly(butylene oxide), poly(tetramethylene ether glycol), poly(tetrahydrofuran), poly(oxymethylene), poly(ether ketone), poly(etherether ketone) and copolymers thereof, poly(dimethylsiloxane), poly(diethylsiloxane) and higher alkyl siloxanes, poly(methyl phenyl siloxane), poly (diphenyl siloxane), poly(methyl di-fluoroethyl siloxane), poly(methyl tri-fluoroethyl siloxane), poly(phenyl di-fluoroethyl siloxane), poly(phenyl tri-fluoroethyl siloxane) and copolymers thereof, poly(ethylene terephthalate) (PET), poly (ethylene terephthalate ionomer) (PETI), poly(ethylene naphthalate) (PEN), poly(methylene naphthalate) (PTN), poly(butylene teraphalate) (PBT), poly(butylene naphthalate) (PBN), polycarbonate. In certain embodiments, the present invention provides a pre-formed soft segment for a polyurethane/urea foam.

In some embodiments X is a polyether and Y is a polyether. More specifically in one case X and Y are both poly(propylene oxide).

In certain embodiments, m and p are each independently between 2 and 50 and n is between 2 and 20. In some embodiments, m and p are each independently between 2 and 30 and n is between 2 and 20.

As defined generally above, each of $R^1$, $R^2$, $R^3$, $R^4$, $R^5$ and $R^6$ is independently selected from one or more of R, OR, —$CO_2R$, a fluorinated hydrocarbon, a polyether, a polyester or a fluoropolymer. In some embodiments, one or more of $R^1$, $R^2$, $R^3$, $R^4$, $R^5$ and $R^6$ is —$CO_2R$. In some embodiments, one or more of $R^1$, $R^2$, $R^3$, $R^4$, $R^5$ and $R^6$ is —$CO_2R$ wherein each R is independently an optionally substituted $C_{1-6}$ aliphatic group. In certain embodiments, one or more of $R^1$, $R^2$, $R^3$, $R^4$, $R^5$ and $R^6$ is —$CO_2R$ wherein each R is independently an unsubstituted $C_{1-6}$ alkyl group. Exemplary such groups include methanoic or ethanoic acid as well as methacrylic acid and other acrylic acids.

In certain embodiments, one or more of $R^1$, $R^2$, $R^3$, $R^4$, $R^5$ and $R^6$ is independently R. In some embodiments, one or more of $R^1$, $R^2$, $R^3$, $R^4$, $R^5$ and $R^6$ is an optionally substituted $C_{1-6}$ aliphatic group. In certain embodiments, one or more of $R^1$, $R^2$, $R^3$, $R^4$, $R^5$, and $R^6$ is an optionally substituted $C_{1-6}$ alkyl. In other embodiments, one or more of $R^1$, $R^2$, $R^3$, $R^4$, $R^5$, and $R^6$ is an optionally substituted group selected from phenyl, 8-10 membered bicyclic aryl, a 4-8 membered monocyclic saturated or partially unsaturated heterocyclic ring having 1-2 heteroatoms independently selected from nitrogen, oxygen, or sulphur, or 5-6 membered monocyclic or 8-10 membered bicyclic heteroaryl group having 1-4 heteroatoms independently selected from nitrogen, oxygen, or sulphur. Exemplary such $R^1$, $R^2$, $R^3$, $R^4$, $R^5$ and $R^6$ groups include methyl, ethyl, propyl, isopropyl, cyclopropyl, butyl, isobutyl, cyclobutyl, phenyl, pyridyl, morpholinyl, pyrrolidinyl, imidazolyl, and cyclohexyl.

In certain embodiments, one or more of $R^1$, $R^2$, $R^3$, $R^4$, $R^5$ and $R^6$ is independently —OR. In some embodiments, one or more of $R^1$, $R^2$, $R^3$, $R^4$, $R^5$ and $R^6$ is —OR wherein R is an optionally substituted $C_{1-6}$ aliphatic group. In certain embodiments, one or more of $R^1$, $R^2$, $R^3$, $R^4$, $R^5$ and $R^6$ is —OR wherein R is $C_{1-6}$ alkyl. In other embodiments, one or more of $R^1$, $R^2$, $R^3$, $R^4$, $R^5$ and $R^6$ is —OR wherein R is an optionally substituted group selected from phenyl, 8-10 membered bicyclic aryl, a 4-8 membered monocyclic saturated or partially unsaturated heterocyclic ring having 1-2 heteroatoms independently selected from nitrogen, oxygen, or sulphur, or 5-6 membered monocyclic or 8-10 membered bicyclic heteroaryl group having 1-4 heteroatoms independently selected from nitrogen, oxygen, or sulphur. Exemplary such $R^1$, $R^2$, $R^3$, $R^4$, $R^5$ and $R^6$ groups include —Omethyl, —Oethyl, —Opropyl, —Oisopropyl, —Ocyclopropyl, —Obutyl, —Oisobutyl, —Ocyclobutyl, —Ophenyl, —Opyridyl, —Omorpholinyl, —Opyrrolidinyl, —Oimidazolyl, and —Ocyclohexyl.

In certain embodiments, one or more of $R^1$, $R^2$, $R^3$, $R^4$, $R^5$ and $R^6$ is independently R wherein each R is a $C_{1-6}$ aliphatic group substituted with one or more halogens. In some embodiments, each R is $C_{1-6}$ aliphatic substituted with one, two, or three halogens. In other embodiments, each R is a perfluorinated $C_{1-6}$ aliphatic group. Examples of fluorinated hydrocarbons represented by $R^1$, $R^2$, $R^3$, $R^4$, $R^5$ and $R^6$ include mono-, di-, tri, or perfluorinated methyl, ethyl, propyl, butyl, or phenyl. In some embodiments, each of $R^1$, $R^2$, $R^3$, $R^4$, $R^5$ and $R^6$ is trifluoromethyl, trifluoroethyl, or trifluoropropyl.

In certain embodiments, one or more of $R^1$, $R^2$, $R^3$, $R^4$, $R^5$ and $R^6$ is independently a polyether. Examples of polyethers represented by $R^1$, $R^2$, $R^3$, $R^4$, $R^5$ and $R^6$ include poly(ethylene oxide), poly(difluoromethyl ethylene oxide), poly(trifluoromethyl ethylene oxide), poly(propylene oxide), poly(difluoromethyl propylene oxide), poly(propylene oxide), poly(trifluoromethyl propylene oxide), poly(butylene oxide), poly(tetramethylene ether glycol), poly(tetrahydrofuran), poly(oxymethylene), poly(ether ketone), poly(etherether ketone) and copolymers thereof.

In certain embodiments, one or more of $R^1$, $R^2$, $R^3$, $R^4$, $R^5$ and $R^6$ is independently a polyester. Examples of polyesters represented by $R^1$, $R^2$, $R^3$, $R^4$, $R^5$ and $R^6$ include poly(ethylene terephthalate) (PET), poly(ethylene terephthalate ionomer) (PETI), poly(ethylene naphthalate) (PEN), poly(methylene naphthalate) (PTN), poly(butylene teraphalate) (PBT), poly(butylene naphthalate) (PBN), polycarbonate.

In certain embodiments, one or more of $R^1$, $R^2$, $R^3$, $R^4$, $R^5$ and $R^6$ is independently a fluoropolymer. Examples of fluoropolymers represented by $R^1$, $R^2$, $R^3$, $R^4$, $R^5$ and $R^6$ include poly(tetrafluoroethylene), poly(methyl di-fluoroethyl siloxane), poly(methyl tri-fluoroethyl siloxane), poly(phenyl di-fluoroethyl siloxane).

In some embodiments, $R^1$, $R^2$, $R^3$, $R^4$, $R^5$ and $R^6$ is independently hydrogen, hydroxyl, carboxylic acids such as methanoic or ethanoic acid as well as methacrylic acid and other acrylic acids. Alkyl or aryl hydrocarbons such as methyl, ethyl, propyl, butyl, phenyl and ethers thereof.

Fluorinated hydrocarbons such as mono-, di-, tri, or perfluorinated methyl, ethyl, propyl, butyl, phenyl. Polyether such as Poly(ethylene oxide), poly(difluoromethyl ethylene oxide), poly(trifluoromethyl ethylene oxide), poly(propylene oxide), poly(difluoromethyl propylene oxide), poly(propylene oxide), poly(trifluoromethyl propylene oxide), poly(butylene oxide), poly(tetramethylene ether glycol), poly(tetrahydrofuran), poly(oxymethylene), poly(ether ketone), poly(etherether ketone) and copolymers thereof. Polyesters such as Poly(ethylene terephthalate) (PET), poly(ethylene terephthalate ionomer) (PETI), poly(ethylene naphthalate) (PEN), poly(methylene naphthalate) (PTN), Poly(Butylene Teraphalate) (PBT), poly(butylene naphthalate) (PBN), polycarbonate and fluoropolymer such as Poly(tetrafluoroethylene), poly(methyl di-fluoroethyl siloxane), poly(methyl tri-fluoroethyl siloxane), poly(phenyl di-fluoroethyl siloxane).

In some embodiments, m and p are between 2 and 50 and n is between 2 and 20. In certain embodiments, m and o are between 2 and 30 and n is between 2 and 20.

As defined generally above, each of $L^1$ and $L^2$ is independently a bivalent $C_{1-20}$ hydrocarbon chain wherein 1-4 methylene units of the hydrocarbon chain are optionally and independently replaced by —O—, —S—, —N(R)—, —C(O)—, —C(O)N(R)—, —N(R)C(O)—, —SO$_2$—, —SO$_2$N(R)—, —N(R)SO$_2$—, —OC(O)—, —C(O)O—, or a bivalent cycloalkylene, arylene, heterocyclene, or heteroarylene, provided that neither of $L^1$ nor $L^2$ comprises a urea or urethane moiety. In some embodiments, each of $L^1$ and $L^2$ is independently a bivalent $C_{1-20}$ alkylene chain. In certain embodiments, each of $L^1$ and $L^2$ is independently a bivalent $C_{1-10}$ alkylene chain. In certain embodiments, each of $L^1$ and $L^2$ is independently a bivalent $C_{1-6}$ alkylene chain. In certain embodiments, each of $L^1$ and $L^2$ is independently a bivalent $C_{1-4}$ alkylene chain. Exemplary such $L^1$ and $L^2$ groups include methylene, ethylene, propylene, butylene or higher bivalent alkanes.

In some embodiments, each of $L^1$ and $L^2$ is independently a bivalent $C_{1-20}$ alkylene chain wherein one methylene unit of the chain is replaced by —O—. In some embodiments, each of $L^1$ and $L^2$ is independently a bivalent $C_{1-10}$ alkylene chain wherein one methylene unit of the chain is replaced by —O—. In some embodiments, each of $L^1$ and $L^2$ is independently a bivalent $C_{1-6}$ alkylene chain wherein one methylene unit of the chain is replaced by —O—. In some embodiments, each of $L^1$ and $L^2$ is independently a bivalent $C_{1-4}$ alkylene chain wherein one methylene unit of the chain is replaced by —O—. Exemplary such $L^1$ and $L^2$ groups include —OCH$_2$—, —OCH$_2$CH$_2$—, —OCH$_2$CH$_2$CH$_2$—, —OCH$_2$CH$_2$CH$_2$CH$_2$—, or higher bivalent alkylene ethers.

In some embodiments, each of $L^1$ and $L^2$ is independently a bivalent $C_{1-20}$ alkylene chain wherein at least one methylene unit of the chain is replaced by —O— and at least one methylene unit of the chain is replaced by a bivalent arylene. In some embodiments, each of $L^1$ and $L^2$ is independently a bivalent $C_{1-10}$ alkylene chain wherein at least one methylene unit of the chain is replaced by —O— and at least one methylene unit of the chain is replaced by a bivalent arylene. In some embodiments, each of $L^1$ and $L^2$ is independently a bivalent $C_{1-6}$ alkylene chain wherein at least one methylene unit of the chain is replaced by —O— and at least one methylene unit of the chain is replaced by a bivalent arylene. In some embodiments, each of $L^1$ and $L^2$ is independently a bivalent $C_{1-4}$ alkylene chain wherein at least one methylene unit of the chain is replaced by —O— and at least one methylene unit of the chain is replaced by a bivalent arylene. Exemplary such $L^1$ and $L^2$ groups include —OCH$_2$-phenylene-, —OCH$_2$CH$_2$-phenylene-, —OCH$_2$CH$_2$-phenylene-CH$_2$—, —OCH$_2$CH$_2$CH$_2$CH$_2$-phenylene-, and the like.

One of ordinary skill in the art would understand that a polyurethane results from the reaction of a diisocyanate and a hydroxyl group. Similarly, a polyurea results from the reaction of a diisocyanate and an amine. Each of these reactions is depicted below.

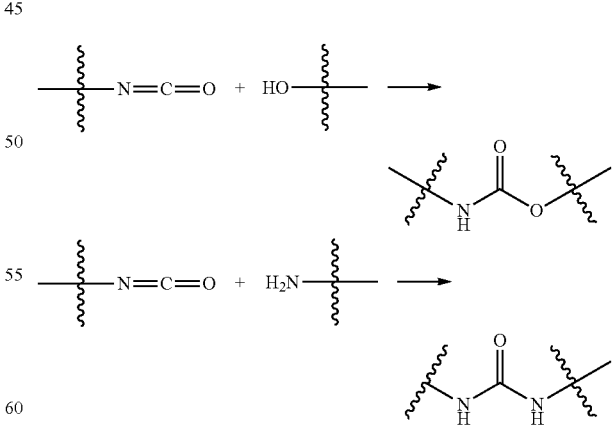

Thus, it is readily apparent that provided compounds of formula I can be functionalized with end groups suitable for forming urethane and/or urea linkages. In certain embodiments, the present invention provides a compound of formula II:

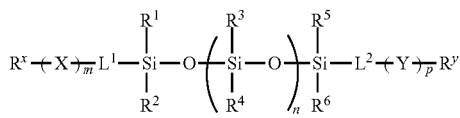

wherein:
each of $R^x$ and $R^y$ is independently —OH, —NH$_2$, a protected hydroxyl or a protected amine;
each of X and Y is independently a polymer or co-polymer chain formed from one or more of a polyether, a polyester, a polycarbonate, and a fluoropolymer;
each of $R^1$, $R^2$, $R^3$, $R^4$, $R^5$ and $R^6$ is independently selected from one or more of R, OR, —CO$_2$R, a fluorinated hydrocarbon, a polyether, a polyester or a fluoropolymer;
each R is independently hydrogen, an optionally substituted C$_{1-20}$ aliphatic group, or an optionally substituted group selected from phenyl, 8-10 membered bicyclic aryl, a 4-8 membered monocyclic saturated or partially unsaturated heterocyclic ring having 1-2 heteroatoms independently selected from nitrogen, oxygen, or sulphur, or 5-6 membered monocyclic or 8-10 membered bicyclic heteroaryl group having 1-4 heteroatoms independently selected from nitrogen, oxygen, or sulfur;
each of m n and p is independently 2 to 100; and
each of L$^1$ and L$^2$ is independently a bivalent C$_{1-20}$ hydrocarbon chain wherein 1-4 methylene units of the hydrocarbon chain are optionally and independently replaced by —O—, —S—, —N(R)—, —C(O)—, —C(O)N(R)—, —N(R)C(O)—, —SO$_2$—, —SO$_2$N(R)—, —N(R)SO$_2$—, —OC(O)—, —C(O)O—, or a bivalent cycloalkylene, arylene, heterocyclene, or heteroarylene, provided that neither of L$^1$ nor L$^2$ comprises a urea or urethane moiety.

In some embodiments, each of X, Y, m, n, p, L$^1$, L$^2$, R$^1$, R$^2$, R$^3$, R$^4$, R$^5$, and R$^6$ is as defined and described herein.

As defined generally above, each of R$^x$ and R$^y$ is independently —OH, —NH$_2$, a protected hydroxyl or a protected amine. In some embodiments, both of R$^x$ and R$^y$ are —OH. In other embodiments, both of R$^x$ and R$^y$ are —NH$_2$. In some embodiments one of R$^x$ and R$^y$ is —OH and the other is —NH$_2$.

In some embodiments, each of R$^x$ and R$^y$ is independently a protected hydroxyl or a protected amine. Such protected hydroxyl and protected amine groups are well known to one of skill in the art and include those described in detail in *Protecting Groups in Organic Synthesis*, T. W. Greene and P. G. M. Wuts, 3rd edition, John Wiley & Sons, 1999, the entirety of which is incorporated herein by reference. Exemplary protected amines include methyl carbamate, ethyl carbamante, 9-fluorenylmethyl carbamate (Fmoc), 9-(2-sulfo)fluorenylmethyl carbamate, 9-(2,7-dibromo) fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylamino carbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenyl azo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracene sulfonamide, 4-(4',8'-dimethoxynaphthylmethyl)benzenesulfonamide (DNMBS), benzylsulfonamide, trifluoromethylsulfonamide, and phenacylsulfonamide.

Exemplary hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), tri ethyl silyl (TES), triisopropyl silyl (TIPS), dim ethyl isopropyl silyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-tri chloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxy carbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

One of ordinary skill in the art will appreciate that the choice of hydroxyl and amine protecting groups can be such that these groups are removed at the same time (e.g., when both protecting groups are acid labile or base labile). Alternatively, such groups can be removed in a step-wise fashion (e.g., when one protecting group is removed first by one set of removal conditions and the other protecting group is removed second by a different set of removal conditions). Such methods are readily understood by one of ordinary skill in the art.

In certain embodiments, the present invention provides a compound of any of formulae II-a, II-b, II-c, and II-d:

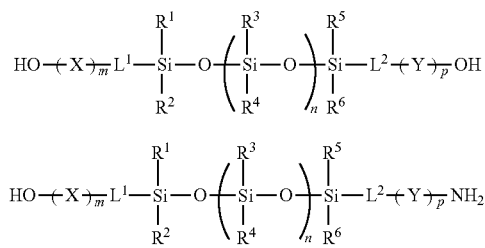

II-a

II-b

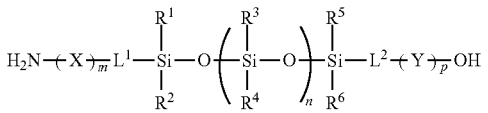

II-c

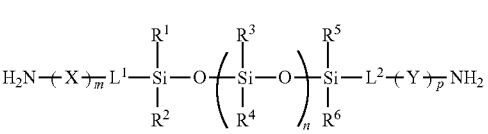

II-d wherein each of X, Y, m, n, p, $L^1$, $L^2$, $R^1$, $R^2$, $R^3$, $R^4$, $R^5$, and $R^6$ is as defined and described herein.

Exemplary triblock copolymers of the present invention are set forth below:

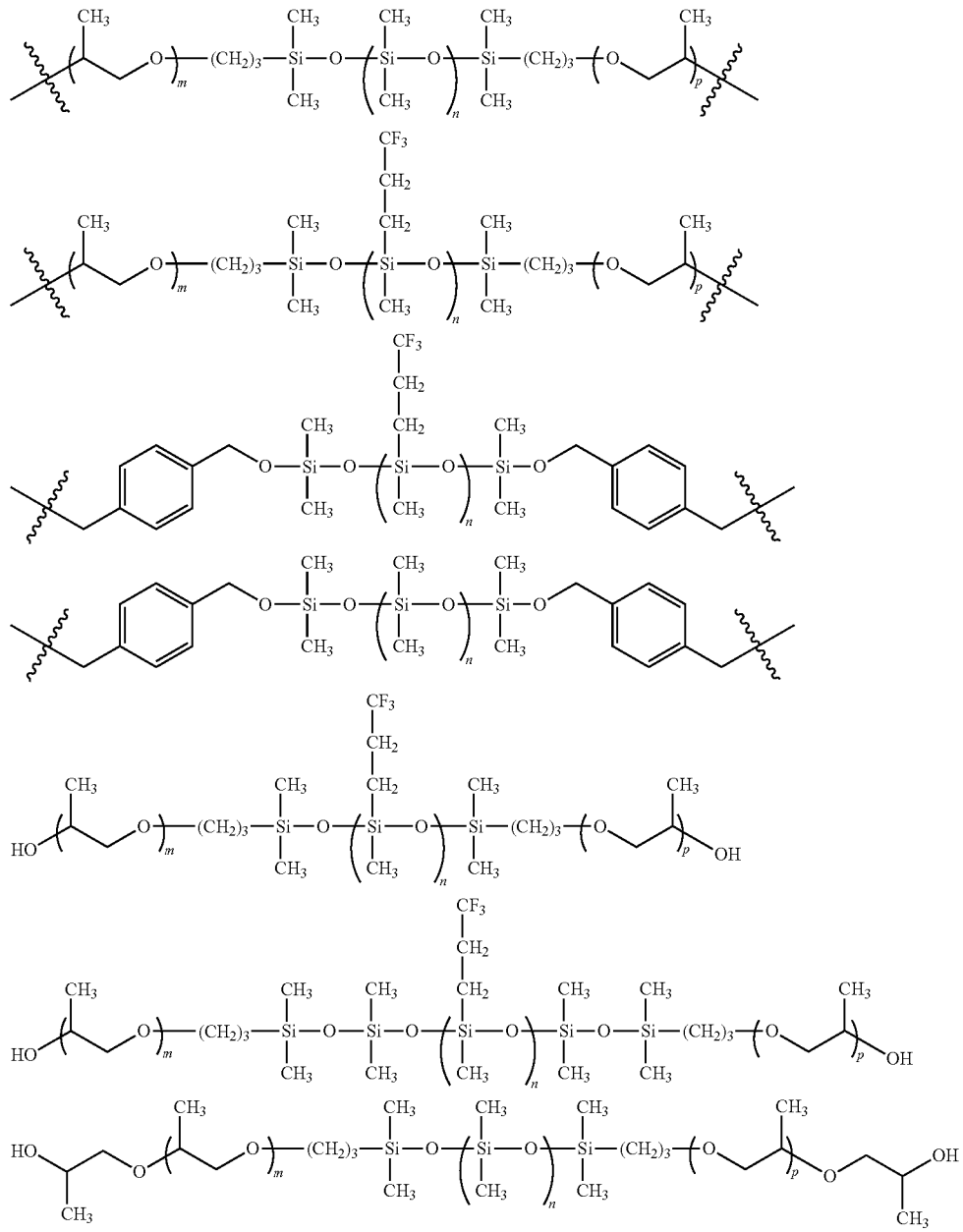

-continued

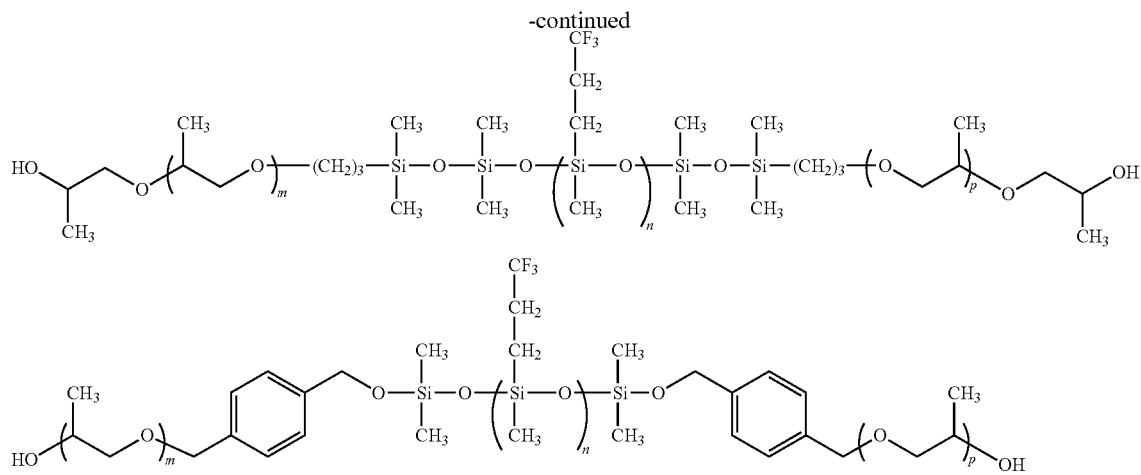

wherein each of m, n, and p is as defined and described herein.

In some embodiments, the present invention provides a polymer foam, comprising:
(a) one or more triblock copolymers of formula I:

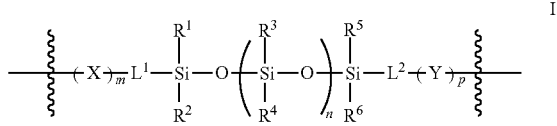

wherein each of X, Y, m, n, p, $L^1$, $L^2$, $R^1$, $R^2$, $R^3$, $R^4$, $R^5$, and $R^6$ is as defined and described herein; and
(b) wherein the copolymers are chemically interspersed (bound) between urethane and/or urea linkages (i.e., at the bond designated with ⸹ ).

The invention further provides a pre-formed soft segment of the formula I as defined above. In some embodiments, the present invention provides a polyurethane/urea foam comprising a soft segment triblock copolymer of formula I.

In some embodiments, the present invention provides a viscoelastic biostable water blown foam, comprising:
(a) one or more triblock copolymers of formula I:

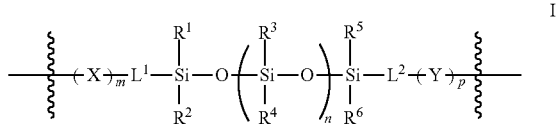

wherein each of X, Y, m, n, p, $L^1$, $L^2$, $R^1$, $R^2$, $R^3$, $R^4$, $R^5$, and $R^6$ is as defined and described herein; and
(b) wherein the copolymers are chemically interspersed (bound) between urethane and/or urea linkages (i.e., at the bond designated with ⸹ ).

It has been surprisingly found that polyurethanes and/or polyureas comprising a triblock copolymer of the present invention are stable to gastric fluid. Such polyurethanes and polyureas prepared using triblock copolymers of the present invention are viscoelastic and stable to gastric fluid. In some embodiments, a provided viscoelastic material is a foam.

In certain embodiments, a provided biostable foam is stable to gastric fluid. In some embodiments, a provided biostable foam is stable to gastric fluid for at least one year. In some embodiments, a provided biostable foam is stable to gastric fluid for at least 3 months, for at least 4 months, for at least 5 months, for at least 6 months, for at least 7 months, for at least 8 months, for at least 9 months, for at least 10 months, for at least 11 months, or for at least one year. Methods for determining stability of a provided biostable foam are known in the art utilizing simulated gastric fluid and include those described in detail in the Exemplification, infra.

In some embodiments, a provided viscoelastic foam, comprising a triblock copolymer of the present invention, is characterized in that the foam takes up less than about 30% by weight of water at equilibrium. In certain embodiments, a provided viscoelastic foam takes up less than about 5%, less than about 10%, less than about 15%, less than about 20%, less than about 25%, or less than about 30% by weight of water at equilibrium. One of ordinary skill in the art will appreciate that such chemical stability (i.e., in gastric fluid and therefore at very low pH) and hyrophobicity (i.e., water uptake of less than about 30% by weight) are characterisitics that differ dramatically from known siloxane polymers that are utilized in, e.g., the manufacture of contact lenses. For example, siloxane polymer that are utilized in, e.g., the manufacture of contact lenses require a water uptake of 50-120%.

As described above, the present invention provides a viscoelastic foam comprising a triblock copolymer of the present invention. It was suprisingly found that a provided foam has a high elongation capacity and the ability to recover very slowly following elongation. Indeed, it was found that a provided viscoelastic foam has an elongation capacity of about 200-1200%. In some embodiments, a provided viscoelastic foam has an elongation capacity of about 500%.

In some embodiments, a provided viscoelastic foam has a tensile strength of about 0.1 to about 1.0 MPa. In certain embodiments, a provided viscoelastic foam has a tensile strength of about 0.25 to about 0.5 MPa.

In some embodiments, a provided viscoelastic foam has a Young's Modulus of about 0.1 to about 0.6 MPa. In certain embodiments, a provided viscoelastic foam has a Young's Modulus of about 0.1 to about 0.5 MPa.

One of ordinary skill in the art will appreciate that, depending upon the physical characteristics required for a particular use of a provided foam, a foam of varying densities can be prepared. For example, a valve having a thinner wall would require a foam having a higher density than a similar valve having a thicker wall in order to result in each valve having a similar physical characteristic (e.g., tensile strength, and the like). Thus, in certain embodiments, a provided viscoelastic foam has a density of 0.1 to 1.5 g/cm³. In certain embodiments, a provided viscoelastic foam has a density of 0.3 to 1.2 g/cm³. In certain embodiments, a provided viscoelastic foam has a density of 0.8 to 0.9 g/cm³. In some embodiments, a provided viscoelastic foam has a density of 0.5 to 0.6 g/cm³.

Figure 86:
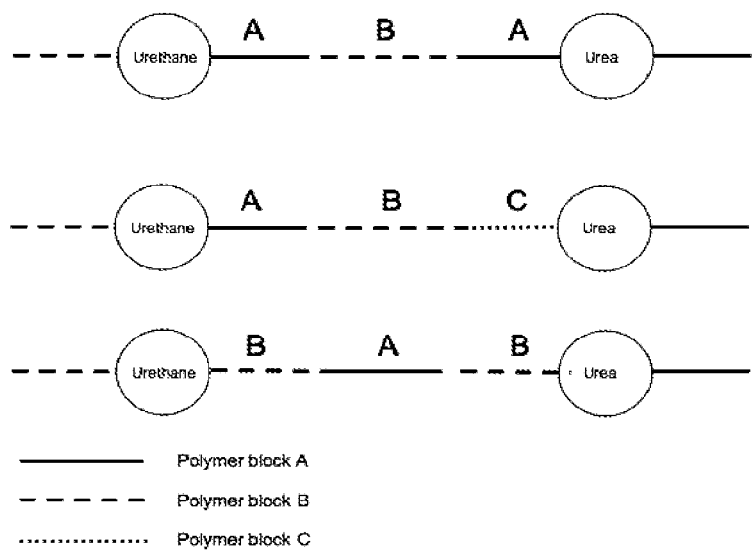
FIG. 86 is an illustration of a polyurethane/urea foam according to the invention with urea and urethane linkages interspersed between triblock copolymer soft segments.
Figure 87:
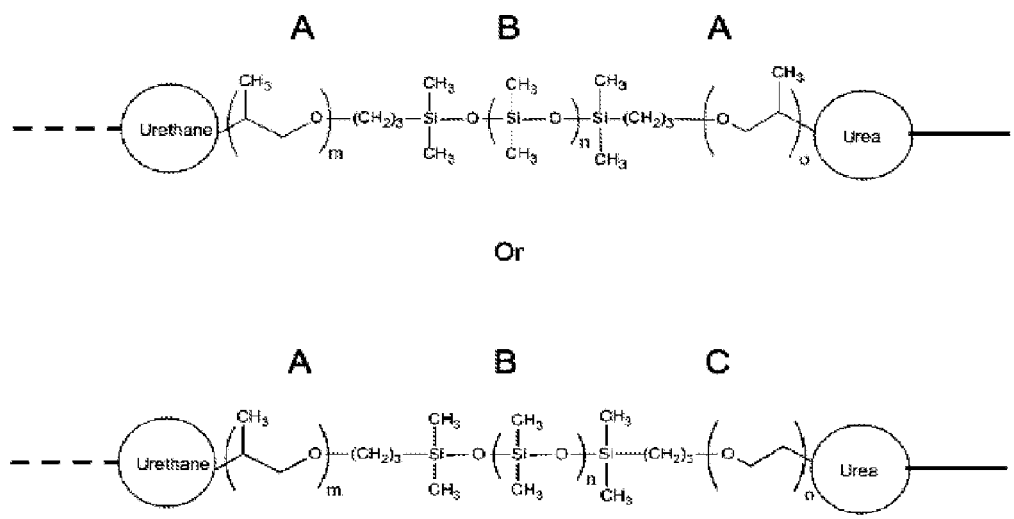
FIG. 87 is an illustration of a siloxane and polypropylene oxide based triblock copolymer in different forms.

In certain embodiments, the present invention provides polyether-siloxane and polyether-fluorosiloxane polyurethane materials with a greatly reduced number of weak-links as illustrated by FIG. 86 and FIG. 87. This was achieved by preforming the soft segment prior to the polyurethane reaction. In the examples below a triblock copolymer based on polydimethyl siloxane and polypropylene oxide was used but it will be appreciated that other triblock copolymers such as those formed from polysiloxanes and poly(ethylene oxide), poly(difluoromethyl ethylene oxide), poly(trifluoromethyl ethylene oxide), poly(propylene oxide), poly(difluoromethyl propylene oxide), poly(propylene oxide), poly(trifluoromethyl propylene oxide), poly(butylene oxide), poly(tetramethylene ether glycol), poly(tetrahydrofuran), poly(oxymethylene), poly(ether ketone), poly(etherether ketone) and copolymers thereof, poly(dimethylsiloxane), poly(diethylsiloxane) and higher alkyl siloxanes, poly(methyl phenyl siloxane), poly(diphenyl siloxane), poly(methyl di-fluoroethyl siloxane), poly(methyl tri-fluoroethyl siloxane), poly(phenyl di-fluoroethyl siloxane), poly(phenyl tri-fluoroethyl siloxane) and copolymers thereof, poly(ethylene terephthalate) (PET), poly(ethylene terephthalate ionomer) (PETI), poly (ethylene naphthalate) (PEN), poly(methylene naphthalate) (PTN), poly(butylene teraphalate) (PBT), poly(butylene naphthalate) (PBN) and polycarbonate could be used.

Referring to FIG. 86, copolymers of the form ABA, ABC and BAB were produced from homopolymers of polysiloxane and polypropylene oxide which were covalently linked using bonds less labile than urethane/urea. The molecular weight and chemical charateristics of such homopolymers were tailored to achieve a pre-soft-segment with the appropriate balance of hydrophilicity/hydrophobicity. Without wishing to be bound by any particular theory, it is believe that by using a non-urethane linked tri-block copolymer instead of the constiuent homopolymers as soft segments that the mechanical characteristics and hydrolytic stability of the resulting material is substantially improved.

In some embodiments, the present invention provides a foam comprising a copolymer of the present invention. Such foams offer specific advantages over solid elastomers, especially for gastrointestinal device applications. These advantages include enhanced biostability in the gastric environment, compressibility, viscoelasticity and high 'surface area to volume ratio'. The foam formulations of the invention can mimic mechanical characteristics of the native gastrointestinal tissue.

A biostable water blown foam was prepared from heterogenous reagents.

The prior art describes polyurethane foams that are prepared by the sequential reaction of polymer chains to one another resulting in a high molecular weight solid material. In all cases the polymeric precursors described in the art are linked together by urethane/urea linkages as illustrated in FIG. 85. However, each urethane/urea linkage is a possible site for degradation.

In the invention we have prepared a biostable polyurethane/urea foam with much fewer 'weak links' by using co-polymer precursors as shown in FIG. 86.

Polyurethane reactions have historically been carried out in a single phase due to ease of processing. However, we have made novel materials by combining physically heterogenous reaction pre-cursors together to form a stable two-phase dispersion ('water-in-oil') which was then reacted to form a foam.

EXEMPLIFICATION

In two specific examples X and Y are both polyethers namely poly(propylene oxide) (PPO). These were formulated into copolymers with poly(dimethylsiloxane) (PDMS) and poly(trifluoropropyl methylsiloxane) respectively in varying ratios as described by the following formulae:

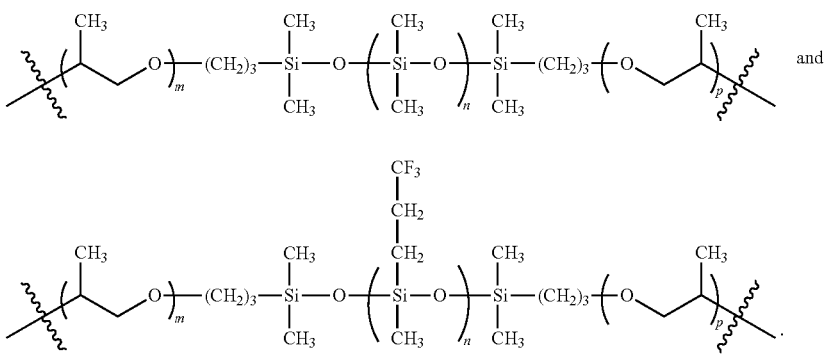

The formulations contained a number of other components including:
Branching Agent—DEOA

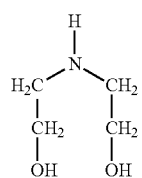

Diethanolamine (DEOA) is used as a branching agent although it is sometimes known as a crosslinking agent. The molecular weight of DEOA is 105.14 g/mol. The effect of the DEOA is to influence softness and elasticity of the end polymer.

Gelling Catalyst—Bismuth Neodecanoate (BICAT)

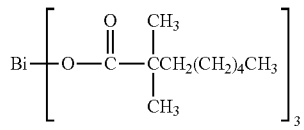

Bismuth neodecanoate is supplied as BiCat 8108M from Shepherd. It has a molecular weight of 722.75 g/mol. This catalyst is used to facilitate the complete reaction between isocyanate and hydroyl or amine functional groups.

Blowing Catalyst—DABCO 33-lv

DABCO is a common blowing catalyst for reaction between NCO and $H_2O$. It has a molecular weight of 112.17 g/mol. This catalyst has the effect, in combination with $H_2O$, of manipulating the foam rise characteristics.

Example 1

Synthesis of Aliphatic Linked Fluorosiloxane Based Triblock Copolymer Pre-Soft-Segment This is a 2 step process. In the first step silanol terminated poly(trifluoropropyl methyl siloxane) is converted into its dihydride derivative. In the next step, this dihydride derivative is reacted with the allyl terminated poly(propylene glycol).

The synthetic procedure is as follows:

Step 1:

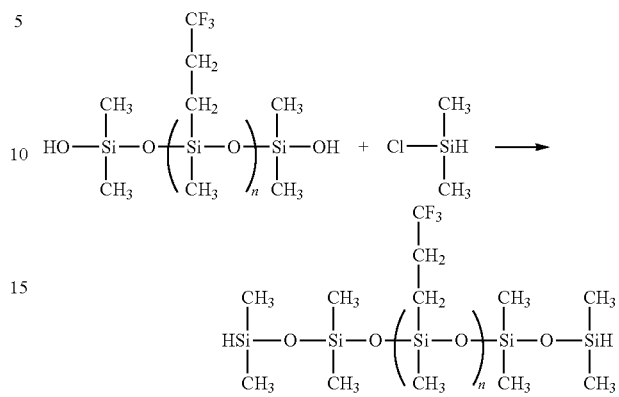

To a 4 neck separable flask fitted with mechanical stirrer, was added 40 g of Silanol terminated poly(trifluoropropyl methylsiloxane) (FMS-9922 from Gelest Inc.) and this was mixed with 50 ml of toluene and fitted with a continuous flush of Nitrogen. To the reaction mixture 7.57 g of dimethyl chlorosilane (DMCS, from Sigma Aldrich) was added slowly over about 20 minutes keeping the temperature of the mixture constant at 30° C. With each addition of dimethyl chlorosilane, the mixture became hazy but cleared in a short period of time. Once the addition of dimethyl chlorosilane was complete, the mixture was heated to 90° C. for 3 hours. The reaction was then washed with excess water several times to reduce the acidity of the mixture. The resulting mixture was dried over silica gel, filtered and vacuumed to remove solvent and traces of water at 65° C. overnight. A clear fluid was then obtained with a very strong Si—H band in infra red spectroscopy (IR) at 2130 cm$^{-1}$, which confirms the reaction. GPC analysis showed the molecular weight to be 1200 g/mol.

Step 2:

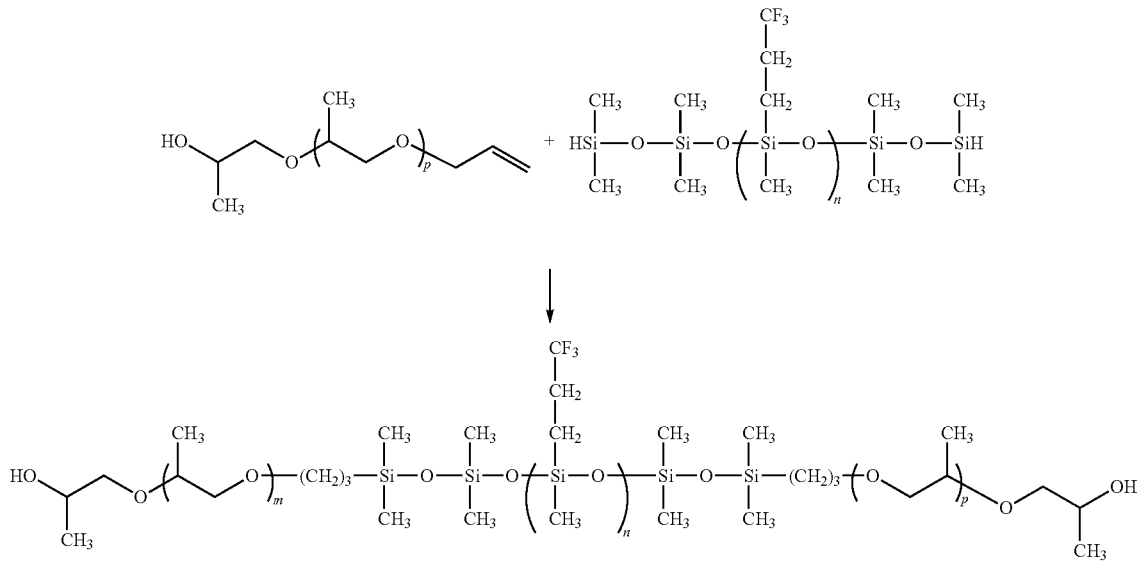

To 90 ml of reagent grade toluene in a 4 neck separable flask fitted with mechanical stirrer, 46.67 g of Allyl terminated poly(propylene glycol) (MW=700 g/mol, Jiangsu GPRO Group Co.) was added and then heated to reflux. Then 40 g of Hydride terminated FMS-9922 was dissolved in 50 ml of reagent grade toluene and the temperature raised to around 90° C. To the reaction mixture 2 drops of hexachloroplatinic (IV) acid (0.01M $H_2PtCl_6$ from Sigma) solution in isopropanol (by Merck) was then added. After this catalyst solution had been added, the mixture was refluxed for 1 hour and the solvent distilled off in order to get the final product. The reaction was followed by H-NMR and gel permeation chromatography (GPC) confirmed the final molecular weight to be 2700 g/mol.

Example 2

Synthesis of Aliphatic Linked Dimethylsiloxane Based Triblock Copolymer Pre-Soft-Segment To 130 ml of reagent grade toluene in a separable flask fitted with a mechanical stirrer, was added 64 g of allyl terminated poly(propylene glycol) (MW=700 g/mol, Jiangsu GPRO Co.) and both were mixed and heated to reflux. Then 40 g of hydride terminated poly(dimethyl siloxane) (Silmer H Di 10 by Siltech Corp.) was dissolved in 50 ml reagent grade toluene and the temperature raised to around 90° C. To this reaction mixture 2 drops of hexachloroplatinic(IV) acid (0.01M $H_2PtCl_6$ from Sigma) solution in isopropanol was added. After this catalyst solution was added, the mixture was refluxed for 1 hour and then the solvent was distilled off in order to get the final product. The reaction was followed with H-NMR and gel permeation chromatography (GPC) confirmed the final molecular weight of the product to be 2300 g/mol.

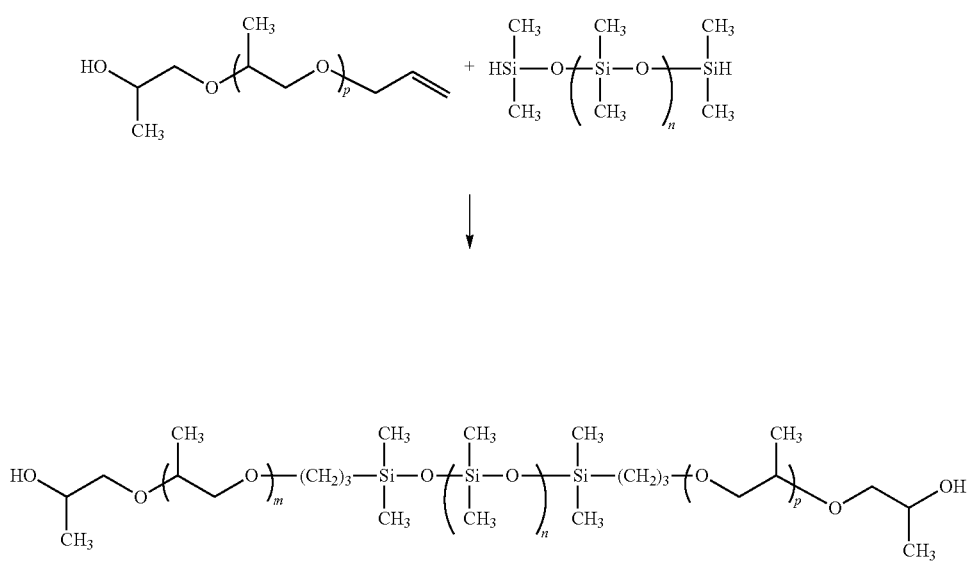

TABLE 1

Resulting polymer block ratios
Stoiciometric ratios for reaction product:

| | Polymer block | | |
|---|---|---|---|
| | PO | F—SiO | PO |
| | m | n | p |
| Ratio | 11 | 9.7 | 11 |

TABLE 2

Polymer block ratios
Stoiciometric ratios for reaction product:

| | Polymer block | | |
|---|---|---|---|
| | PO | SiO | PO |
| | m | n | p |
| Ratio | 11 | 11 | 11 |

Example 3

Synthesis of Aromatic Linked Siloxane Based Triblock Copolymer Pre-Soft-Segment

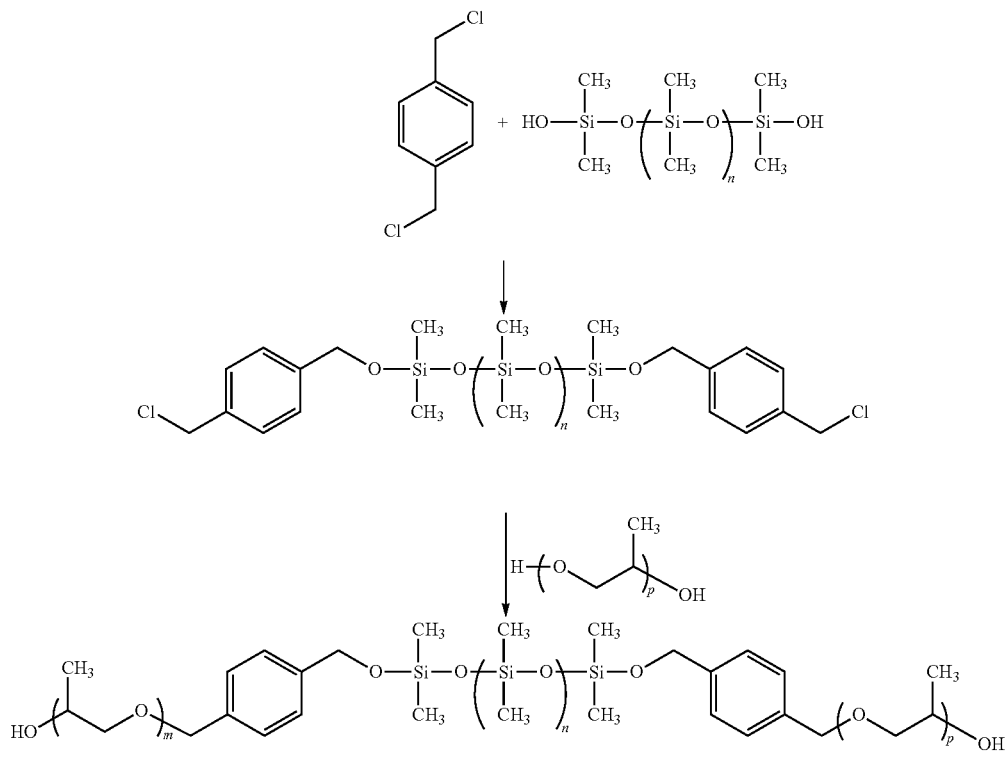

To a 100 ml separable flask fitted with a mechanical stirrer, 15 g of hydroxy terminated polydimethyl siloxane (DMS-S14 from Gelest Inc.) was added along with 5.36 g of dichloro p-xylene (from Sigma) and 0.0089 g of Copper(II) acetylacetonate (Cu(Acac)$_2$ from Sigma). The reaction mixture was refluxed at 110° C. for 5 hrs. At this point, 19.77 g of hydroxy terminated poly(propylene glycol) (from Sigma) was added dropwise and the reaction mixture was then refluxed for another 15 hr. The progress of reaction was followed by $^1$H-NMR and the final molecular weight, determined by gel permeation chromatography (GPC), was 3000 g/mol.

H-NMR Analysis:

Solvent used for $^1$H-NMR analysis is CDCl$_3$.

Aromatic H=7.25-7.45 ppm, —CH$_2$=4.5-4.6 ppm, —CH$_3$ (of PPO)=1-1.4 ppm, —CH$_2$ (of PPO)=3.2-3.8 ppm, —OH (of PPO)=3.8-4 ppm, —CH$_3$ (silanol)=0.5-0.8 ppm.

TABLE 3

Resulting polymer block ratios
Stoiciometric ratios for reaction product:

| | Polymer block | | |
|---|---|---|---|
| | PO<br>m | SiO<br>n | PO<br>p |
| Ratio | 14 | 15.5 | 14 |

Example 4

Synthesis of Aromatic Linked Fluorosiloxane Based Triblock Copolymer Pre-Soft-Segment

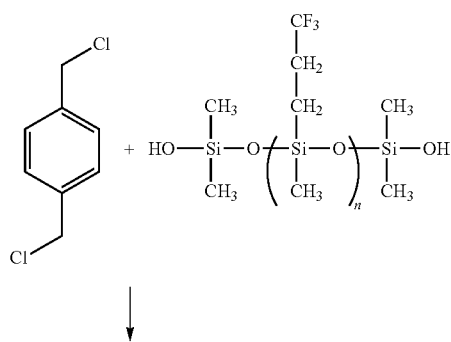

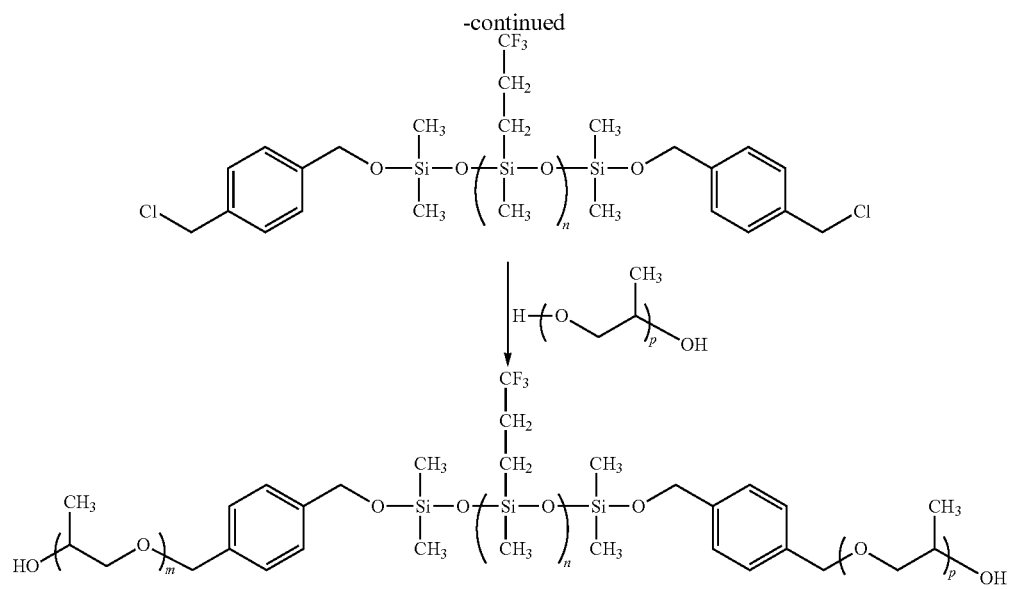

To a 100 ml separable flask fitted with a mechanical stirrer, 15 g of hydroxy terminated polytrifluoromethyl siloxane (FMS-9922, Gelest inc.) was added along with 5.9 g of di-chloro p-xylene and 0.0098 g of copper(II) acetylacetonate (Cu(Acac)$_2$ from Sigma). The reaction mixture was refluxed at 110° C. for 5 hrs. At this point, 21.75 g of hydroxy termi-nated poly(propylene glycol) (from Sigma) was added drop-wise to the reaction mixture. The reaction was refluxed for another 15 hr. The progress of reaction was followed by $^1$H-NMR analysis and the molecular weight, determined by gel permeation chromatography (GPC), was 3100 g/mol.

$^1$H-NMR analysis: Solvent used for H-NMR analysis is CDCl$_3$.

Aromatic $^1$H=7.25-7.45 ppm, —CH$_2$=4.5-4.6 ppm, —CH$_3$ (of PPO)=1-1.4 ppm, —CH$_2$ (of PPO)=3.2-3.8 ppm, —OH (of PPO)=3.8-4 ppm, —CH$_3$ (silanol)=0.5-0.8 ppm.

TABLE 4

Polymer block ratios
Stoiciometric ratios for reaction product:

| | Polymer block | | |
|---|---|---|---|
| | PO<br>m | FSiO<br>n | PO<br>p |
| Ratio | 14 | 9.2 | 14 |

Example 5

Preparation of Water Blown Foam

The pre-soft segments prepared can be described as having polymer block ratios which are numerically represented by the letters m, n and o for the constituents PO/SiO/PO respec-tively. The triblock copolymers prepared in Examples 1 and 2 with specific m, n, o ratios were formulated into polyure-thane/urea foams as illustrated by Table 7.

The process for preparing the foam was a two-step proce-dure. The following describes the method of manufacture of the first product in Table 7. The same procedure was used to prepare other foams as described by Table 8.

Step 1) Firstly a mixture was made with 0.041 g of DABCO LV-33 (Airproducts), 0.120 g of bismuth neodecanoate (Bicat 8108M from Shepherd chemicals), 0.467 g of diethanol amine (DEOA, from Sigma), 7.917 g of synthe-sized block copolymer, 0.200 g water and 0.1 g of surfac-tant (Niax L-618 from Airproducts) in a plastic flat bot-tomed container. This is then thoroughly mixed manually for 30 sec until a homogenous mixture was obtained.

Step 2) To the above mixture, 15 g of a diisocyanate prepoly-mer (PPT 95A Airproducts) was added. This was then thoroughly mixed by a mechanical stirrer for about 5 sec-onds. The material was then molded and cured at 70° C. for 2.5 hours and post cured at 50° C. for another 3 hours.

TABLE 5

Formulation details for foam

| Formulation<br>Identification | Polymer block<br>(PO/SiO/PO)<br>Ratio m:n:p | DABCO | BICAT | DEOA | H$_2$O |
|---|---|---|---|---|---|
| VF230209A | 11:11:11 | 0.0325 | 0.015 | 0.40 | 1.0 |
| VF090309B | 11:9:11 | 0.0325 | 0.015 | 0.40 | 1.0 |

Example 6

Comparative Example of Formulation of Water Blown Foam from Triblock Copolymer Pre-Soft Segment and Individual Homopolymers Polyurethane/urea polymer foams from Example 5 were compared to foams made from the stoiciometric equivalent homopolymer soft segments. The foams with homopolymer based soft segments (VF130309 and VF190309) shown in FIG. 88 were produced as follows (VF130309):

Step 1) Firstly a mixture was made with 0.041 g of DABCO LV-33 (Airproducts), 0.120 g of bismuth neodecanoate (Bicat 8108M from Shepherd chemicals), 0.467 g of diethanol amine (DEOA, from Sigma), 3.056 g of poly (dimethyl siloxane) diol (DMS-s14 Gelest Inc.), 1.633 g of polypropylene oxide (Mw=700 g/mol), 0.200 g water and 0.1 g of surfactant (Niax L-618 from Airproducts). These were added to a plastic flat bottomed container and were thoroughly mixed manually for 30 sec until a homogenous mixture was obtained.

Step 2) To the above mixture, 15 g of a diisocyanate prepolymer (PPT 95A Airproducts) was added. This was then thoroughly mixed by a mechanical stirrer for 5 seconds. The material was then molded and cured at 70° C. for 2.5 hours and post cured at 50° C. for another 3 hours.

Figure 88:
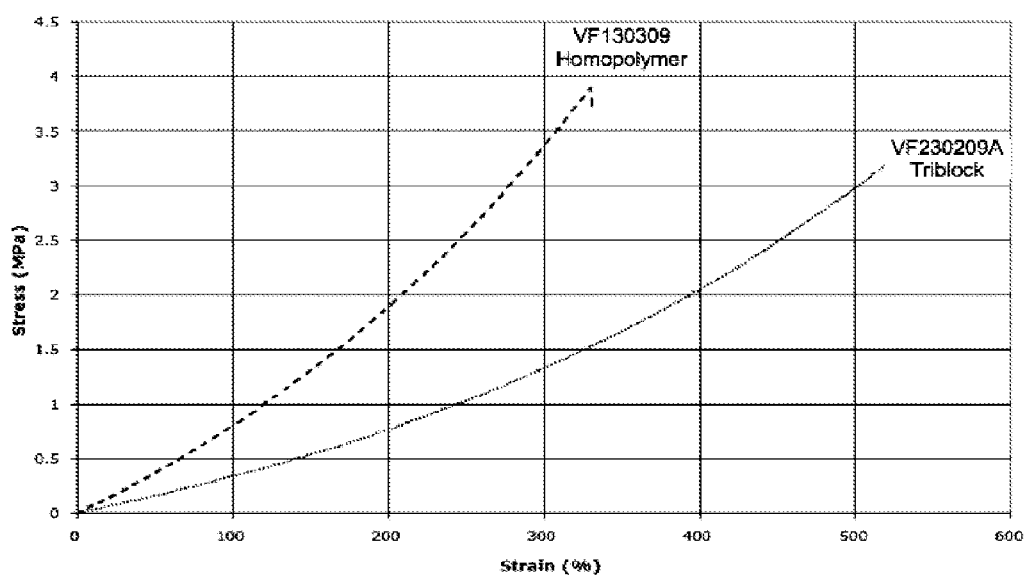
FIG. 88 is a graph of comparative mechanical properties of homo (VF130309) and triblock copolymer (VF230209A) soft segments.
Figure 89:
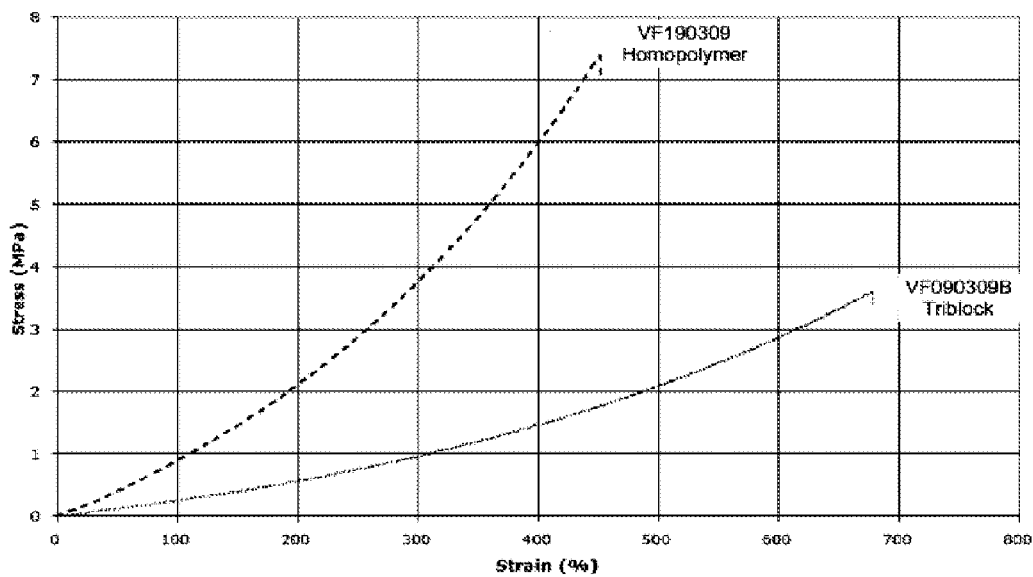
FIG. 89 is a graph of comparative mechanical properties of home (VF190309) and triblock copolymer (VF090309) soft segments.

The foams in this example were made into dumbell shapes for tensile testing. FIGS. 88 and 89 illustrate the difference in mechanical behaviour between the comparative materials indicating a favourable lowering in modulus for the triblock copolymer pre-soft-segments.

Example 7

Figure 90:
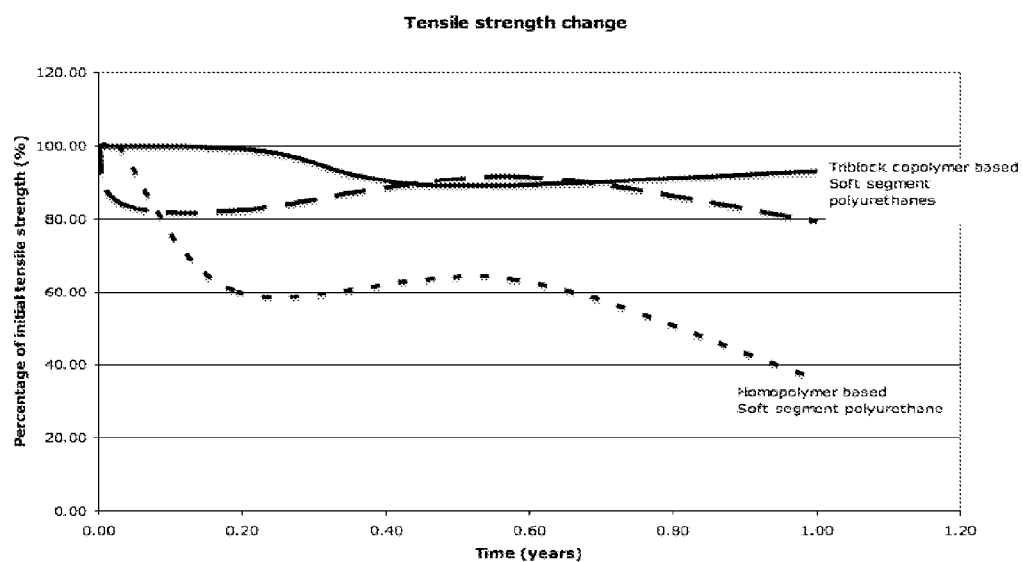
FIG. 90 is a graph illustrating the mechanical performance of triblock copolymer soft segments versus homopolymer soft segment during accelerated aging in simulated gastric fluid.

Comparative Stability of Triblock Copolymer Soft Segment Versus Homopolymer Soft Segment Tensile test specimens were prepared in the same manner to the materials used in Example 4 and were subjected to accelerated aging in simulated gastric fluid (as per United States Pharmacopeia, "USP"). The materials produced with the pre-synthesised triblock copolymer soft segments resulted in substantially improved mechanical stability in gastric fluid as compared to the urethane/urea linked homopolymer equivalent as illustrated in FIG. 90. This facilitates the use of such materials for prolonged periods in digestive and more specifically gastric environments.

Example 8

Preparation of Water Blown Foams

Several water blown polyurethane/urea foams were also produced with varying PO/EO/SiO polymer block ratios. The process for preparing the foam as described above was used.

TABLE 6

Water blown formulations incorporating siloxane containing copolymer pre-soft-segments.

| Polymer block ratio (PO/EO/SiO) m:n:p | DABCO | BICAT | DEOA | H$_2$O |
|---|---|---|---|---|
| 41.5:8.3:0.5 | 0.114 | 0.022 | 0.22 | 2.72 |
| 40.2:7.8:0.5 | 0.114 | 0.022 | 0.22 | 2.72 |
| 37.5:7:0.5 | 0.114 | 0.022 | 0.22 | 2.72 |
| 33.5:5.7:0.5 | 0.114 | 0.022 | 0.22 | 2.72 |
| 29.6:4.4:0.5 | 0.114 | 0.022 | 0.22 | 2.72 |
| 21.6:1.8:0.5 | 0.114 | 0.022 | 0.22 | 2.72 |
| 19:1:0.5 | 0.114 | 0.022 | 0.22 | 2.72 |
| 29.6:4.5:1.1 | 0.114 | 0.022 | 0.22 | 2.72 |

The results from the formulations described in Table 6 are shown in Table 7.

TABLE 7

Results from mechanical testing of foams from Table 5

| Polymer block ratio (PO/EO/SiO) m:n:p | % Elongation | Tensile Strength (N) |
|---|---|---|
| 41.5:8.3:0.5 | 233 | 0.46 |
| 40.2:7.8:0.5 | 243 | 0.31 |
| 37.5:7:0.5 | 237 | 0.3 |
| 33.5:5.7:0.5 | 260 | 0.23 |
| 29.6:4.4:0.5 | 320 | 0.23 |
| 21.6:1.8:0.5 | 497 | 0.23 |
| 19:1:0.5 | 462 | 0.22 |
| 29.6:4.5:1.1 | 437 | 0.29 |

Example 9

Use Example

Devices for use in the gastrointestinal system have historically not been made from specifically designed materials. Off the shelf materials used for application in the corrosive environment of the stomach have limited biostability and generally lose their functionality after a short time.

The foam of the invention can be used for production of a valve of the type described in our US2007-0198048A, the entire contents of which are incorporated herein by reference. The valve has an open position and a closed position. The valve will have a proximal end and a distal end. The valve material can open from the proximal direction when the action of swallowing (liquid or solid) stretches an orifice by between 100% and 3000% in circumference. The open orifice optionally closes non-elastically over a prolonged period of time, thus mimicking the body's natural response. The duration taken to close may be between 2 and 15 sec. The material can stretch to between 100%-300% from the distal direction when gas, liquid or solids exceeds a pre-determined force of between 25 cm H$_2$O and 60 cm H$_2$O. In some embodiments, the material absorbs less than 15% of its own mass of water at equilibrium. In some embodiments, the material loses (leaches) less than 3% of it's own mass at equilibrium in water or alcohol. In some embodiments, the material loses less than 10% of its tensile strength when immersed in a simulated gastric fluid at pH 1.2 for 30 days. In some embodiments, the valve material loses less than 25% of its % elongation when immersed in a simulated gastric fluid at pH 1.2 for 30 days.

Example 10

Valve Functional Testing

The healthy lower esophageal sphincter (LES) remains closed until an individual induces relaxation of the muscle by swallowing and thus allowing food to pass in the antegrade direction. Additionally when an individual belches or vomits they generate enough pressure in the stomach in the retrograde direction to overcome the valve. An anti-reflux valve must enable this functionality when placed in the body, thus a simple functional test is carried out to asses performance.

It has been reported that post fundoplication patients have yield pressures between 22-45 mm Hg and that most of the patients with gastric yield pressure above 40 mm Hg experienced problems belching See *Yield pressure, anatomy of the cardia and gastro-oesophageal reflux*. Ismail, J. Bancewicz, J. Barow British Journal of Surgery. Vol: 82, 1995, pages: 943-947. Thus, in order to facilitate belching but prevent reflux, an absolute upper GYP value of 40 mm Hg (550 mm H$_2$O) is reasonable. It was also reported that patients with visible esophagitis all have gastric yield pressure values under 15 mm Hg, therefore, there is good reason to selectively target a minimum gastric yield pressure value that exceeds 15 mm Hg. See Id. An appropriate minimum gastric yield pressure value would be 15 mm Hg+25% margin of error thus resulting in a minimum effective valve yield pressure value of 18.75 mm Hg or 255 mm H$_2$O.

Figure 91:
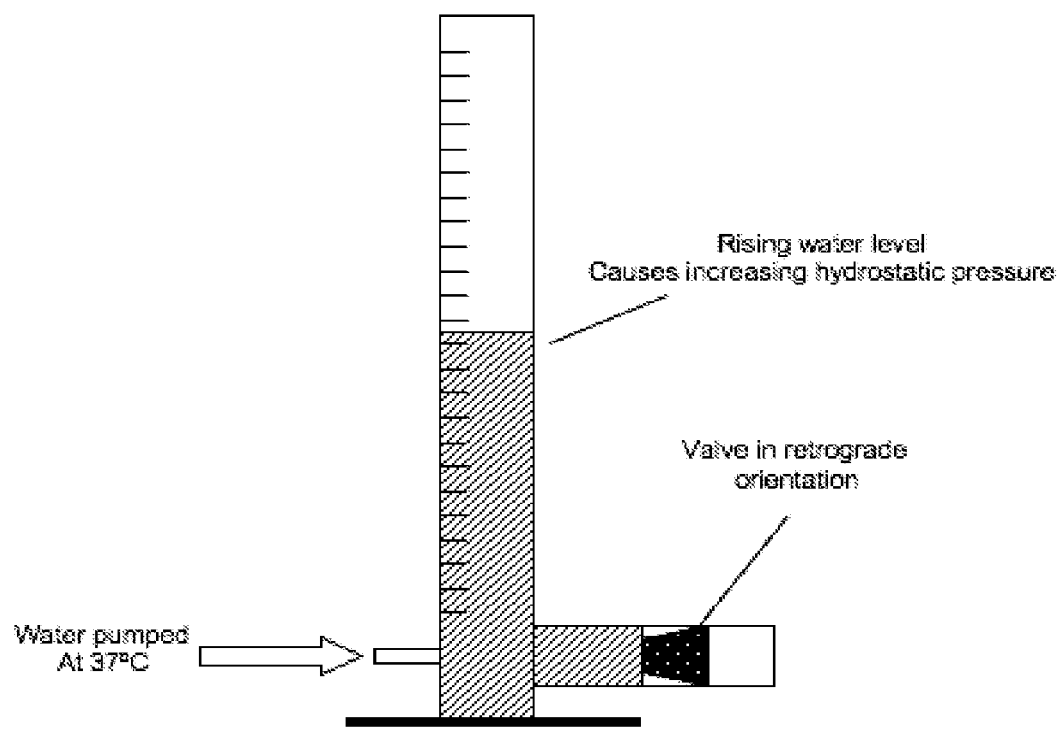
FIG. 91 depicts a gastric yield pressure test apparatus as utilized in Example 10.

The test apparatus consists of a 1 m high vertical tube as shown in FIG. 91, to which is connected a peristaltic pump and a fitting that is designed to house the valve to be tested.

The valve to be tested is placed in a water bath at 37° C. for 30 minutes to allow its temperature to equilibrate. Once the temperature of the valve has equilibrated it is then installed into the housing such that the distal closed end of the valve faces the inside of the test apparatus. The pump is then switched on at a rate of 800 ml/min to begin filling the vertical tube. The rising column of water exerts a pressure that forces the valve shut initially. As the pressure in the column rises the valve reaches a point where it everts and allows the water to flow through. This point, known as the yield pressure, is then recorded and the test repeated four times.

Example 11

Rationale for Accelerated Aging of Material

Clinical Condition being Simulated

The lower oesophagus of a normal patient can be exposed to the acidic contents of the stomach periodically without any adverse side effects. However, patients with gastro esophageal reflux disease experience damage to the mucosa of the lower oesophagus due to increased exposure to the gastric contents. Exposure of the lower oesophagus to acidic gastric contents is routinely measured in the clinic using dedicated pH measurement equipment. A typical procedure involves measuring pH over a 24-hour period. The levels of acid exposure in pathological reflux disease patients is summarised in Table 8 from six clinical references. See DeMeester T R, Johnson L F, Joseph G J, et al. *Patterns of Gastroesophageal Reflux in Health and Disease Ann. Surg.* October 1976 459-469; Pandolfino J E, Richter J E, Ours T, et al. *Ambulatory Esophageal pH Monitoring Using a Wireless System Am. J. Gastro* 2003; 98:4; Mahmood Z, McMahon B P, Arfin Q, et al. *Results of endoscopic gastroplasty for gastroesophageal reflux disease: a one year prospective follow-up Gut* 2003; 52:34-9; Park P O, Kjellin T, Appeyard M N, et al. *Results of endoscopic gastroplasty suturing for treatment of GERD: a multicentre trial Gastrointest endosc* 2001; 53:AB115; Filipi C J, Lehman G A, Rothstein R I, et al. *Transoral flexible endoscopic suturing for treatment of GERD: a multicenter trial Gastrointest endosc* 2001; 53 416-22; and Arts J, Slootmaekers S Sifrim D, et al. *Endoluminal gastroplication (Endocinch) in GERD patient's refractory to PPI therapy Gastroenterology* 2002; 122:A47.

TABLE 8

Summary of acid exposure in patients with reflux disease

| Investigator | Number of patients | Details | % 24 h < pH4 |
|---|---|---|---|
| DeMeester | 54 | Combined refluxers | 13.5 |
| Pandolfino | 41 | Gerd | 6.5 |
| Mahmood | 21 | Gerd | 11.11 |
| Park | 142 | Gerd | 8.5 |
| Filipi | 64 | Gerd | 9.6 |
| Arts | 20 | Gerd | 17 |
| Average | | | 11.035 |

Key Clinical Parameters

Considering that the lower oesophagus is exposed to the acidic pH exposure time for an average of 11% of the measurement period, an accelerated aging methodology can easily be conceived. Constant exposure of a test material to the gastric contents (or USP Simulated Gastric Fluid —Reference USP Pharmacopeia) would represent an almost 10-fold increase in the rate of aging. Thus the time required to simulate one year of exposure of the lower oesophagus to the gastric contents is described by equation 1.

$$\left(\frac{11.035}{100}\right) \times 365 \text{ days} = 40.28 \text{ days} \quad \text{Equation 1}$$

Clinical Rationale

Immersion of test specimens in USP Simulated gastric fluid for 40.27 days at 37° C. will approximate one year's exposure of the lower oesophagus to acidic gastric contents in a GERD patient's scenario.

| Simulated Exposure | Real Time |
|---|---|
| 1 year | 40.28 days |
| 2 years | 80.56 days |
| 3 years | 120.84 days |

Figure 92A:
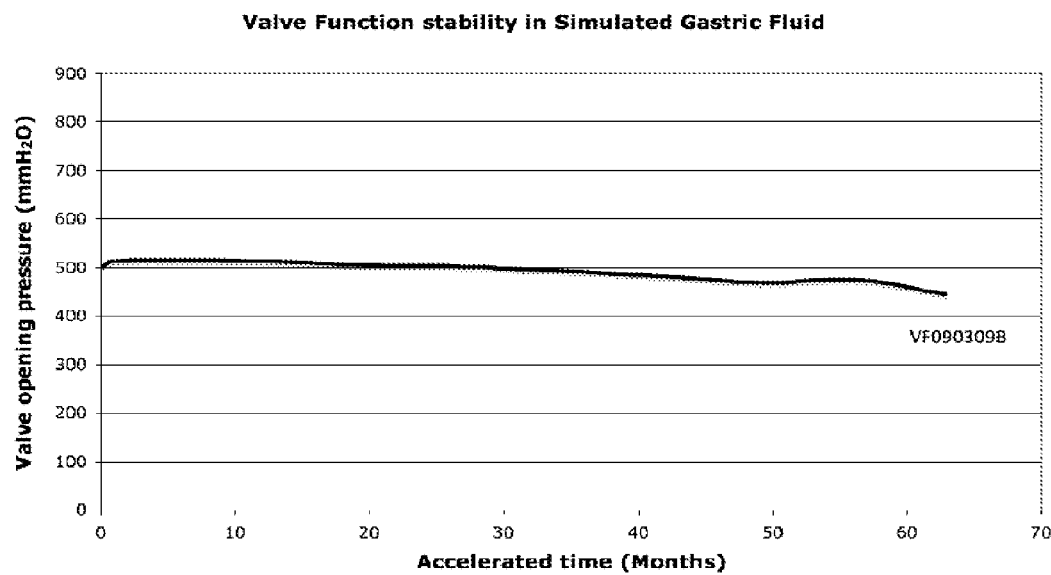
FIG. 92A and FIG. 92B depict results of accelerated stability of a valve prepared from a viscoelastic foam of the present invention.
Figure 92B:
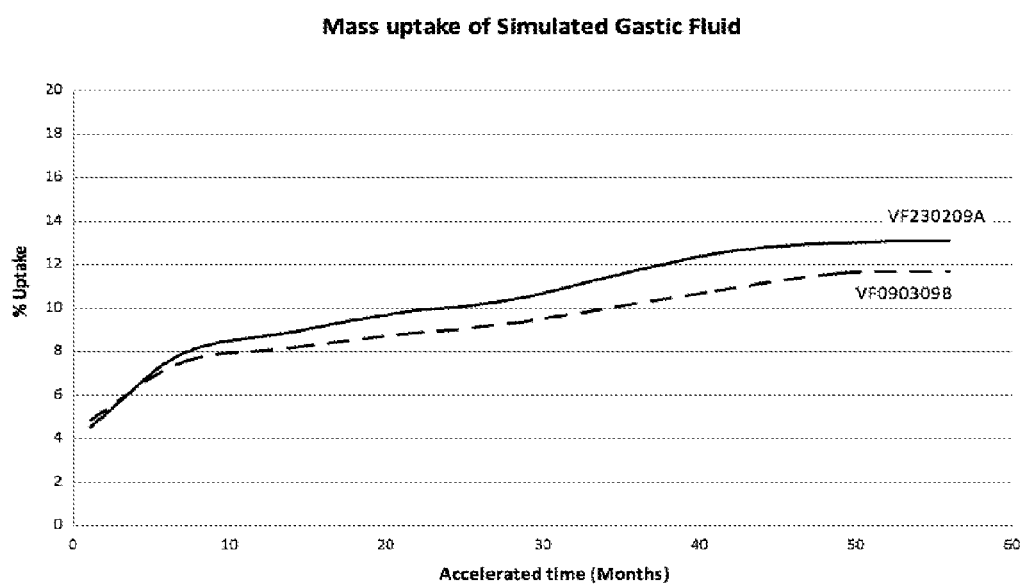

Results of accelerated stability of a valve prepared from a viscoelastic foam of the present invention are depicted in FIGS. 92A and 92B.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The invention is not limited to the embodiments hereinbefore described which may be varied in detail.

The invention claimed is:

1. A medical device for placement in a gastrointestinal tract, the medical device comprising:
    a valve member comprising a biomimetic viscoelastic polymeric foam material, the valve member having a proximal outer support region with a rim;
    at least four valve leaflets;
    a main body region extending between the rim and the valve leaflets, the main body region having a generally concave outer face and a generally convex inner face, the valve member having a normally closed configuration in which the leaflets are engaged at a region of co-aption of the valve leaflets and an antegrade open configuration;
    the valve having a retrograde open configuration in response to a retrograde force, the valve leaflets and at least a portion of the main body region of the valve configured to invert to allow flow in the retrograde direction and, on reduction in retrograde forces, the main body region and the valve leaflets configured to automatically revert to the normally closed configuration under an inherent biasing of the viscoelastic polymeric foam material;
    the main body region of the valve member having a first thickness, the valve leaflets at the region of co-aption having a second thickness which is greater than the first thickness to define a reinforced region which extends in a longitudinal direction; and a support member which is configured to engage with a wall of the gastrointestinal tract, the rim of the valve being mounted to the support member.

2. The medical device as claimed in claim 1 wherein the valve is an esophageal valve.

3. The medical device as claimed in claim 1 wherein the valve has the antegrade open configuration in which the valve leaflets are opened in response to an antegrade force to allow flow through the valve, wherein the retrograde force is larger than the antegrade force.

4. The medical device as claimed in claim 1 wherein the rim of the valve body is reinforced.

5. The medical device as claimed in claim 1 wherein a pressure of 0.7 mm Hg in an antegrade direction is sufficient to allow a flowrate through the valve of 140ml/min.

6. The medical device as claimed in claim 1 wherein the retrograde force required to open the valve is a pressure of greater than 15 mm Hg and less than 40 mm Hg.

7. The medical device as claimed in claim 1 wherein the viscoelastic foam is stable to gastric fluid for at least 3 months, for at least 4 months, for at least 5 months, for at least 6 months, for at least 7 months, for at least 8 months, for at least 9 months, for at least 10 months, for at least 11 months, or for at least one year.

8. The medical device as claimed in claim 1 wherein the viscoelastic foam takes up less than 5%, less than 10%, less than 15%, less than 20%, less than 25%, or less than 30% by weight of water at equilibrium.

9. The medical device as claimed in claim 1 wherein the viscoelastic foam has a % elongation of from 50% to 3000%, or 200 % to 1200%.

10. The medical device as claimed in claim 1 wherein the viscoelastic foam has a tensile strength of from 0.01 to 5 MPa, or 0.1 to 1.0 MPa, or 0.25 to 0.5 MPa.

11. The medical device as claimed in claim 1 wherein the viscoelastic foam has a Young's Modulus of 0.1 to 0.6 MPa, or 0.1 to 0.5 MPa.

12. The medical device as claimed in claim 1 wherein the viscoelastic foam has a density of from 0.1 g/cm$^3$, or 0.3 to 1.2 g/cm$^3$, or 0.8 to 0.9 g/cm$^3$, or 0.5 to 0.6 g/cm$^3$.

13. The medical device as claimed in claim 1 wherein the region of co-aption of the valve leaflets has an axial extent of from 1 mm to 5 mm.

14. The medical device as claimed in claim 1 wherein the second thickness is from 0.1 mm to 10 mm.

* * * * *